United States Patent
Karuppasamy

(10) Patent No.: US 11,446,169 B2
(45) Date of Patent: Sep. 20, 2022

(54) BIFURCATED IMPLANT DELIVERY SYSTEM

(71) Applicant: THE CLEVELAND CLINIC FOUNDATION, Cleveland, OH (US)

(72) Inventor: Karunakaravel Karuppasamy, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 329 days.

(21) Appl. No.: 16/492,659

(22) PCT Filed: Mar. 9, 2018

(86) PCT No.: PCT/US2018/021731
§ 371 (c)(1),
(2) Date: Sep. 10, 2019

(87) PCT Pub. No.: WO2018/165542
PCT Pub. Date: Sep. 13, 2018

(65) Prior Publication Data
US 2020/0046531 A1    Feb. 13, 2020

Related U.S. Application Data

(60) Provisional application No. 62/469,566, filed on Mar. 10, 2017.

(51) Int. Cl.
*A61F 2/954* (2013.01)
*A61F 2/97* (2013.01)
*A61F 2/966* (2013.01)

(52) U.S. Cl.
CPC .............. *A61F 2/954* (2013.01); *A61F 2/97* (2013.01); *A61F 2002/9665* (2013.01)

(58) Field of Classification Search
CPC ...... A61F 2/95–9/97; A61F 2002/9665; A61F 2/954; A61M 25/0668
See application file for complete search history.

(56) References Cited

U.S. PATENT DOCUMENTS 5,980,533 A   11/1999   Holman
6,143,002 A   11/2000   Vietmeier
(Continued)

FOREIGN PATENT DOCUMENTS

EP    2036519 A1    3/2009
WO    99/34749 A1   7/1999

OTHER PUBLICATIONS

PCT International Search Report and Written Opinion for corresponding International Application Serial No. PCT/US2018/021731, dated May 22, 2018, pp. 1-14.
(Continued)

*Primary Examiner* — Kathleen S Holwerda
(74) *Attorney, Agent, or Firm* — Tarolli, Sundheim, Covell & Tummino LLP

(57) ABSTRACT

A bifurcated implant delivery system is provided for deploying a bifurcated expandable implant in a patient lumen. A shaft has at least two shaft proximal openings. A shaft distal end has at least two shaft branches longitudinally extending from a shaft body distal end. Each of the shaft branches has a shaft open tip. The shaft has at least one shaft lumen that longitudinally extends between a respective shaft proximal opening and at least one respective shaft open tip. A reinforcing element longitudinally extends from the shaft body distal end. An outer sheath has an outer sheath proximal opening and at least one outer sheath open tip. An outer sheath lumen longitudinally extends between the outer sheath proximal opening and the at least one outer sheath open tip. The outer sheath lumen is for selectively holding
(Continued)

at least a portion of the shaft and a bifurcated expandable implant therein.

17 Claims, 94 Drawing Sheets

(56) References Cited

U.S. PATENT DOCUMENTS

| | | |
|---|---|---|
| 6,908,477 B2 | 6/2005 | McGuckin, Jr. et al. |
| 7,476,243 B2 | 1/2009 | Eidenschink |
| 7,481,837 B2 | 1/2009 | Wilson |
| 8,128,686 B2 | 3/2012 | Paul, Jr. et al. |
| 9,125,764 B2 | 9/2015 | Shaw |
| 9,623,603 B2 | 4/2017 | Hamer et al. |
| 10,687,969 B2 * | 6/2020 | Folan ................. A61F 2/82 |
| 2003/0135259 A1 | 7/2003 | Simso |
| 2006/0178726 A1 * | 8/2006 | Douglas ............... A61F 2/954 623/1.16 |
| 2010/0268318 A1 | 10/2010 | Glynn |
| 2010/0274339 A1 * | 10/2010 | Muzslay ............... A61F 2/07 623/1.11 |
| 2012/0016454 A1 * | 1/2012 | Jantzen ............... A61F 2/954 623/1.11 |
| 2012/0130475 A1 | 5/2012 | Shaw |
| 2014/0148891 A1 * | 5/2014 | Johnson ............... A61F 2/97 623/1.11 |
| 2016/0242943 A1 | 8/2016 | Riedy et al. |

OTHER PUBLICATIONS

PCT International Search Report and Written Opinion for corresponding International Application Serial No. PCT/US2018/021755, dated May 17, 2018, pp. 1-14.

* cited by examiner

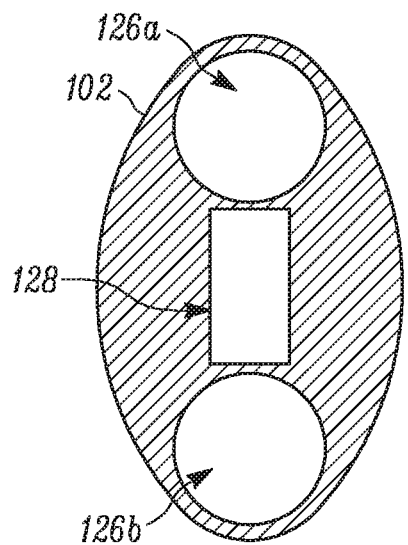
FIG. 1B
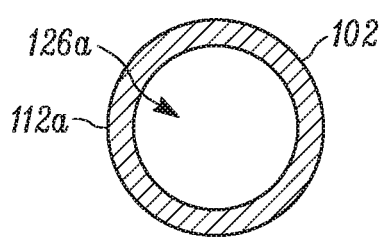
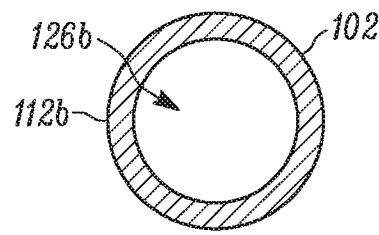
FIG. 1C

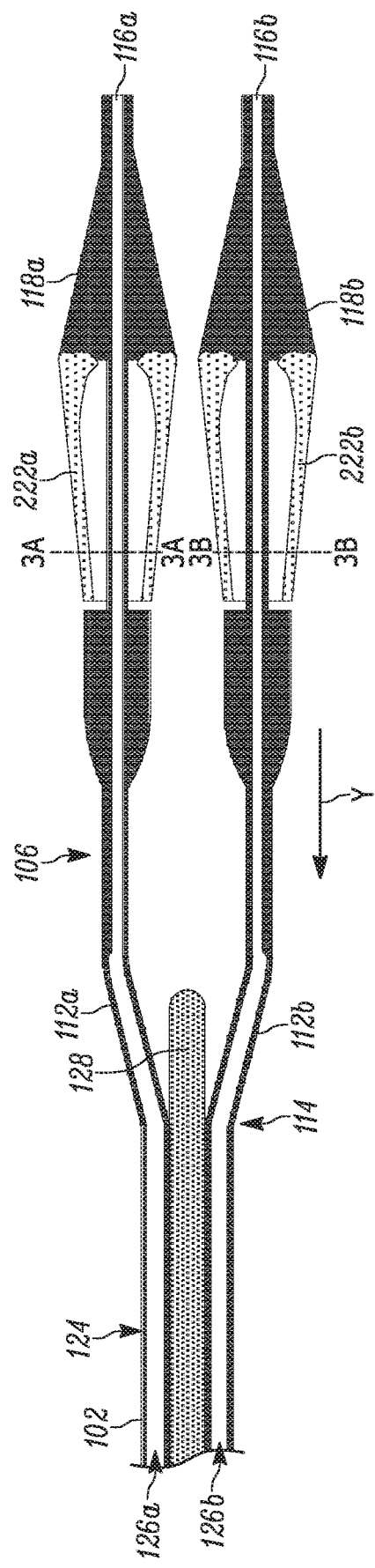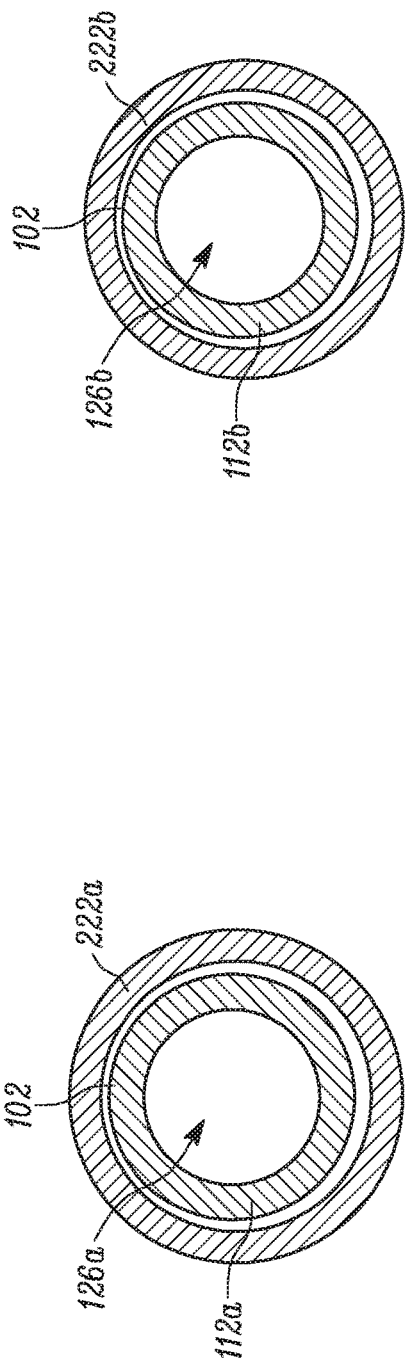
FIG. 3
FIG. 3A
FIG. 3B

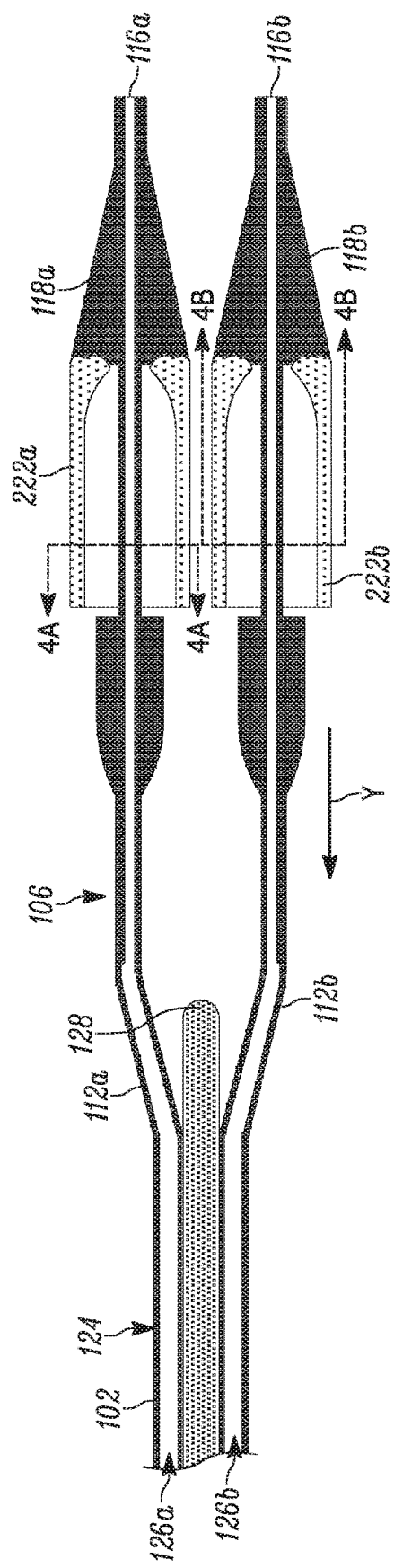
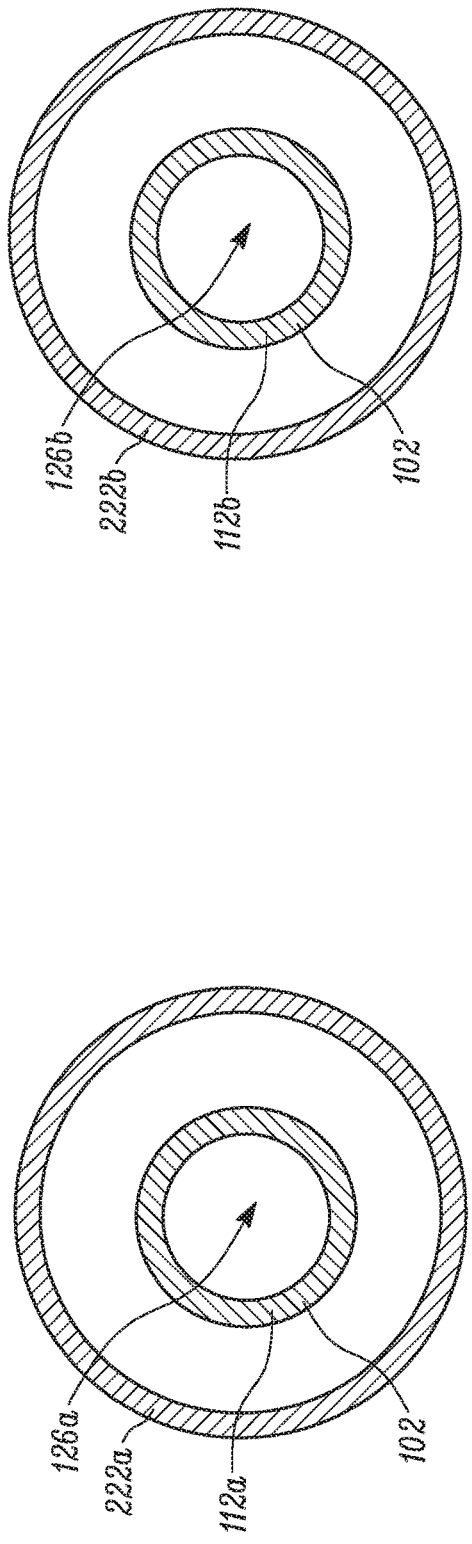
FIG. 4
FIG. 4A
FIG. 4B

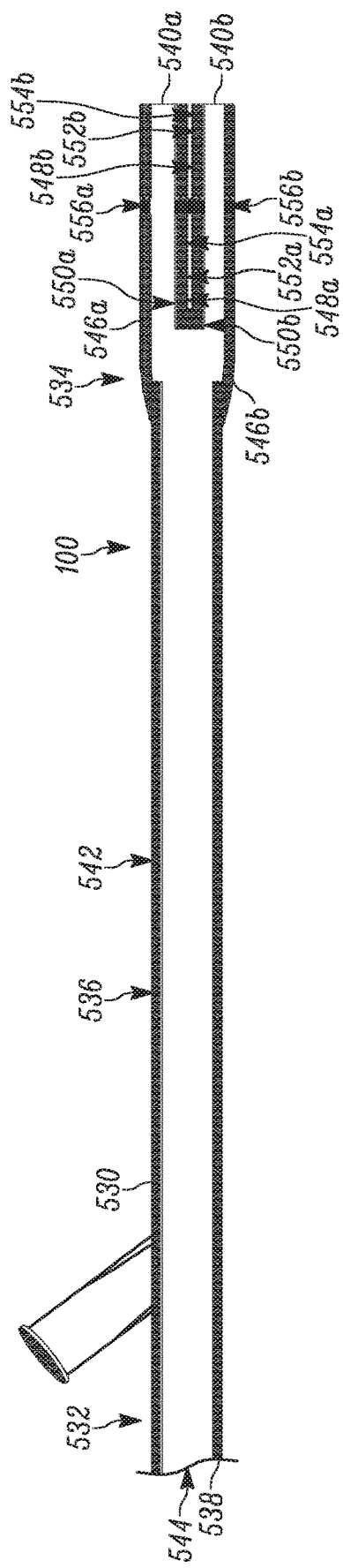

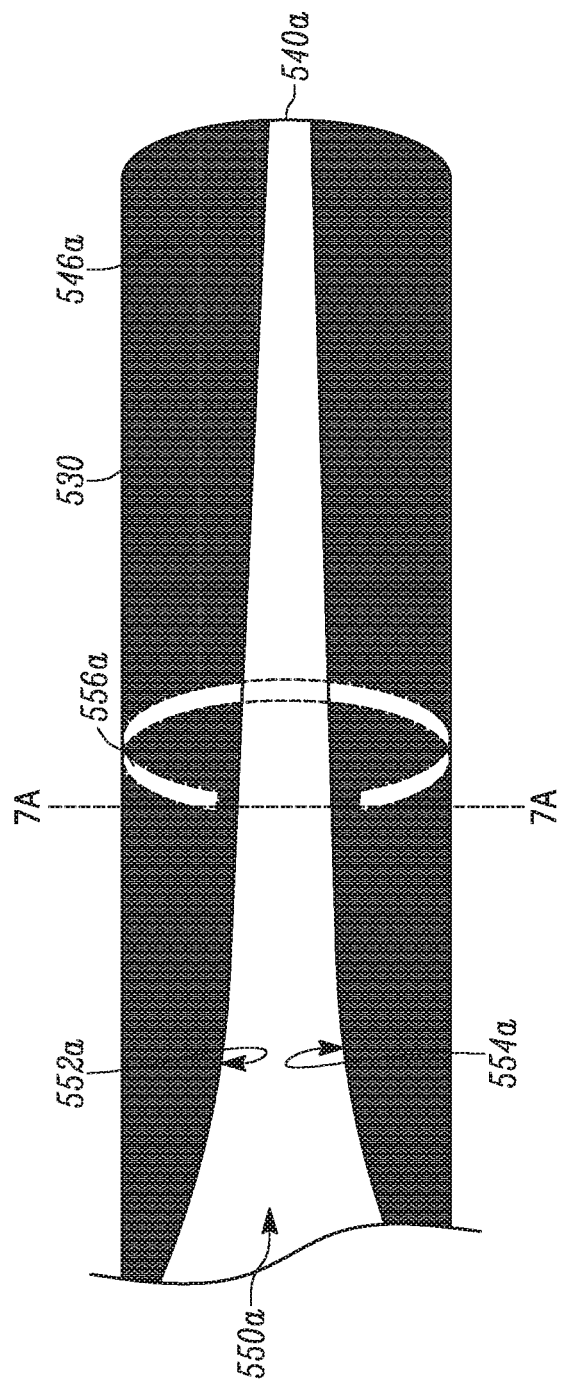
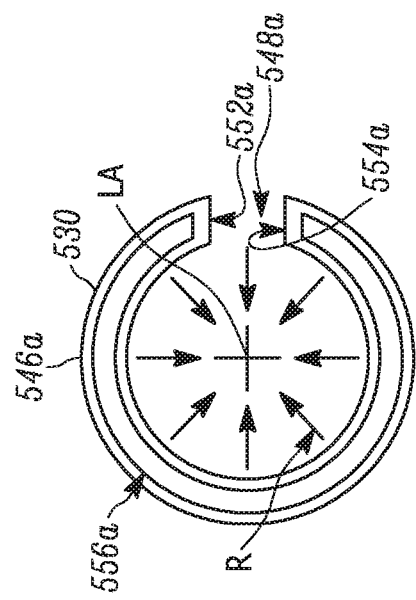
FIG. 7
FIG. 7A

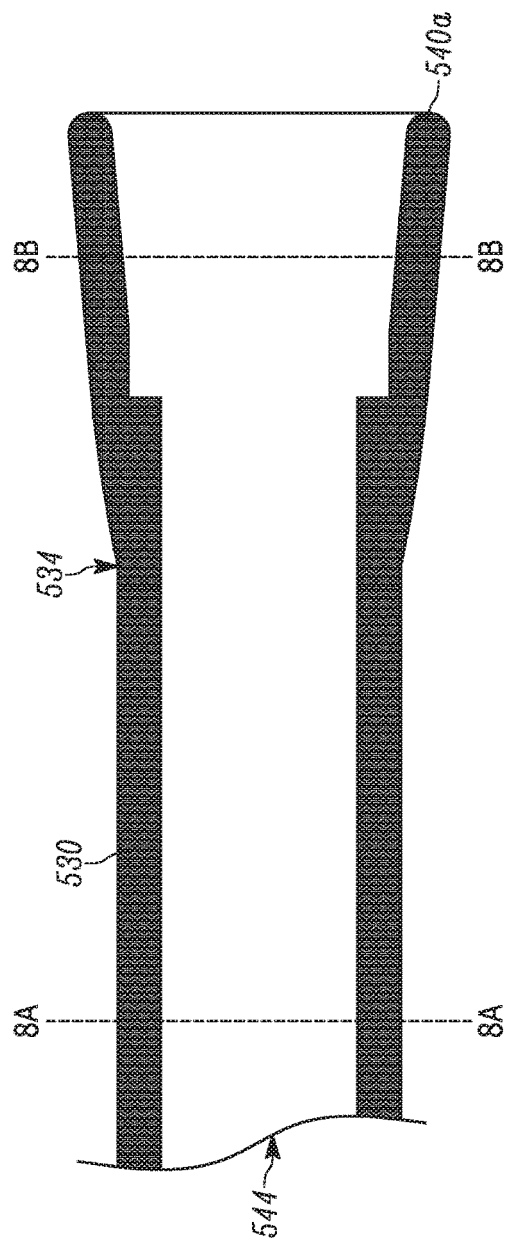
FIG. 8
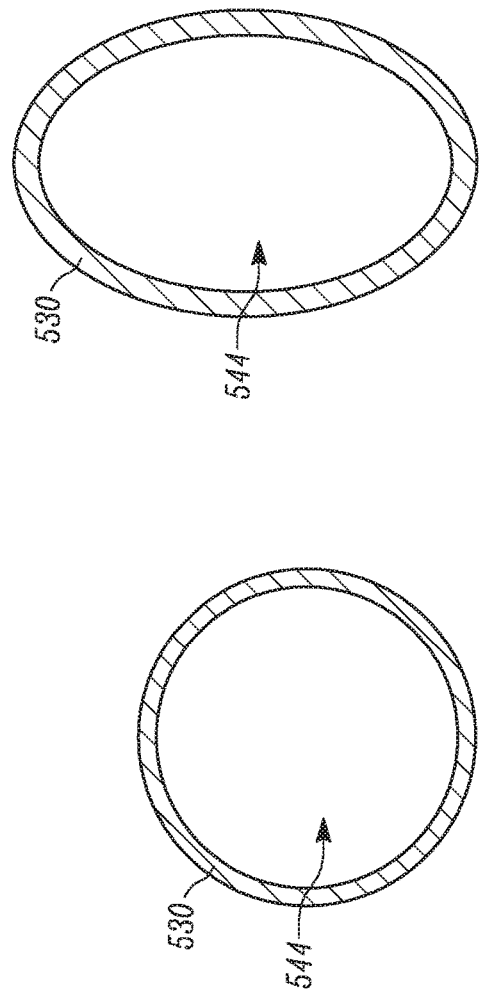
FIG. 8A
FIG. 8B

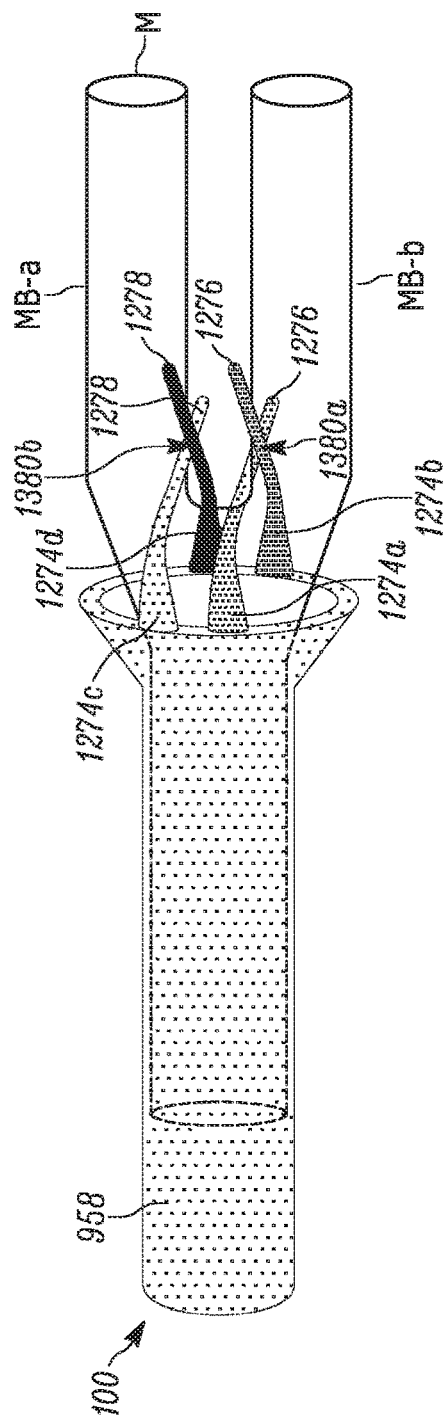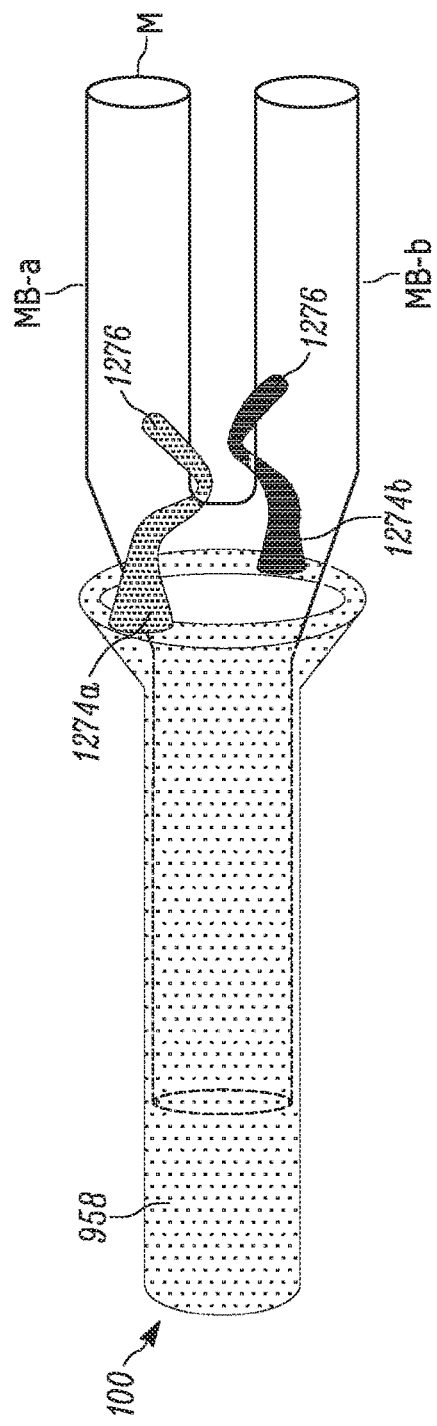
FIG. 23
FIG. 24

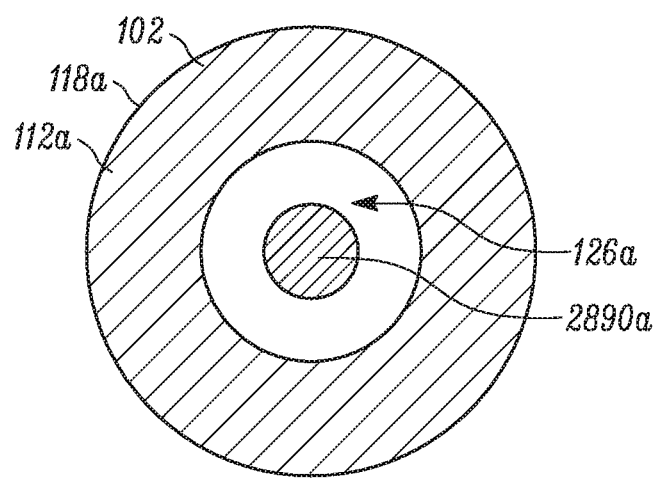
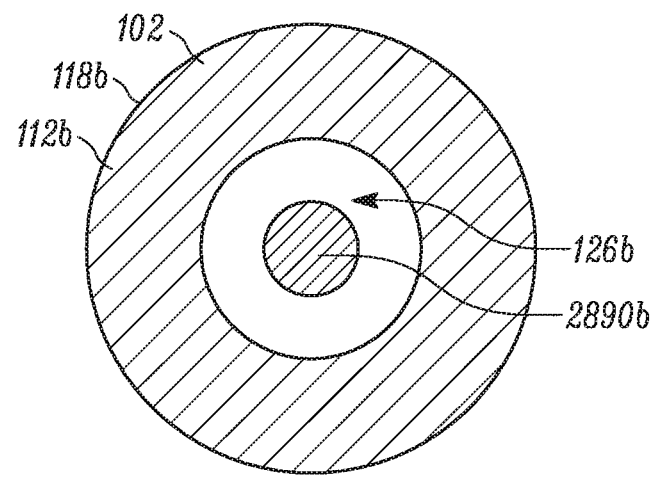
FIG. 29F

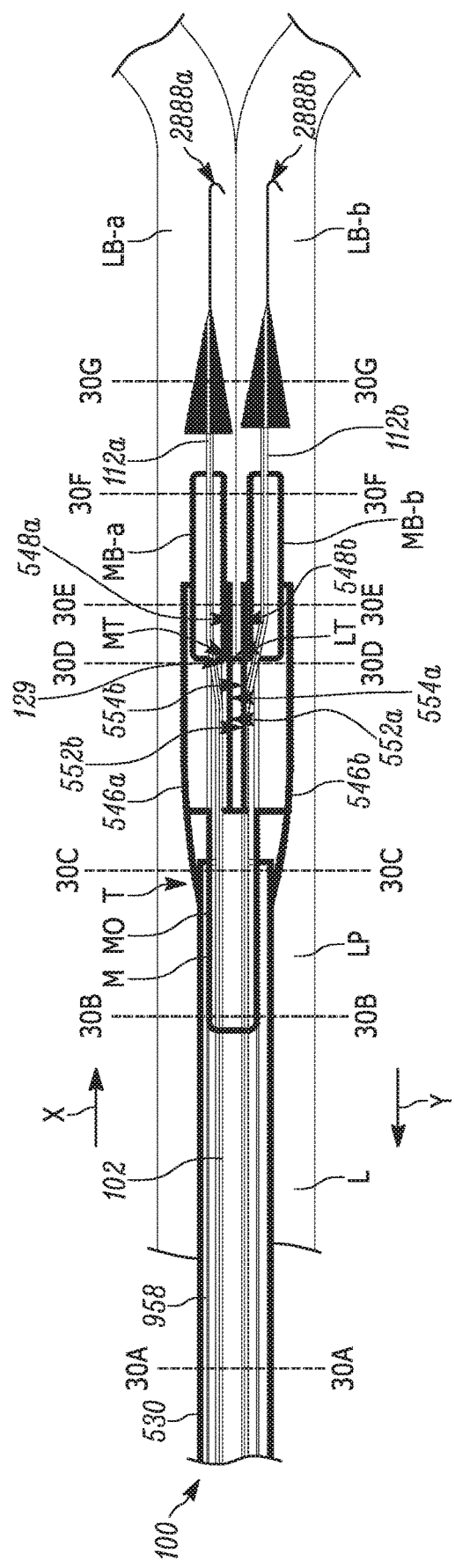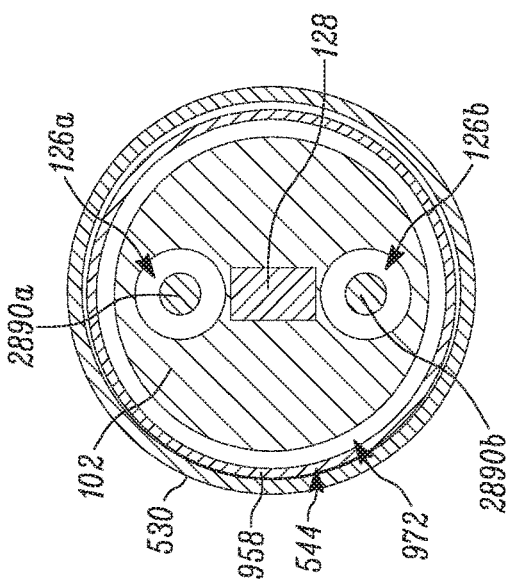

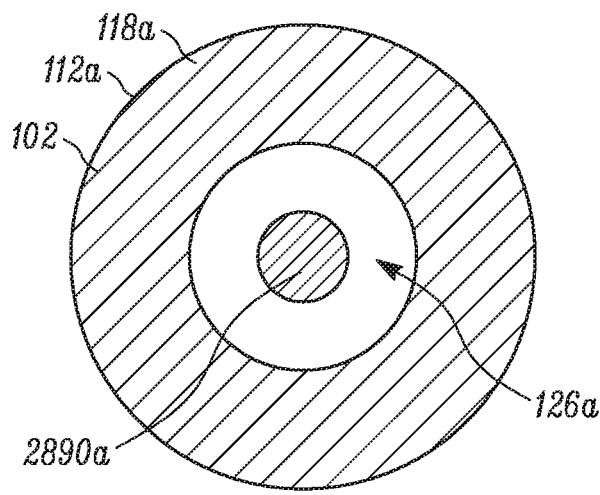
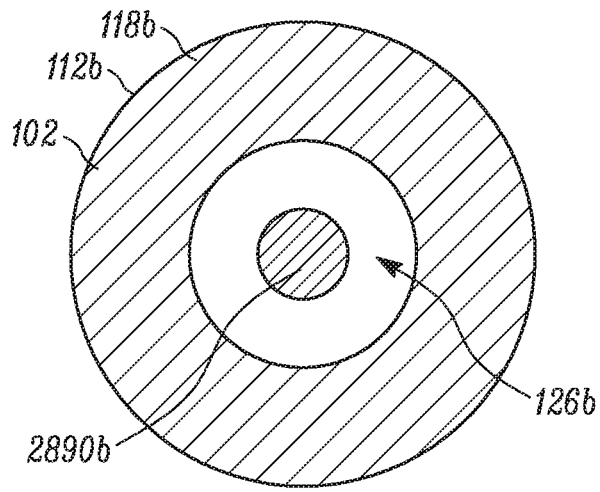
FIG. 30G

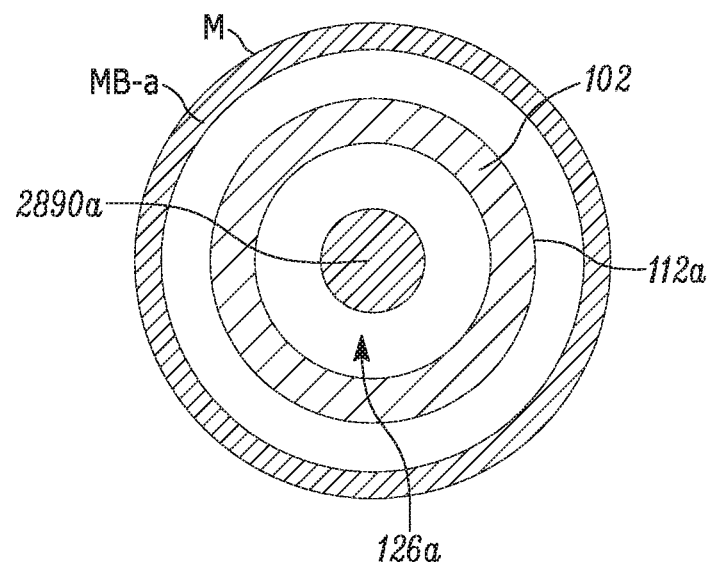
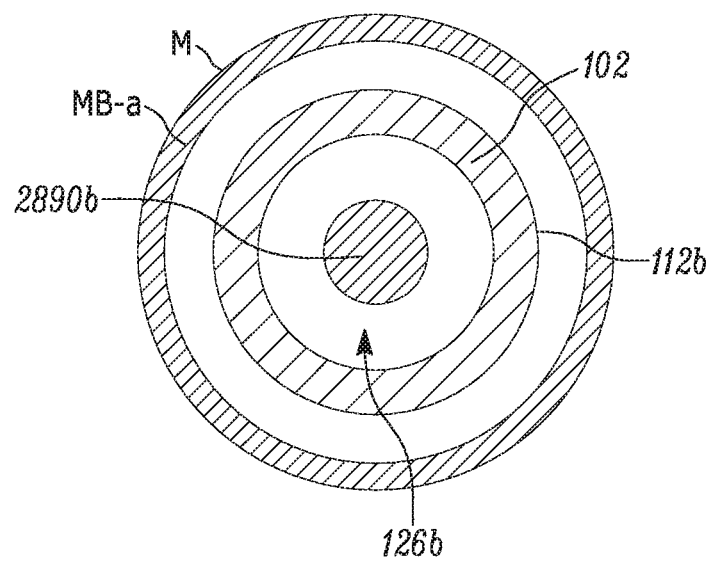
FIG. 31F

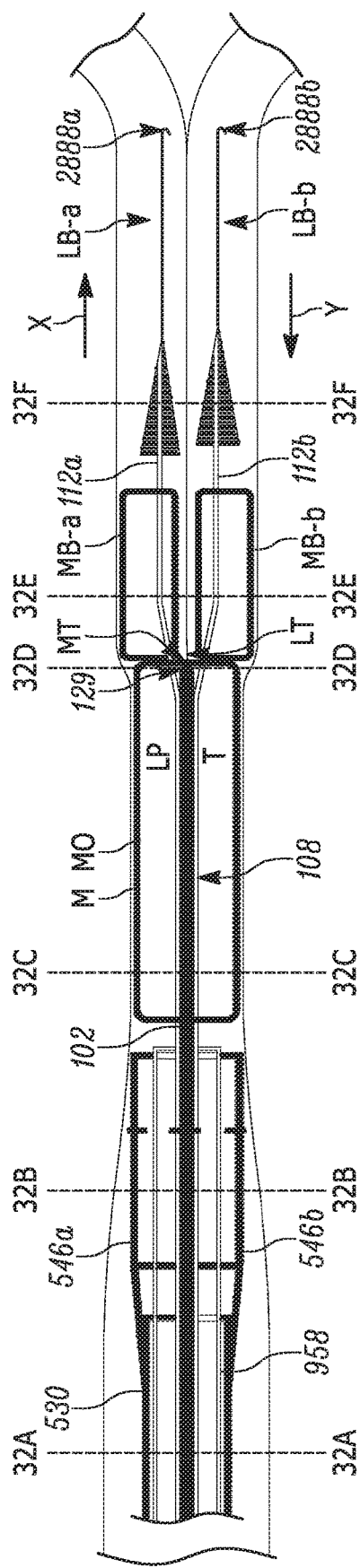
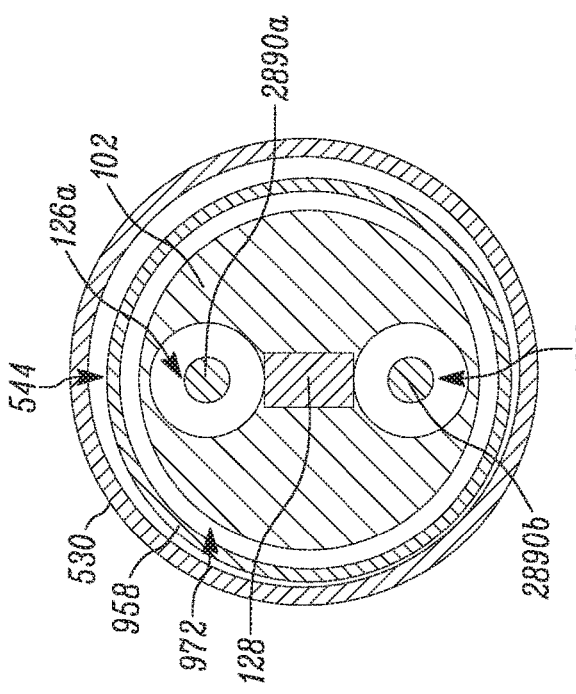
FIG. 32
FIG. 32A

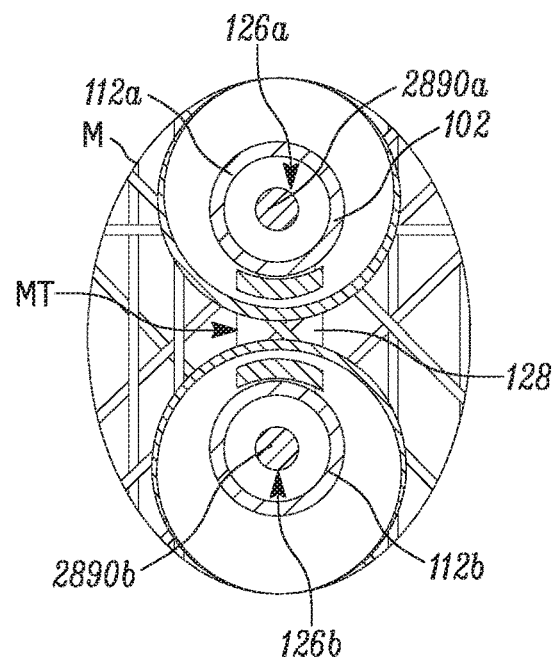
FIG. 32D
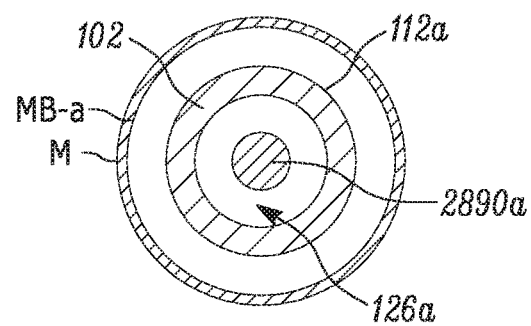
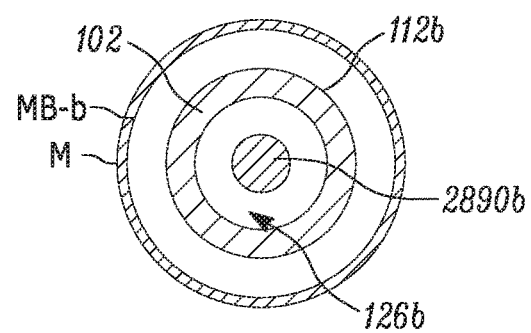
FIG. 32E

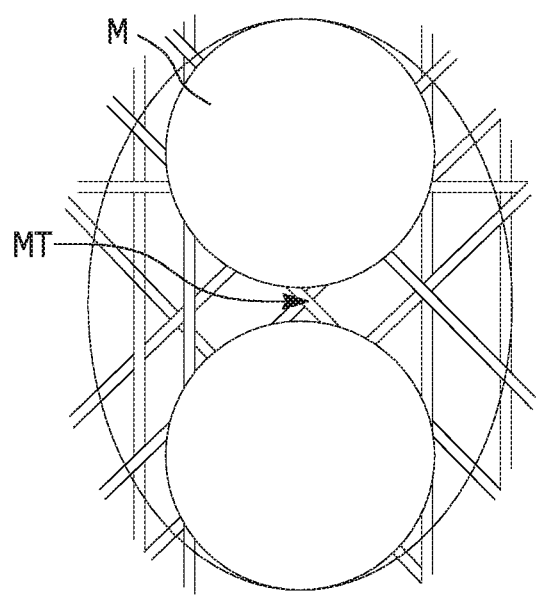
FIG. 33B
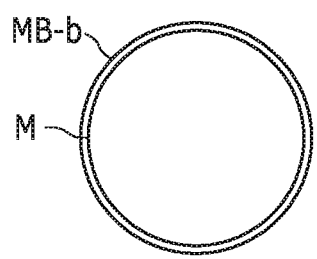
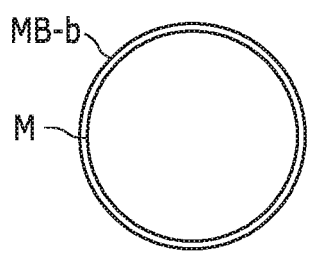
FIG. 33C

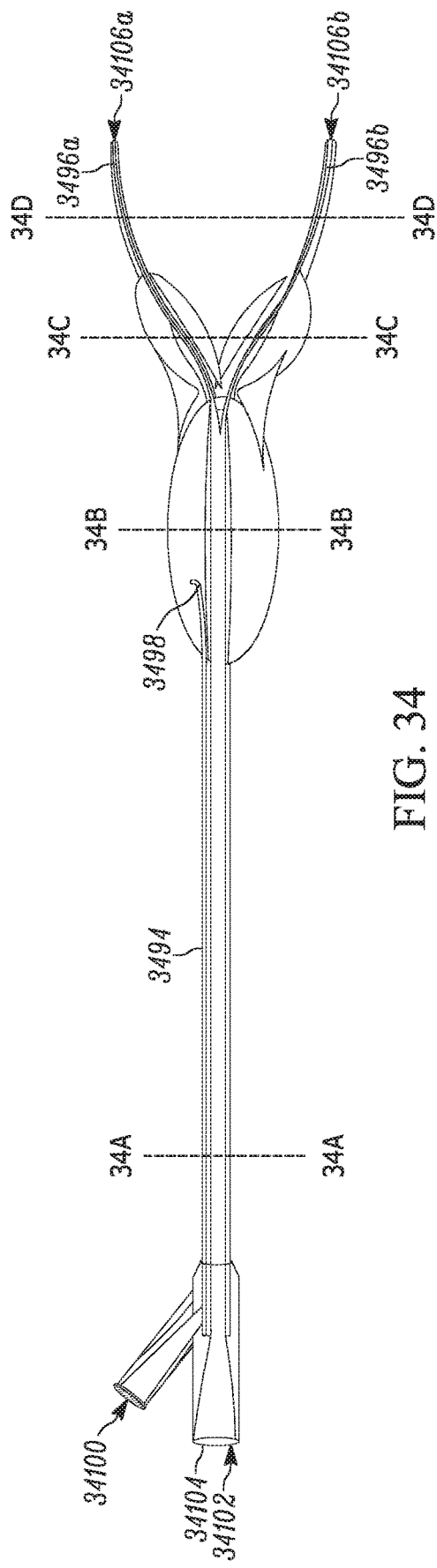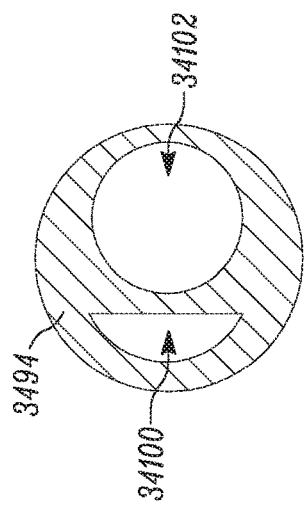
FIG. 34
FIG. 34A

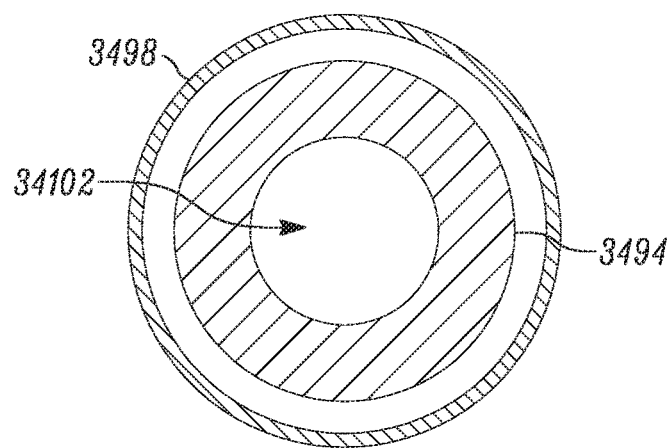
FIG. 34B
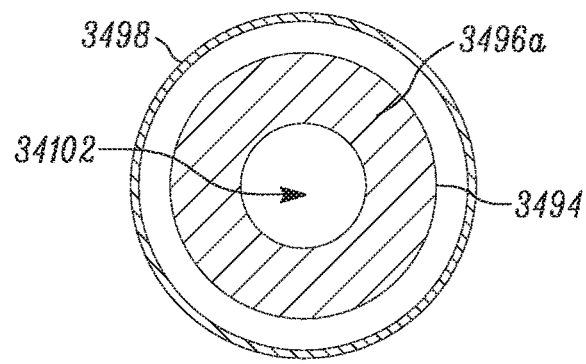
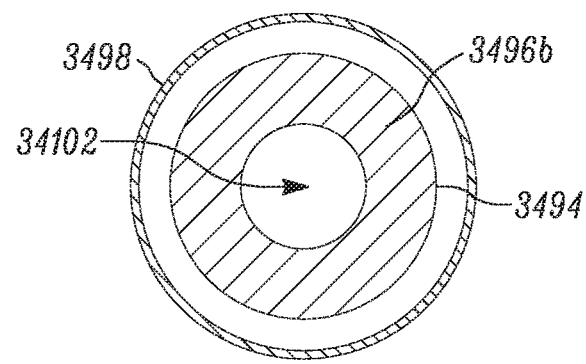
FIG. 34C

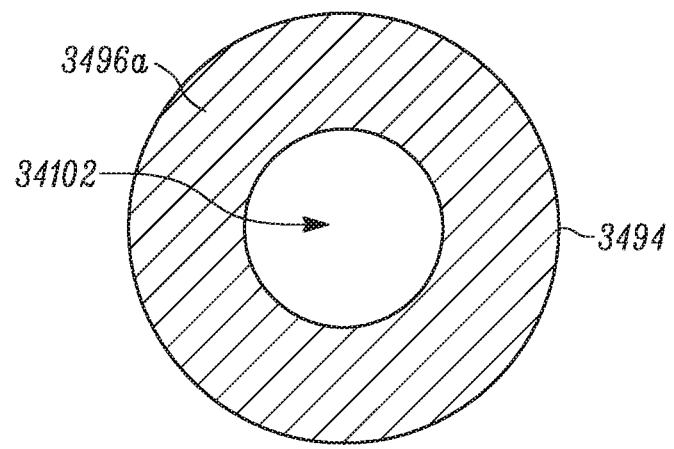
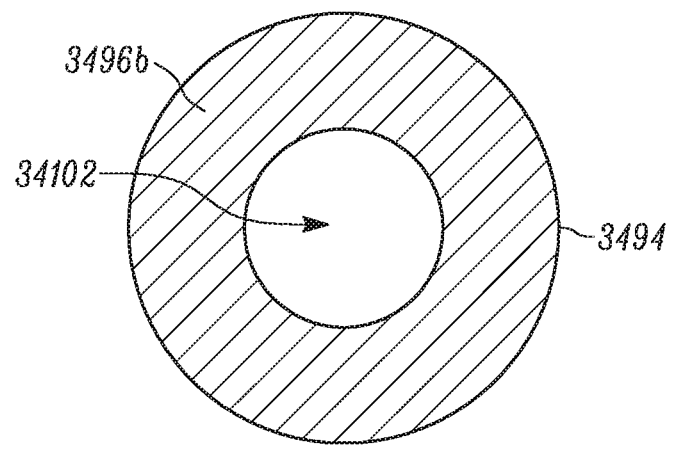
FIG. 34D

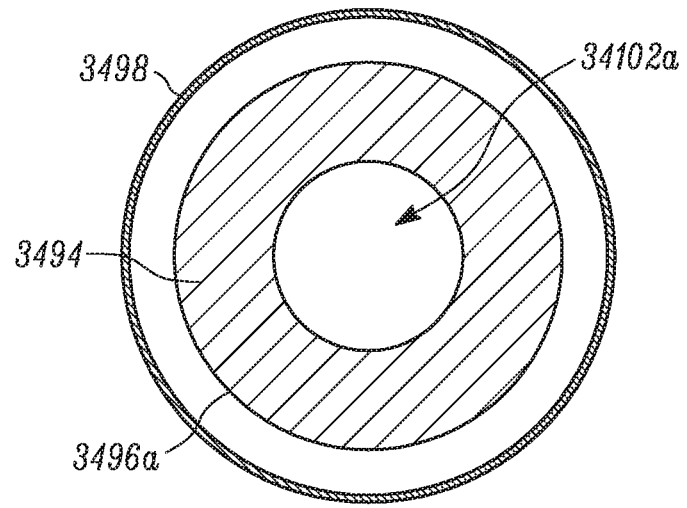
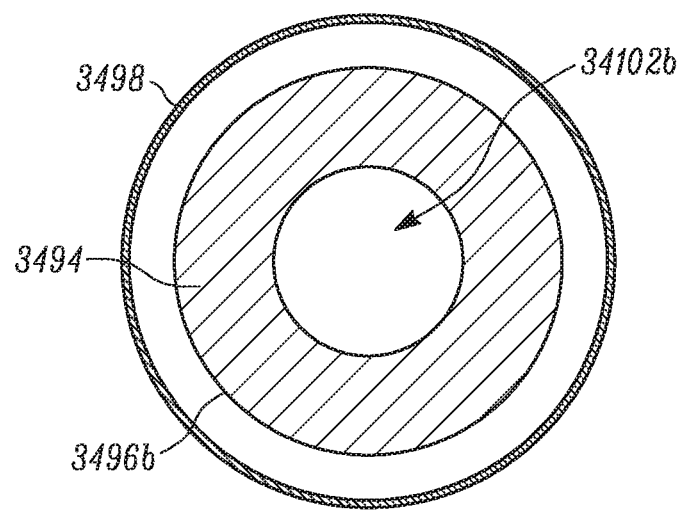
FIG. 35C

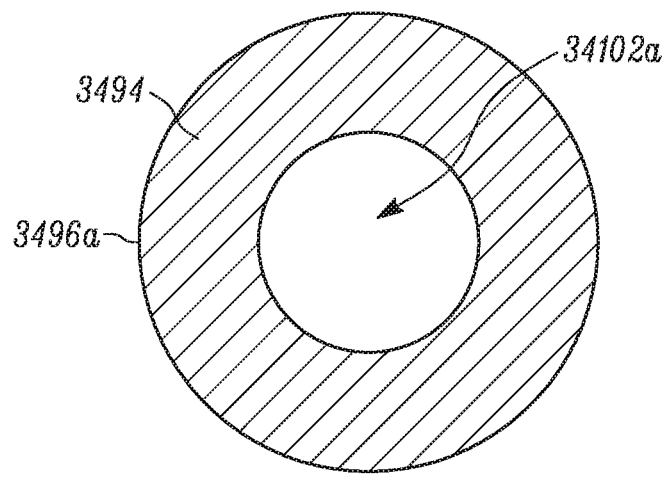
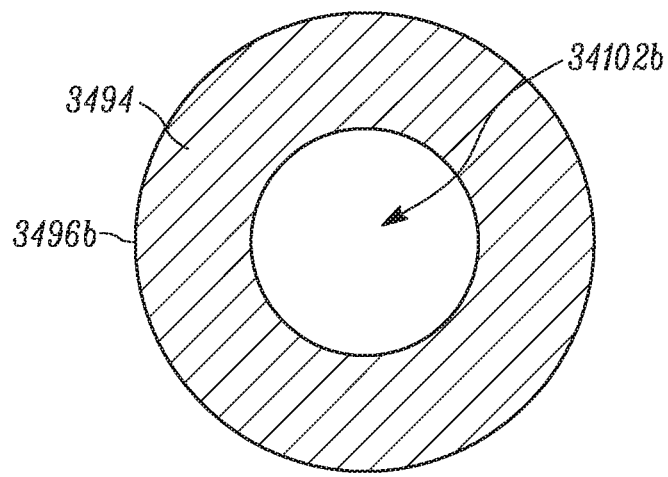
FIG. 35D

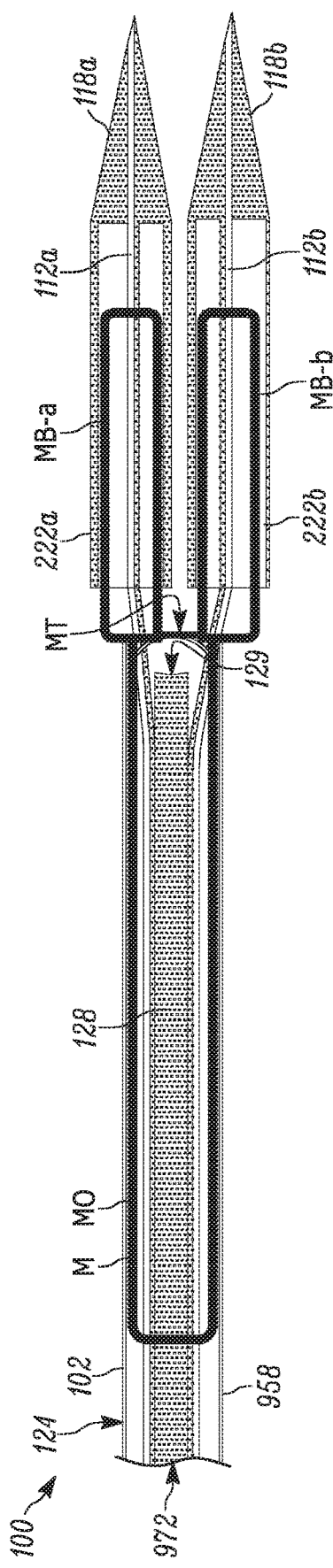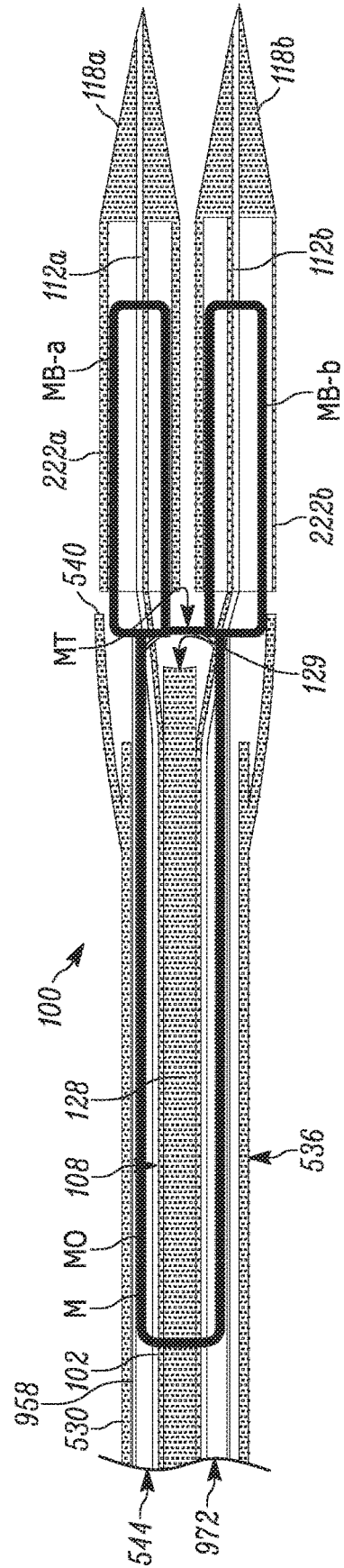

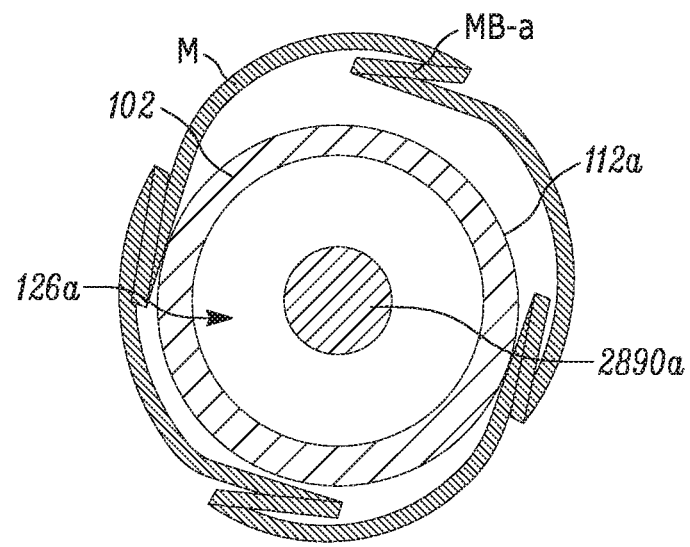
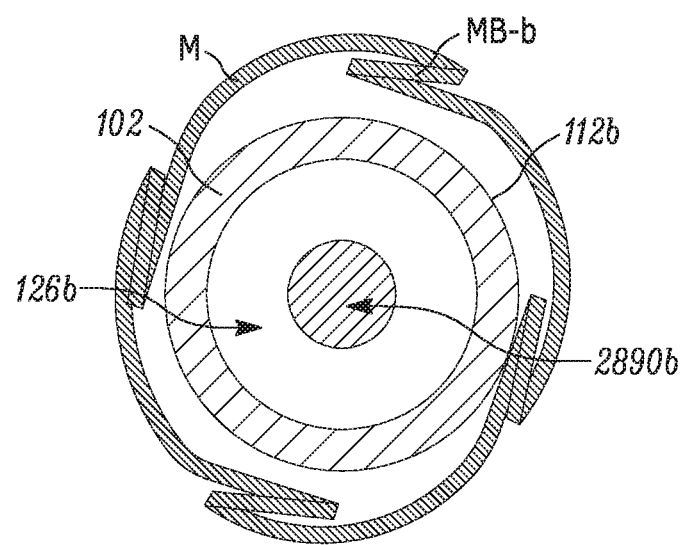
FIG. 42E

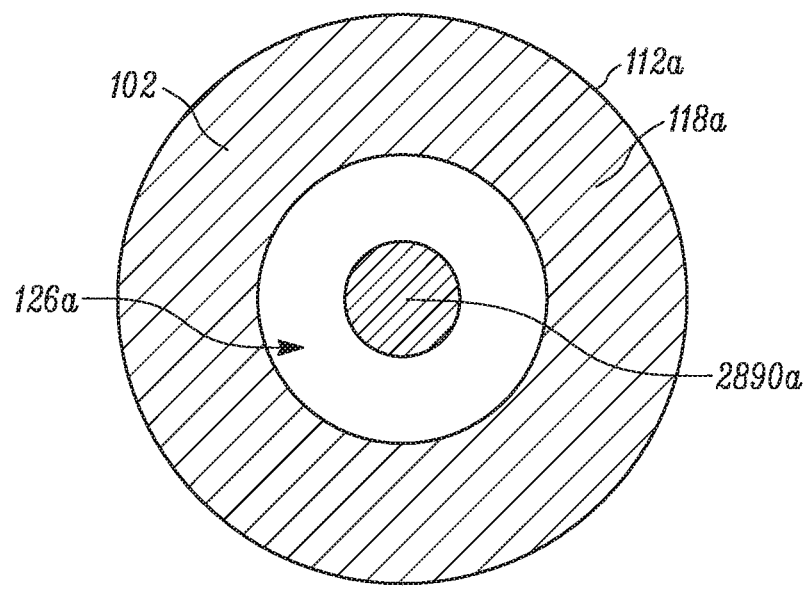
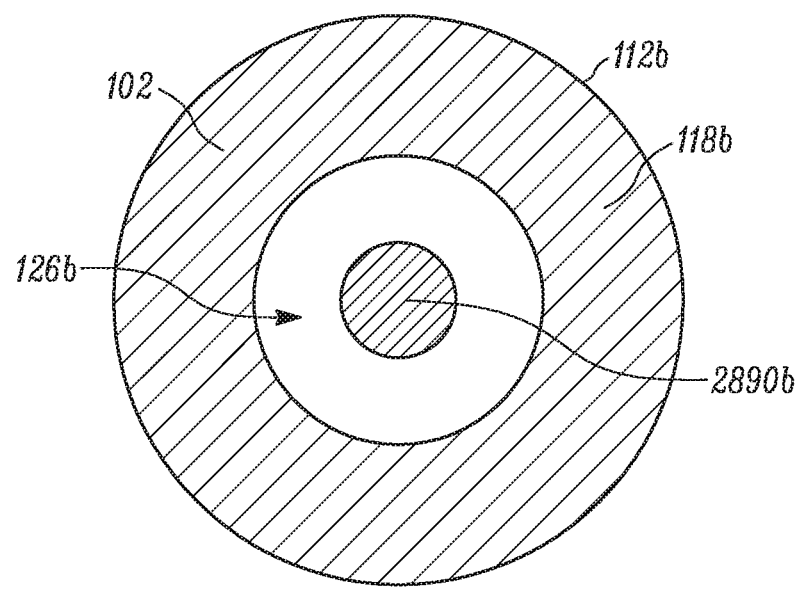
FIG. 42H

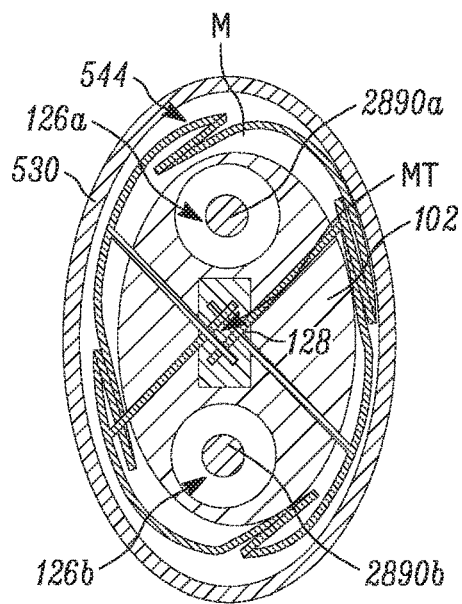
FIG. 43D
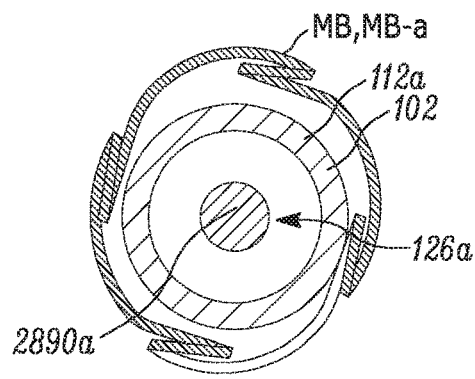
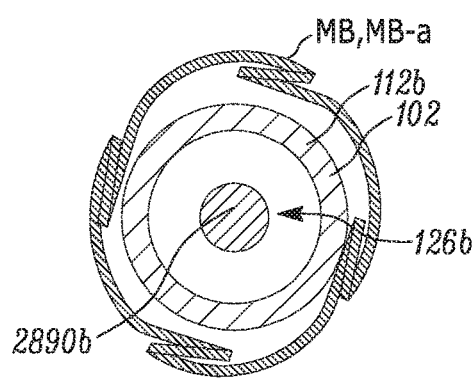
FIG. 43E

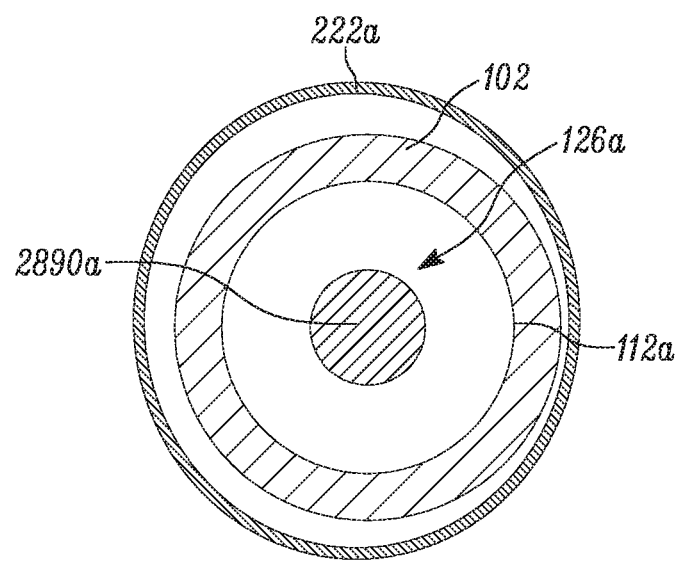
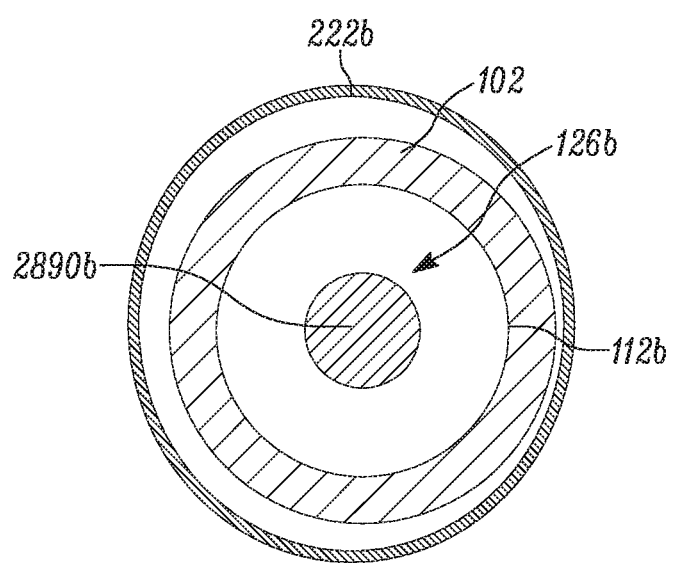
FIG. 43G

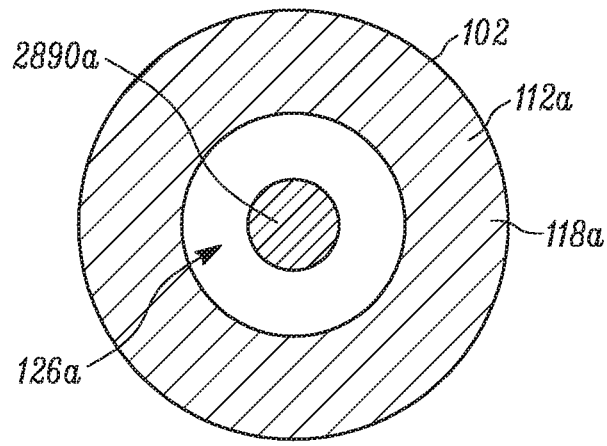
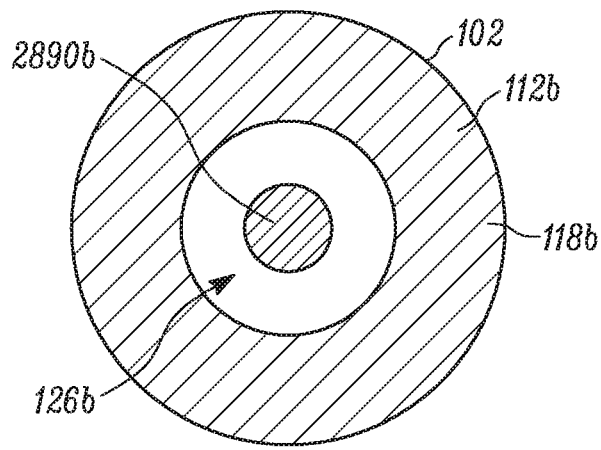
FIG. 44F

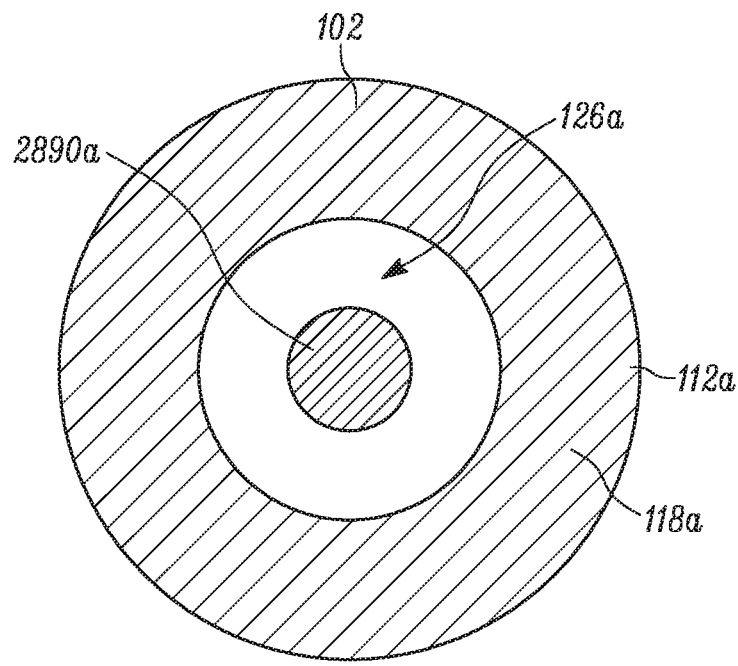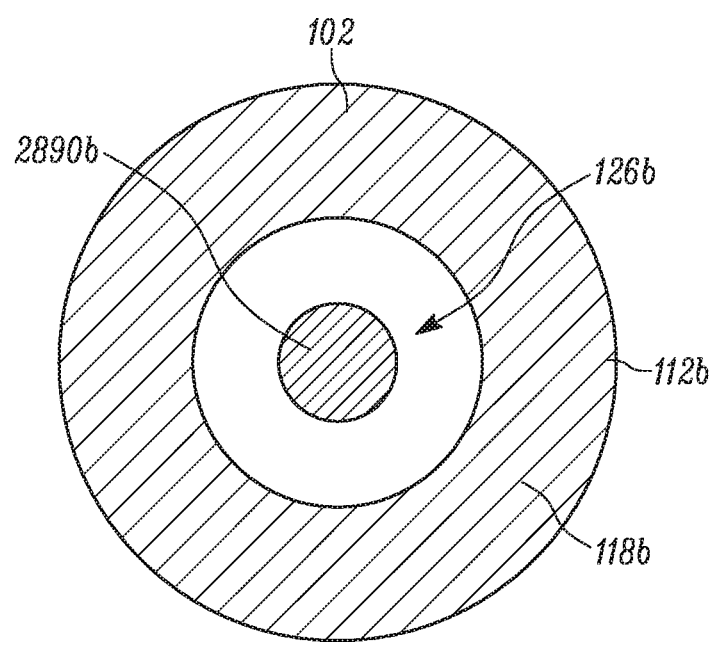
FIG. 45F

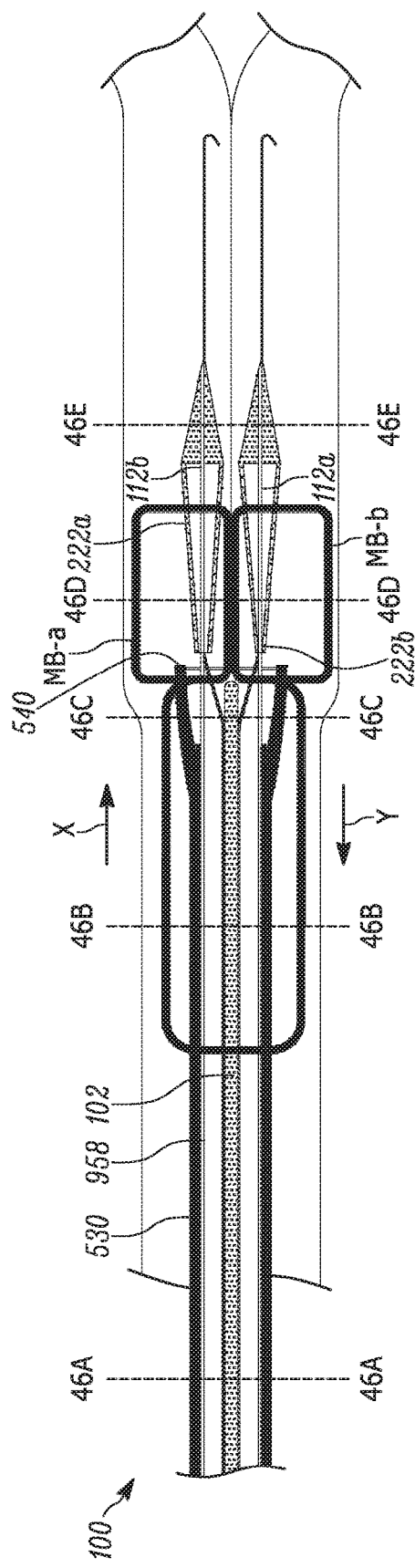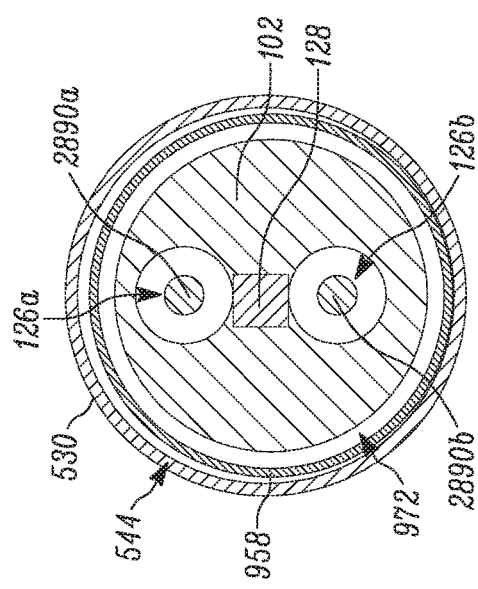
FIG. 46
FIG. 46A

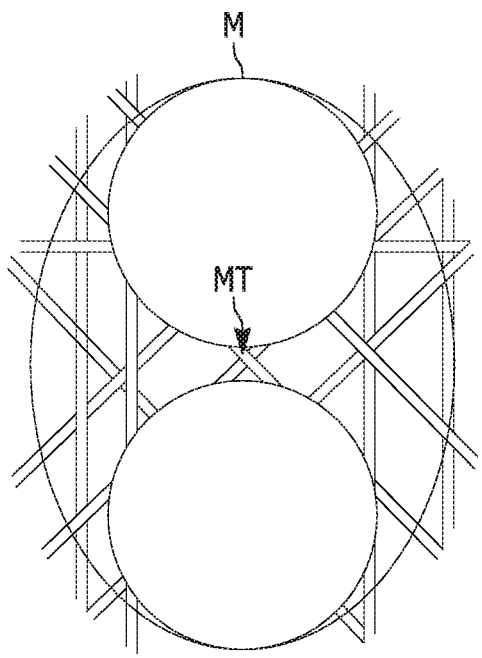
FIG. 47B
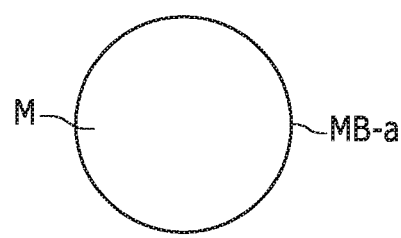
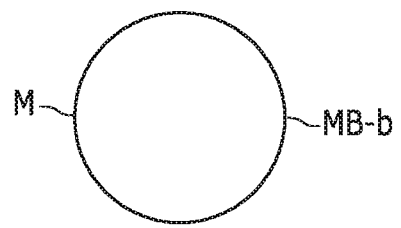
FIG. 47C

BIFURCATED IMPLANT DELIVERY SYSTEM

RELATED APPLICATION

This application is a national phase application of and claims priority from PCT International Patent Application PCT/US2018/021731, filed Mar. 9, 2018, which claims priority from U.S. Provisional Application No. 62/469,566, filed 10 Mar. 2017 and entitled SELF EXPANDING BIFURCATION STENT DELIVERY SYSTEMS AND BIFURCATED BALLOONS. The subject matter of each of the aforementioned applications is hereby incorporated by reference in its entirety.

TECHNICAL FIELD

This disclosure relates to apparatuses and methods for use of a bifurcated implant delivery system and, more particularly, to a method and device for deploying a bifurcated expandable implant in a patient lumen.

BACKGROUND

It is often desirable to use multiple guidewires in various medical procedures involving diseased bifurcated patient lumens. For example, when utilizing stent deployment devices within bifurcated lumens, a first guidewire would be used to access a first lumen branch while a second guidewire would be used to access a second lumen branch. At least one stent may be collapsed and inserted within a delivery device, such as a catheter. The delivery device may be advanced along the respective guidewires to the diseased portion of the patient lumen. Once at the desired position for stent deployment in the bifurcated patient lumen, the stent may be deployed from the delivery device and expanded.

SUMMARY

In an aspect, a bifurcated implant delivery system is provided. A shaft has a shaft proximal end having at least two shaft proximal openings. A shaft distal end has at least two shaft branches longitudinally extending from a shaft body distal end. Each of the shaft branches has a shaft open tip. A shaft body longitudinally extends between the shaft proximal end and the shaft distal end. The shaft has at least one shaft lumen. The at least one shaft lumen longitudinally extends between a respective shaft proximal opening and at least one respective shaft open tip. A reinforcing element longitudinally extends from the shaft body distal end. An outer sheath has an outer sheath proximal end having an outer sheath proximal opening. An outer sheath distal end has at least one outer sheath open tip. An outer sheath lumen longitudinally extends between the outer sheath proximal opening and the at least one outer sheath open tip. The outer sheath lumen is for selectively holding at least a portion of the shaft and a bifurcated expandable implant therein.

In an aspect, a method for deploying a bifurcated expandable implant in a patient lumen is provided. A bifurcated implant delivery system is provided. A shaft has a shaft proximal end having at least two shaft proximal openings. A shaft distal end has at least two shaft branches longitudinally extending from a shaft body distal end. Each of the shaft branches has a shaft open tip. A shaft body longitudinally extends between the shaft proximal end and the shaft distal end. The shaft has at least one shaft lumen. The at least one shaft lumen longitudinally extends between a respective shaft proximal opening and at least one respective shaft open tip. A reinforcing element longitudinally extends from the shaft body distal end. An outer sheath has an outer sheath proximal end having an outer sheath proximal opening. An outer sheath distal end has at least one outer sheath open tip. An outer sheath lumen longitudinally extends between the outer sheath proximal opening and the at least one outer sheath open tip. At least one bifurcated expandable implant is provided having an expandable implant body, at least two expandable implant branches, and an expandable implant transition portion longitudinally between the expandable implant body and the at least two expandable implant branches. At least one collapsed expandable implant is mounted circumferentially on the shaft outer surface with the expandable implant body circumferentially mounted on at least a portion of the shaft body, each of the expandable implant branches circumferentially mounted on a respective shaft branch. At least a portion of the collapsed expandable implant and at least a portion of the shaft are collectively inserted into at least a portion of the outer sheath lumen. At least two guidewires are inserted into a target patient tissue site in a patient lumen with each guidewire distal end of the at least two guidewires being positioned in a respective patient lumen branch. Each guidewire proximal end of the at least two guidewires are directed through the at least one shaft lumen. The implant delivery system is directed to the target patient tissue site along the at least two guidewires. The implant delivery system is positioned at the target patient tissue site with at least a portion of the outer sheath, at least a portion of the shaft body, and at least a portion of the expandable implant body being positioned in a patient lumen main portion; at least a portion of each shaft branch and at least a portion of each expandable implant branch being positioned in a respective patient lumen branch; and at least a portion of the expandable implant transition portion being positioned at a patient lumen transition portion. The shaft is positioned with a reinforcing element distal end at least partially contacting at least a portion of the expandable implant transition portion, and with at least a portion of the reinforcing element distal end being at the patient lumen transition portion. With the implant delivery system positioned at the target patient tissue site, at least a portion of the expandable implant is exposed by urging the outer sheath in the longitudinally proximal direction, while maintaining each of the at least two guidewires, the expandable implant body, and the shaft body at the patient lumen main portion; the guidewire distal ends, the expandable implant branches, and the shaft branches at the respective patient lumen branches, and the reinforcing element distal end and the expandable implant transition portion at the patient lumen transition portion. The contact between the expandable implant transition portion and the reinforcing element distal end at least partially maintains the expandable implant transition portion at the patient lumen transition portion while the outer sheath is urged in the proximal direction. With the at least a portion of the expandable implant exposed, the properties of the expandable implant are utilized to move the exposed portion of the expandable implant toward an expanded condition.

BRIEF DESCRIPTION OF THE DRAWINGS

For a better understanding, reference may be made to the accompanying drawings, in which:

FIGS. 1a-d depict cross-sectional views of the aspect of FIG. 1;

FIGS. 3-4 depict a schematic side view of the aspect of FIG. 2, in an example sequence of operation;

FIGS. 3a-b depict cross-sectional views of the aspect of FIG. 3;

FIGS. 4a-b depict cross-sectional views of the aspect of FIG. 4;

FIG. 5 is a schematic side view of an element of an implant delivery system according to one aspect of the present invention;

FIG. 7 is a schematic bottom view of the aspect of FIG. 5, including a second option for a component;

FIG. 7a depicts a cross-sectional view of the aspect of FIG. 7;

FIG. 8 is a schematic side view of the aspect of FIG. 5, including a third option for a component;

FIGS. 8a-b depict cross-sectional views of the aspect of FIG. 8;

FIGS. 20-36 illustrate an example sequence of operation of a portion of the bifurcated implant delivery system in a first example use configuration, including selected cross-sectional views; and FIGS. 37-48 illustrate an example sequence of operation of a portion of the implant delivery system in a second example use configuration, including selected cross-sectional views.

DESCRIPTION OF ASPECTS OF THE DISCLOSURE

Unless defined otherwise, all technical and scientific terms used herein have the same meaning as is commonly understood by one of skill in the art to which the present disclosure pertains.

As used herein, the term "patient" may refer to any warm-blooded organism including, but not limited to, human beings, pigs, rats, mice, dogs, goats, sheep, horses, monkeys, apes, rabbits, cattle, farm animals, livestock, birds, etc.

As used herein, the term "user" may be used interchangeably to refer to an individual who prepares for, assists, and/or performs a procedure.

As used herein, the singular forms "a," "an" and "the" may include the plural forms as well, unless the context clearly indicates otherwise. It will be further understood that the terms "comprises" and/or "comprising," as used herein, may specify the presence of stated features, steps, operations, elements, and/or components, but do not preclude the presence or addition of one or more other features, steps, operations, elements, components, and/or groups thereof.

As used herein, the term "and/or" may include any and all combinations of one or more of the associated listed items.

As used herein, phrases such as "between X and Y" may be interpreted to include X and Y.

It will be understood that when an element is referred to as being "on," "contacting," etc., another element, it may be directly on or contacting the other element or intervening elements may also be present. It will also be appreciated by those of skill in the art that references to a structure or feature that is disposed "adjacent" another feature may not have portions that overlap or underlie the adjacent feature.

Spatially relative terms, such as "over" and the like, may be used herein for ease of description to describe one element or feature's relationship to another element(s) or feature(s) as illustrated in the Figures. It will be understood that the spatially relative terms may encompass different orientations of a device in use or operation, in addition to the orientation depicted in the Figures. For example, if a device in the Figures is inverted, elements described as being "over" other elements or features would then be oriented "under" than the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or Figures unless specifically indicated otherwise.

The invention comprises, consists of, or consists essentially of the following features, in any combination.

Figure 1:
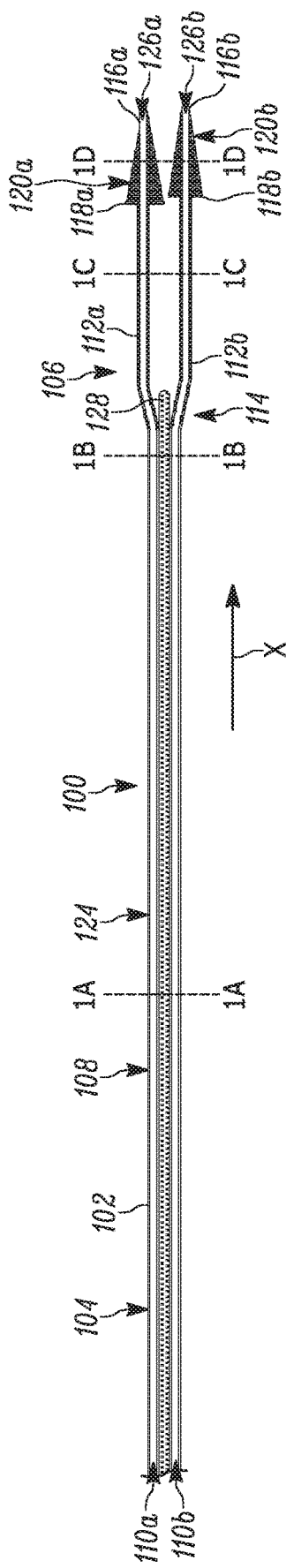
FIG. 1 is a schematic side view of an element of a bifurcated implant delivery system according to one aspect of the present invention, including a first option for a component.
Figure 1A:
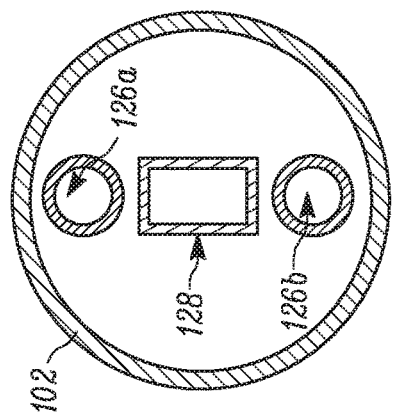
Figure 1D:
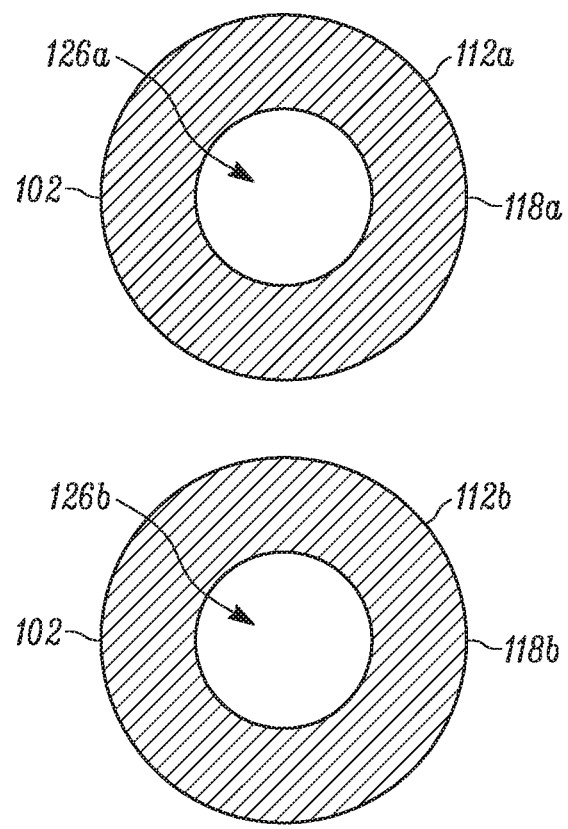

An implant delivery system 100 is provided. The implant delivery system 100 may include a shaft 102 having one of any number of alternate configurations, some of which will be discussed below. As shown in FIG. 1, the shaft 102 has a shaft proximal end 104, a shaft distal end 106, and a shaft body 108 longitudinally extending between the shaft proximal and distal ends 104, 106. The term "longitudinal" is used herein to indicate a substantially horizontal direction, in the orientation of FIG. 1. The shaft proximal end 104 may have at least one shaft proximal opening 110 (shown here as shaft proximal openings 110a and 110b). The shaft distal end 106 may have at least two shaft branches 112 (shown here as shaft branches 112a and 112b) that longitudinally extend from a shaft body distal end 114. Each of the shaft branches 112a, 112b has a shaft open tip 116 (shown here as shaft open tips 116a and 116b) and may have a nosecone 118 (shown here as nosecones 118a and 118b) at a respective shaft branch distal end 120 (shown here as shaft branch distal ends 120a and 120b). A "nosecone," as used herein, is a structure resembling a cone, or, in other words, resembling a solid bounded by a circular or other closed plane base and the surface formed by line segments joining every point of the boundary of the base to a common vertex.

Each of the nosecones 118a, 118b may point, or narrow, in a longitudinally distal direction (shown as an arrow "X" in FIG. 1). Each of the nosecones 118a, 118b may be configured to substantially prevent the egress of a bifurcated expandable implant M mounted circumferentially on the shaft 102 from a desired position on the shaft 102, such as on at least one of the shaft body 108 and the at least two shaft branches 112a, 112b. The term "circumferentially" is defined herein as at least partially surrounding the external boundary or surface of a figure or object. The bifurcated expandable implant M may be a bifurcated stent, a bifurcated stent-graft, a bifurcated embolization plug, a bifurcated shunt closure device, any bifurcated self-expandable device, any other bifurcated expandable device, or any combination thereof. Each of the nosecones 118a, 118b may also, or instead, be used for a smooth atraumatic transition of the implant delivery system 100 into a target patient tissue site T of a patient lumen L.

Figure 2:
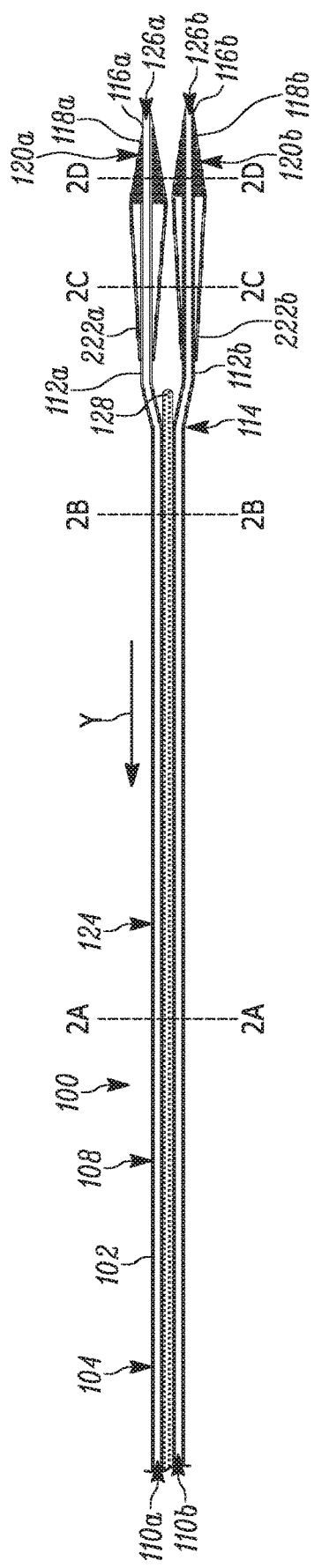
FIG. 2 is a schematic side view of the aspect of FIG. 1, including a second option for a component.
Figure 2A:
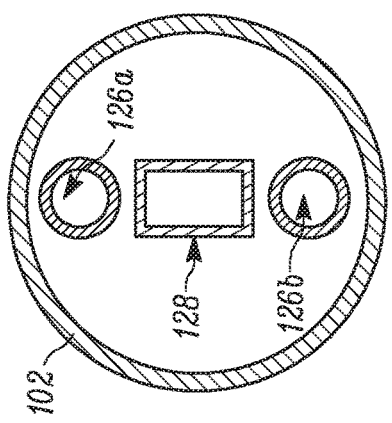
FIGS. 2a-d depict cross-sectional views of the aspect of FIG. 2.
Figure 2B:
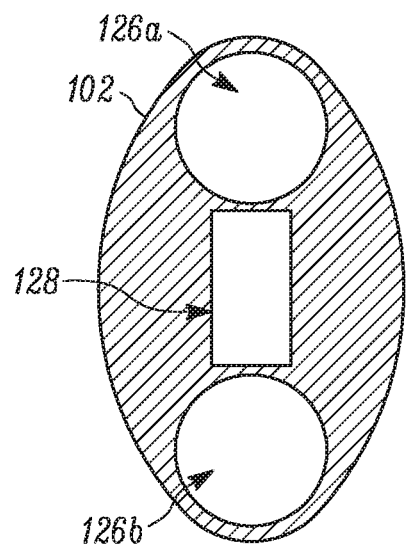
Figure 2C:
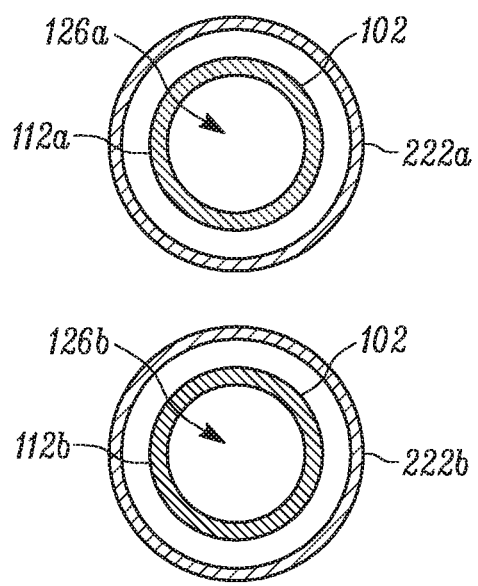
Figure 2D:
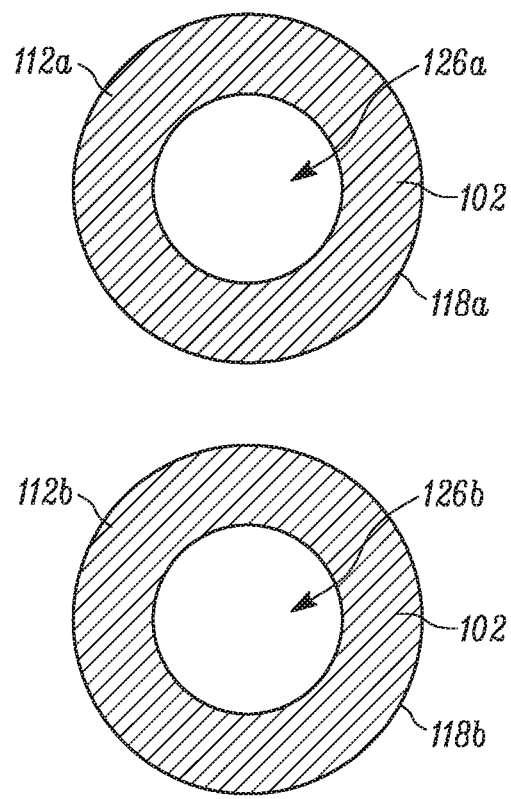

As shown in FIGS. 2-4, each of the nosecones 118a, 118b may have at least one elastic skirt 222 (shown here as elastic skirts 222a and 222b) that longitudinally extends in the proximal direction (shown as an arrow "Y" in FIGS. 2-4). Each of the elastic skirts 222a, 222b may be for at least partially selectively restricting at least a portion of a respective expandable implant branch MB (shown here as expandable implant branches MB-a and MB-b) from fully expanding, and/or moving toward an expanded condition, from a collapsed condition when the bifurcated expandable implant M is operatively joined to the shaft 102, as will be discussed in more detail below. Each of the elastic skirts 222a, 222b is capable of moving between a collapsed condition (FIG. 3) and an expanded condition (FIG. 4).

As shown in FIGS. 1-4, the shaft 102 may have a shaft outer surface 124 and at least one shaft lumen 126 (shown here as shaft lumens 126a and 126b). At least a portion of the shaft outer surface 124 may be configured for selectively circumferentially mounting the bifurcated expandable implant M thereon, as will be described below. In the case of a shaft 102 having one shaft lumen 126, the shaft lumen 126 may longitudinally extend between a respective shaft proximal opening 110 and each of the shaft open tips 116a, 116b. In the case of a shaft 102 having at least two shaft lumens 126a, 126b, each of the shaft lumens 126a, 126b may longitudinally extend between a respective shaft proximal opening 110a, 110b and a respective shaft open tip 116a, 116b. Instead of extending to a respective shaft proximal opening 110a, 110b, each of the shaft lumens 126a, 126b of a shaft 102 having at least two shaft lumens 126a, 126b may extend between a respective shaft open tip 116a, 116b and at least one shaft proximal opening (shown here as two shaft proximal openings 110a and 110b), which may be common/shared or individual per shaft lumen.

The shaft 102 may have a reinforcing element 128 that longitudinally extends from the shaft body distal end 114. The reinforcing element 128 may both longitudinally extend between the shaft proximal end 104 and the shaft body distal end 114, and longitudinally extend from the shaft body distal end 114. When a bifurcated expandable implant M is operatively joined to the shaft 102, at least a portion of an expandable implant transition portion MT may at least partially contact a reinforcing element distal end 129. The contact between the expandable implant transition portion MT and the reinforcing element distal end 129 may at least partially maintain the expandable implant transition portion MT at a patient lumen transition portion LT during operation of the implant delivery system 100, as will be described below. FIGS. 1 a-d, 2a-d, 3a-b, and 4a-b depict cross-sectional views of various points along the shaft 102, to show the structural features of the shaft 102, as depicted in FIGS. 1, 2, 3, and 4, respectively.

The implant delivery system 100 may include an outer sheath 530 having one of any number of alternate configurations, some of which will be discussed below. As shown in FIG. 5, the outer sheath 530 has an outer sheath proximal end 532, an outer sheath distal end 534, and an outer sheath body 536 longitudinally extending between the outer sheath proximal and distal ends 532, 534. The outer sheath proximal end 532 may have an outer sheath proximal opening 538. The outer sheath distal end 534 may have at least one outer sheath open tip 540 (shown here as outer sheath open tips 540a and 540b). The outer sheath 530 may have an outer sheath outer surface 542 and an outer sheath lumen 544. The outer sheath lumen 544 may longitudinally extend between the outer sheath proximal opening 538 and the at least one outer sheath open tip 540a, 540b. The outer sheath lumen 544 is at least partially configured for selectively holding at least a portion of the shaft 102 and a bifurcated expandable implant M therein, as will be described below.

Figure 6:
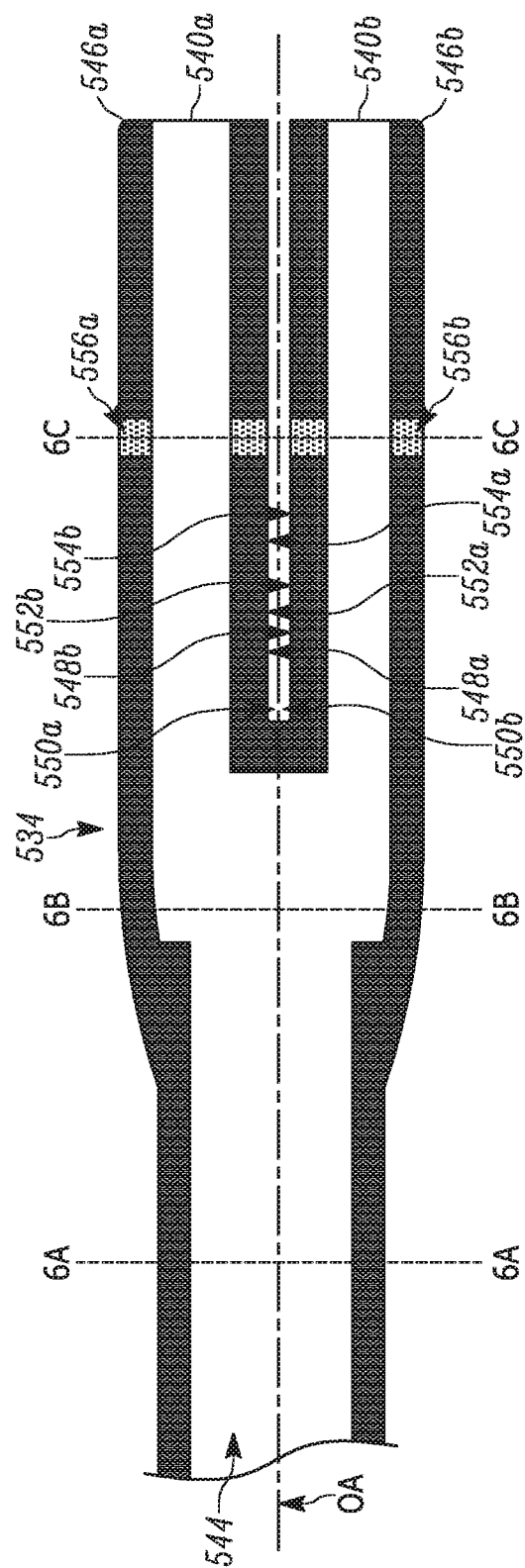
FIG. 6 is a schematic side view of the aspect of FIG. 5, including a first option for a component.

As shown in FIGS. 5-6, the outer sheath distal end 534 may have at least two outer sheath branches 546 (shown here as outer sheath branches 546a and 546b). The number of outer sheath branches 546a, 546b may directly correspond to at least one of the number of shaft branches 112a, 112b, the number of expandable implant branches MB-a, MB-b of a bifurcated expandable implant M, and the number of patient lumen branches LB (shown here as patient lumen branches LB-a and LB-b) in a bifurcated patient lumen L. Each of the outer sheath branches 546a, 546b may have an outer sheath open tip 540a, 540b. When the outer sheath 530 has at least two outer sheath branches 546a, 546b, the outer sheath lumen 544 longitudinally extends between the outer sheath proximal opening 538 and each of the outer sheath open tips 540a, 540b. In such case, the outer sheath lumen 544 is configured to at least partially selectively prevent at least one of an expandable implant body MO and expandable implant branches MB-a, MB-b from expanding from a collapsed condition when the bifurcated expandable implant M is at least partially disposed within the outer sheath lumen 544.

Figure 6A:
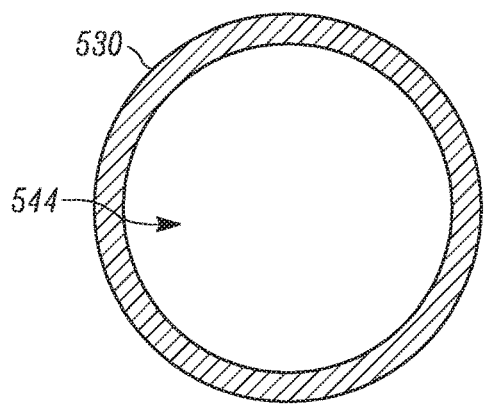
FIGS. 6a-c depict cross-sectional views of the aspect of FIG. 6.
Figure 6B:
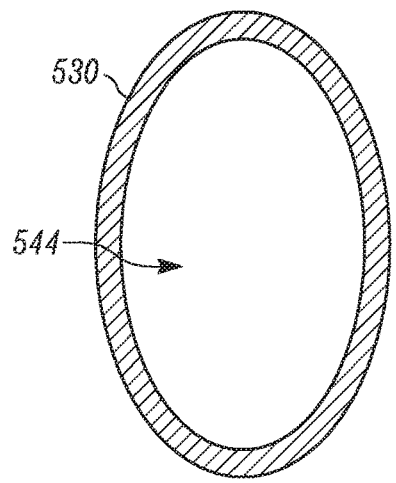
Figure 6C:
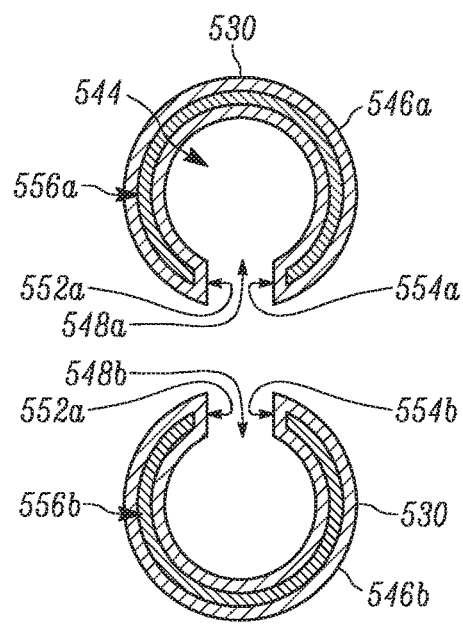

Each of the outer sheath branches 546a, 546b may have an outer sheath branch open slit 548 (shown here as outer sheath branch open slits 548a and 548b). Each of the outer sheath branch open slits 548a, 548b may longitudinally extend between a respective outer sheath branch proximal end 550 (shown here as outer sheath branch proximal ends 550a and 550b) and a respective outer sheath open tip 540a, 540b. Each of the outer sheath branch open slits 548a, 548b may laterally face toward an outer sheath longitudinal axis OL. Each outer sheath branch open slit 548a, 548b has an outer sheath branch open slit first surface 552 (shown here as outer sheath branch open slit first surfaces 552a and 552b) and an outer sheath branch open slit second surface 554 (shown here as outer sheath branch open slit second surfaces 554a and 554b). The outer sheath branch open slit first surface 552a, 552b may oppositely face and circumferentially abut the outer sheath branch open slit second surface 554a, 554b. The outer sheath branch open slit first surface 552a, 552b and the outer sheath branch open slit second surface 554a, 554b may be selectively elastically separable. That is, a force may be applied to separate the outer sheath branch open slit first surface 552a, 552b and the outer sheath branch open slit second surface 554a, 554b, as that the outer sheath branch open slit first surface 552a, 552b will no longer be abutting the outer sheath branch open slit second surface 554a, 554b. However, upon the removal of the separating force, the outer sheath branch open slit first surface 552a, 552b and the outer sheath branch open slit second surface 554a, 554b will return to their original abutting position due to the elastic nature of the material forming the outer sheath branch open slit first surface 552a, 552b and the outer sheath branch open slit second surface 554a, 554b. Alternatively, instead of abutting, the outer sheath branch open slit first surface 552a, 552b and the outer sheath branch open slit second surface 554a, 554b may laterally overlap to provide a labyrinth-type seal (not shown). FIGS. 6a-c depict cross-sectional views of various points along the outer sheath 530 having the at least two outer sheath branches 546a, 546b with the outer sheath branch open slits 548a, 548b, to show the structural features of the outer sheath 530 having the at least two outer sheath branches 546a, 546b with the outer sheath branch open slits 548a, 548b, as depicted in FIG. 6.

As shown in FIGS. 7-7a, instead of abutting and/or overlapping, at least a portion of the outer sheath branch open slit first surface 552a, 552b may be radially spaced from at least a portion of the outer sheath branch open slit second surface 554a, 554b. The term "radial" is used herein to indicate a direction substantially perpendicular to the "longitudinal" direction, and is shown via arrows "R" in FIG. 7a extending toward a longitudinal axis LA, in the orientation of FIG. 7a. When the outer sheath branch open slit 548a, 548b has radially spaced outer sheath branch open slit first and second surfaces 552a, 552b, 554a, 554b, the outer sheath branch open slit first surface 552a, 552b and the outer sheath branch open slit second surface 554a, 554b may be selectively elastically separable. That is, a force may be applied to separate at least a portion of the outer sheath branch open slit first surface 552a, 552b even further apart from at least a portion of the outer sheath branch open slit second surface 554a, 554b, as that the radial spacing between at least a portion of the outer sheath branch open slit first and second surfaces 552a, 552b, 554a, 554b is larger post-separating forcing than what the radial spacing was pre-separating force. However, upon the removal of the separating force, the outer sheath branch open slit first surface 552a, 552b and the outer sheath branch open slit second surface 554a, 554b will return to their pre-separating force radial spacing due to the elastic nature of the material forming the outer sheath branch open slit first surface 552a, 552b and the outer sheath branch open slit second surface 554a, 554b.

As shown in FIG. 7, each of the outer sheath branch open slits 548a, 548b may inwardly taper between a respective outer sheath branch proximal end 550a, 550b and a respective outer open tip 540a, 540b of a respective outer sheath branch 546a, 546b. In other words, the outer sheath branch open slit first surface 552a, 552b may be spaced further apart from the outer sheath branch open slit second surface 554a, 554b at the outer sheath branch proximal end 550a, 550b than at the outer sheath open tip 540a, 540b of a respective outer sheath branch 546a, 546b. The term "taper" is defined herein as a gradual diminution of thickness, diameter, or width in an elongated object, as is shown by the gradual diminution in spacing between outer sheath branch open slit first surface 552a, 552b and the outer sheath branch open slit second surface 554a, 554b at the outer sheath branch proximal end 550a, 550b and the outer sheath branch open slit first and second surfaces 552a, 552b, 554a, 554b at the outer sheath open tip 540a, 540b in FIG. 7. The term "inward" is defined herein as a taper that becomes gradually smaller, such as shown as the gradual diminution in spacing between outer sheath branch open slit first surface 552a, 552b and the outer sheath branch open slit second surface 554a, 554b at the outer sheath branch proximal end 550a, 550b and the outer sheath branch open slit first and second surfaces 552a, 552b, 554a, 554b at the outer sheath open tip 540a, 540b in FIG. 7. Further, the inward taper, such as the taper of the outer sheath open slit 548a, 548b of FIG. 7, could include no expansion in spacing (or even an outward taper) from a respective outer sheath branch proximal end 550a, 550b to a respective outer sheath branch open tip 540a, 540b.

When each of the outer sheath branch open slits 548a, 548b inwardly taper between a respective outer sheath branch proximal end 550a, 550b and a respective outer open tip 540a, 540b of a respective outer sheath branch 546a, 546b, at least a portion of the outer sheath branch open slit first surface 552a, 552b may be radially spaced from at least a portion of the outer sheath branch open slit second surface 554a, 554b, and at least a portion of the outer sheath branch open slit first surface 552a, 552b may circumferentially abut at least a portion of the outer sheath branch open slit second surface 554a, 554b. For example, the outer sheath branch open slit first surface 552a, 552b may be radially spaced further apart from the outer sheath branch open slit second surface 554a, 554b at, and/or adjacent to, the outer sheath branch proximal end 550a, 550b than at, and/or adjacent to, the outer sheath open tip 540a, 540b of a respective outer sheath branch 546a, 546b, and the outer sheath branch open slit first surface 552a, 552b may circumferentially abut the outer sheath branch open slit second surface 554a, 554b at, and/or adjacent to, the outer sheath open tip 540a, 540b of a respective outer sheath branch 546a, 546b.

The outer sheath branch open slit first surface 552a, 552b and the outer sheath branch open slit second surface 554a, 554b of each of the tapered outer sheath branch open slits 548a, 548b may be selectively elastically separable. That is, a force may be applied to separate at least a portion of the outer sheath branch open slit first surface 552a, 552b even further apart from at least a portion of the outer sheath branch open slit second surface 554a, 554b at the radially-spaced portion of the outer sheath branch open slits 548a, 548b, as that the radial spacing between at least a portion of the outer sheath branch open slit first and second surfaces 552a, 552b, 554a, 554b is larger post-separating forcing than what the radial spacing was pre-separating force at the radially-spaced portion of the outer sheath branch open slits 548a, 548b. Additionally, the separating force may be applied to separate the outer sheath branch open slit first surface 552a, 552b and the outer sheath branch open slit second surface 554a, 554b at the abutting portion of the outer sheath branch open slits 548a, 548b, as that the outer sheath branch open slit first surface 552a, 552b will no longer be abutting the outer sheath branch open slit second surface 554a, 554b at the abutting portion of the outer sheath branch open slits 548a, 548b.

However, upon the removal of the separating force, the outer sheath branch open slit first surface 552a, 552b and the outer sheath branch open slit second surface 554a, 554b at the radially-spaced portion of the outer sheath branch open slit 548a, 548b will return to their pre-separating force radial spacing due to the elastic nature of the material forming the outer sheath branch open slit first surface 552a, 552b and the outer sheath branch open slit second surface 554a, 554b. Additionally, upon the removal of the separating force, the outer sheath branch open slit first surface 552a, 552b and the outer sheath branch open slit second surface 554a, 554b at the abutting portion of the outer sheath branch open slit 548a, 548b will return to their original abutting position due to the elastic nature of the material forming the outer sheath branch open slit first surface 552a, 552b and the outer sheath branch open slit second surface 554a, 554b.

Returning back to FIGS. 5-7, at least one c-clip 556 (shown here as c-clips 556a and 556b) or other circumferentially extending reinforcing structure may be embedded in the outer sheath 530 laterally between the outer sheath outer surface 542 and the outer sheath lumen 544 and laterally adjacent to a respective outer sheath branch open slit 548a, 548b. For example, a first c-clip 556a may be embedded in a first outer sheath branch 546a adjacent to a first outer sheath branch open slit 548a, and a second c-clip 556b may be embedded in a second outer sheath branch 546b adjacent to a second outer sheath branch open slit 548b. Instead of, or in addition to, the at least one c-clip 556a, 556b being embedded in the outer sheath 530, the at least one c-clip 556a, 556b may be selectively disposed on a portion of the outer sheath outer surface 542 that is adjacent to a respective outer sheath open slit 548. For example, a first c-clip 556a may be disposed on the outer sheath outer surface 542 on a first outer sheath branch 546a adjacent to a first outer sheath branch open slit 548a, and a second c-clip 556b may be disposed on the outer sheath outer surface 542 on a second outer sheath branch 546b adjacent to a second outer sheath branch open slit 548b. Alternatively, or in addition to the above, the at least one c-clip 556a, 556b may be selectively disposed within (e.g., via overmolding) at least a portion of the outer sheath lumen 544 that is adjacent to a respective outer sheath open slit 548a, 548b. For example, a first c-clip 556a may be disposed within at least a portion of the outer sheath lumen 544 on a first outer sheath branch 546a adjacent to a first outer sheath branch open slit 548a, and a second c-clip 556b may be disposed within at least a portion of the outer sheath lumen 544 on a second outer sheath branch 546b adjacent to a second outer sheath branch open slit 548b.

The c-clip 556a, 556b at least partially selectively prevents the outer sheath branch open slit first surface 552a, 552b from elastically separating from the outer sheath branch open slit second surface 554a, 554b when a bifurcated expandable implant branch MB-a, MB-b is disposed within the outer sheath lumen 116 adjacent to a respective outer sheath branch open slit 548a, 548b. In other words, an expandable implant M placed within the outer sheath lumen 544 in a collapsed condition may tend to want to move toward an expanded condition due to the natural properties of the expandable implant M. For example, the natural properties of the expandable implant M may include shape memory material causing the expandable implant to move from a collapsed condition to an expanded condition, an elastic deformation from a collapsed condition and a biasing back to an expanded condition, and/or any other suitable property of the expandable implant M that may urge a collapsed expandable implant M to move toward an expanded condition. Because the outer sheath open slit first surface 552a, 552b is elastically separable from the outer sheath open slit second surface 554a, 554b, the movement of the expandable implant M toward the expanded condition might tend to cause the outer sheath open slit first surface 552a, 552b to elastically separate from the outer sheath open slit second surface 554a, 554b in an unwanted manner.

However, when the at least one c-clip 556a, 556b is embedded in the outer sheath 530, the at least one c-clip 556a, 556b provides a radially inward pressure or bias to at least partially selectively prevent the expandable implant M from moving from a collapsed condition toward an expanded condition, and thus at least partially prevent the expandable implant M from elastically separating the outer sheath open slit first surface 552a, 552b from the outer sheath open slit second surface 554a, 554b. The at least one c-clip 556a, 556b may be at least partially radiopaque, and thus visible under radiography or other intraoperative imaging techniques to assist with imaging-guided placement and/or orientation.

As shown in FIG. 8, the outer sheath distal end might not include any outer sheath branches 546, for some use environments. In such case, the outer sheath 530 would have one outer sheath open tip 540a.

Figure 9:
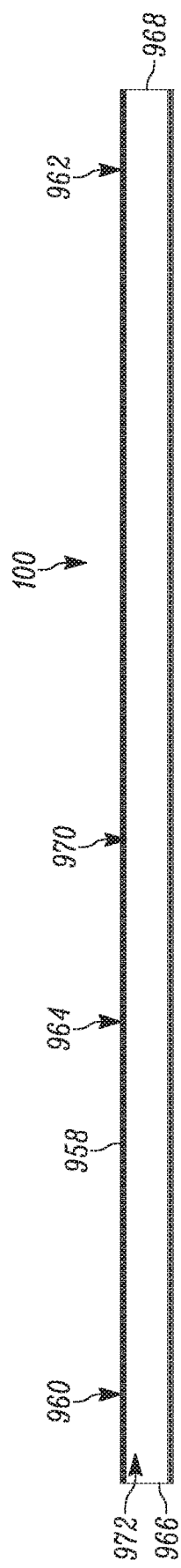
FIG. 9 is a schematic side view of an element of an implant delivery system according to one aspect of the present invention.

The implant delivery system 100 may include an inner sheath 958 having one of any number of alternate configurations, some of which will be discussed below. As shown in FIG. 9, the inner sheath 958 has an inner sheath proximal end 960, an inner sheath distal end 962, and an inner sheath body 964 longitudinally extending between the inner sheath proximal and distal ends 960, 962. The inner sheath proximal end 960 may have an inner sheath proximal opening 966. The inner sheath distal end 962 may have an inner sheath open tip 968. The inner sheath 958 may have an inner sheath outer surface 970 and an inner sheath lumen 972. The inner sheath lumen 972 may longitudinally extend between the inner sheath proximal opening 966 and the inner sheath open tip 968. The inner sheath lumen 972 is at least partially configured for selectively preventing at least a portion of the bifurcated expandable implant M from expanding from a collapsed condition when at least a portion of the bifurcated expandable implant M is disposed within the inner sheath lumen 972.

Figure 10:
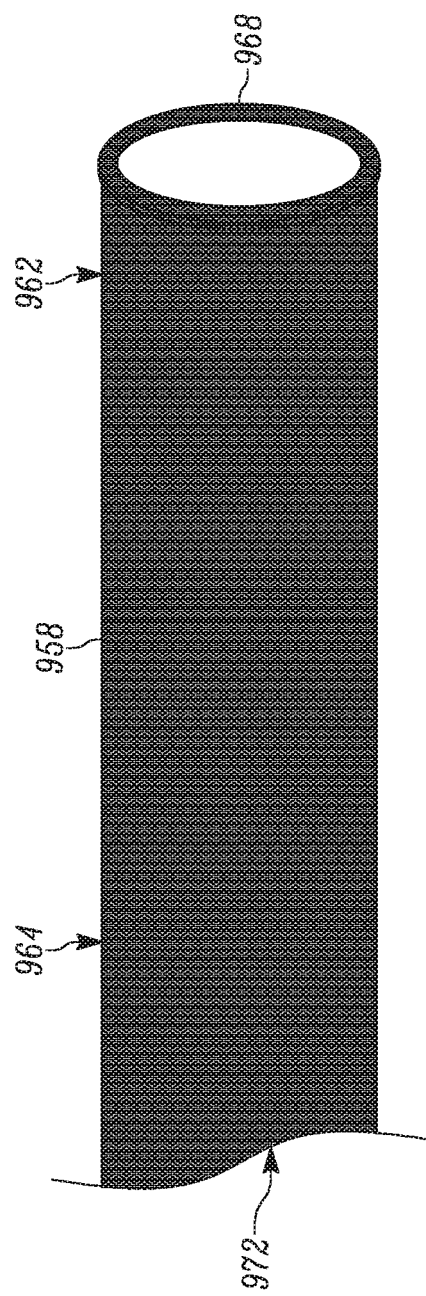
FIG. 10 is a schematic side view of the aspect of FIG. 9, including a first option for a component.
Figure 11:
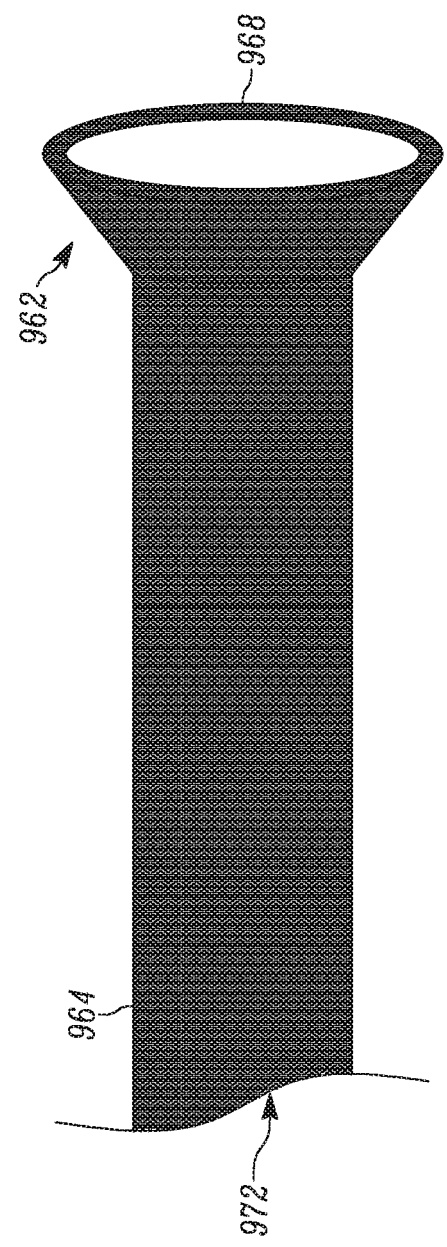
FIG. 11 is a schematic side view of the aspect of FIG. 9, including a second option for a component.

As shown in FIG. 10, the inner sheath distal end 962 and the inner sheath body 964 may be substantially level. The term "level" is defined herein as being substantially even or unvarying in diameter, as is shown by the inner sheath distal end 962 not having a gradual or stepwise diminution and/or increase in diameter in FIG. 10. As shown in FIG. 11, at least a portion of the inner sheath distal end 962 may inwardly taper at least partially from the inner sheath open tip 968 toward the longitudinally proximal direction.

Figure 12:
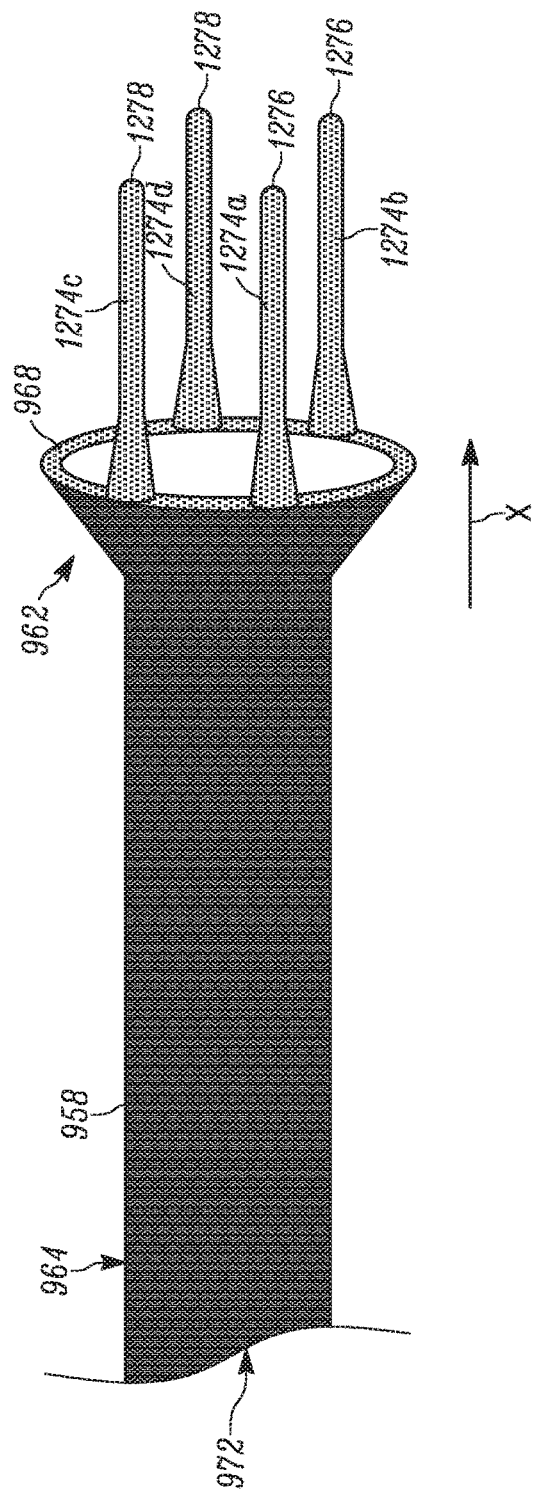
FIG. 12 is a schematic side view of the aspect of FIG. 9, including a first option for a component.
Figure 13:
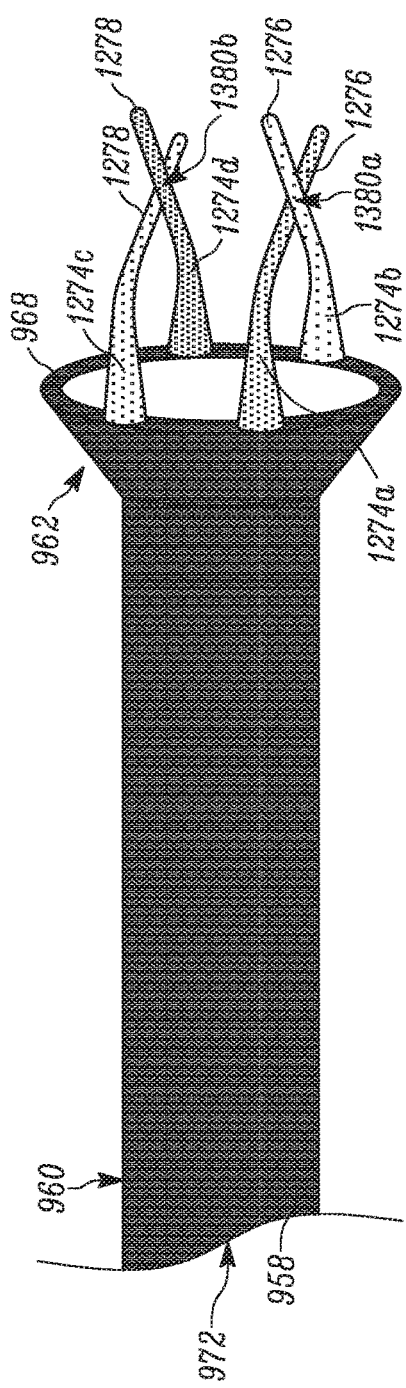
FIG. 13 is a schematic side view of the aspect of FIG. 9, including a second option for a component.
Figure 14:
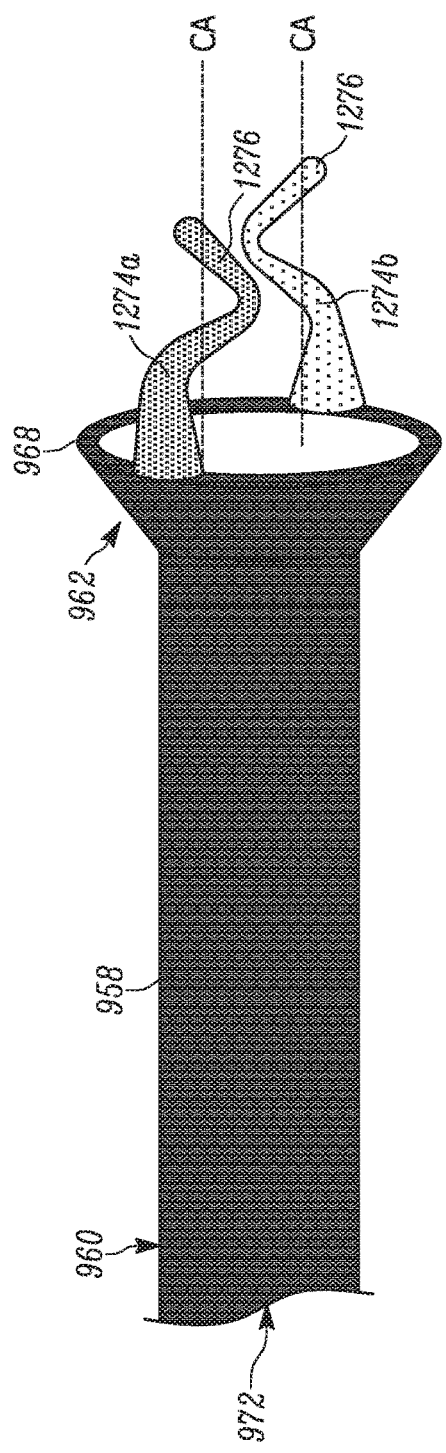
FIG. 14 is a schematic side view of the aspect of FIG. 9, including a third option for a component.

As shown in FIGS. 12-14, the inner sheath 958 may have at least one set of open slit cover members 1274 (shown here as open slit cover members 1274a, 1274b, 1274c, and 1274d). The inner sheath 958 may have a first set of open slit cover members 1276 and a second set of open slit cover members 1278 (FIGS. 12-13). The term "set" is defined herein as a number of things of the same kind that are used together. For example, the open slit cover members 1274a, 1274b of the first set of open slit cover members 1276 are used together, and the open slit cover members 1274c, 1274d of the second set of open slit cover members 1278 are used together, as will be described below. Each of the open slit cover members 1274a, 1274b, 1274c, 1274d may longitudinally extend from the inner sheath distal end 962 in a longitudinally distal direction (as shown as an arrow "X" in FIG. 12). Each open slit cover member 1274a, 1274b, 1274c, 1274d of a respective set of open slit of cover members 1276, 1278 may be oppositely positioned on the inner sheath distal end 962 from a respective open slit cover member 1274a, 1274b, 1274c, 1274d of the respective set of open slit cover members 1276, 1278. When the inner sheath 958 has the first and second sets of open slit cover members 1276, 1278, the first set of open slit cover members 1276 may be oppositely positioned on the inner sheath distal end 962 from the second set of open slit cover member 1278.

As shown in FIG. 12, each open slit cover member 1274a, 1274b, 1274c, 1274d of the first and second sets of open slit cover members 1276, 1278 may be substantially longitudinally level. As shown in FIG. 13, each open slit cover member 1274a, 1274b, 1274c, 1274d of a respective set of open slit cover members 1276, 1278 may overlap to form an overlapping portion 1380 (shown here as overlapping portions 1380a and 1380b) of each of the open slit cover members 1274a, 1274b, 1274c, 1274d of the respective set of open slit cover members 1276, 1278. In other words, a first open slit cover member 1274a of a first set of open slit cover members 1276 may overlap a second open slit cover member 1274b of the first set of open slit cover members 1276 to form an overlapping portion 1380a, and a first open slit cover member 1274c of a second set of open slit cover members 1278 may overlap a second open slit cover member 1274d of the second set of open slit cover members 1278 to form an overlapping portion 1380b. The term "overlap" is defined herein as to place or be placed so that at least a part of one covers at least a corresponding part of another as is shown by at least one of the open slit cover members 1274a, 1274b, 1274c, 1274d overlapping another of the open slit cover members 1274a, 1274b, 1274c, 1274d in FIG. 13. As shown in FIG. 14, each open slit cover member 1274a, 1274b of a respective set of open slit cover members 1276, 1278 may be helical. The term "helix" is defined herein as the shape formed by a line that curves around and along a central line, such as a central open slit cover member axis CA, as shown in FIG. 14.

Figure 15:
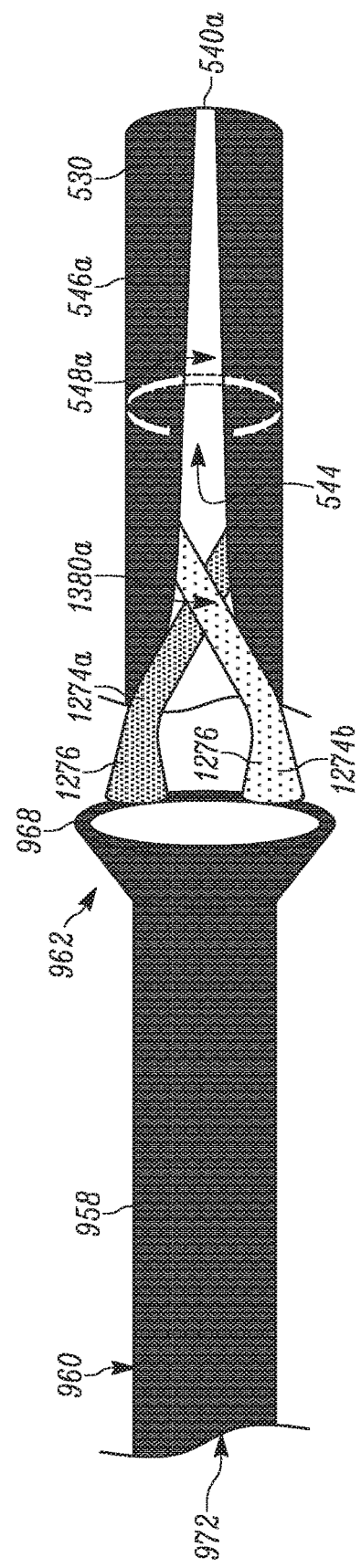
FIG. 15 is a schematic side view of a portion of the aspect of FIG. 13 in an example use configuration.
Figure 16:
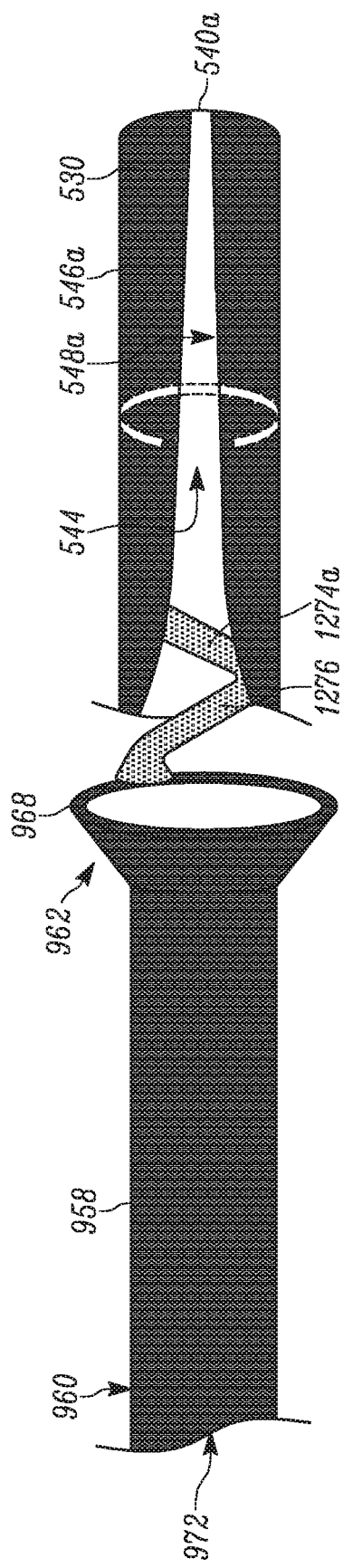
FIG. 16 is a schematic side view of a portion of the aspect of FIG. 14 in an example use configuration.

As depicted in FIGS. 15-16, when the inner sheath 958 is operatively joined to the outer sheath 530, at least a portion of each open slit cover member 1274a, 1274b, 1274c, 1274d, when provided, is positioned within the outer sheath lumen 544 adjacent to a respective outer sheath branch open slit 548a, 548b and at least partially selectively covers the respective outer sheath branch open slit 548a, 548b, as will be described below. FIG. 15 depicts at least a portion of the open slit cover members 1274a, 1274b, 1274c, 1274d of a respective set of open slit cover members 1276, 1278 (such as the first set of open slit cover members 1276, as depicted in FIG. 15) being selectively positioned within the outer sheath lumen 544 adjacent to a respective outer sheath branch open slit 548a, 548b and at least the overlapping portion 1380a, 1380b of the open slit cover members 1274a, 1274b, 1274c, 1274d at least partially selectively covering the respective outer sheath branch open slit 548a, 548b. FIG. 16 depicts at least a portion of a helical open slit cover member 1274a, 1274b, 1274c, 1274d of a respective set of open slit cover members 1276, 1278 (such as the first set of open slit cover members 1276, as depicted in FIG. 15) being selectively positioned within the outer sheath lumen 544 adjacent to a respective outer sheath branch open slit 548a, 548b and at least a portion of the helical open slit cover member 1274a, 1274b, 1274c, 1274d at least partially selectively covering the respective outer sheath branch open slit 548a, 548b.

Figure 17:
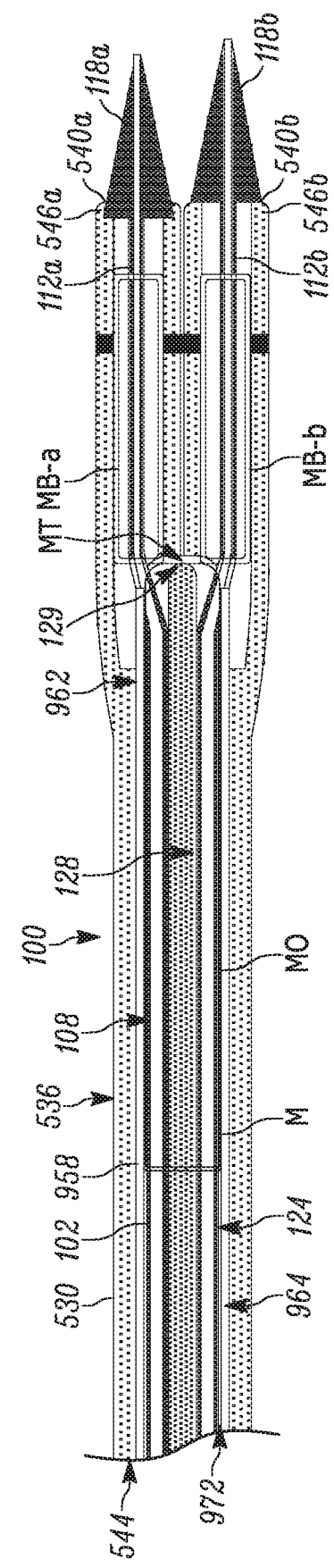
FIG. 17 is a schematic side view of an aspect of the bifurcated implant delivery system in a first example use configuration.
Figure 18:
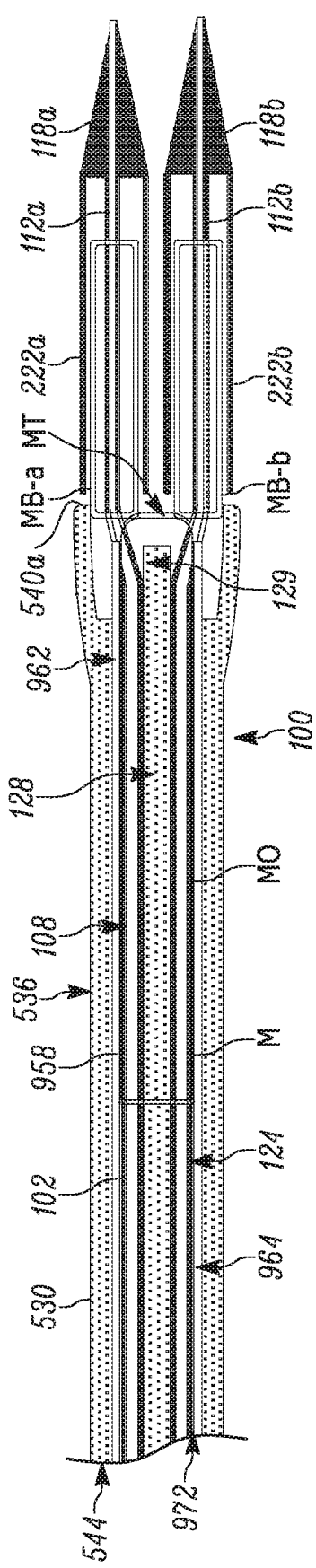
FIG. 18 is a schematic side view of an aspect of the bifurcated implant delivery system in a second example use configuration.
Figure 19:
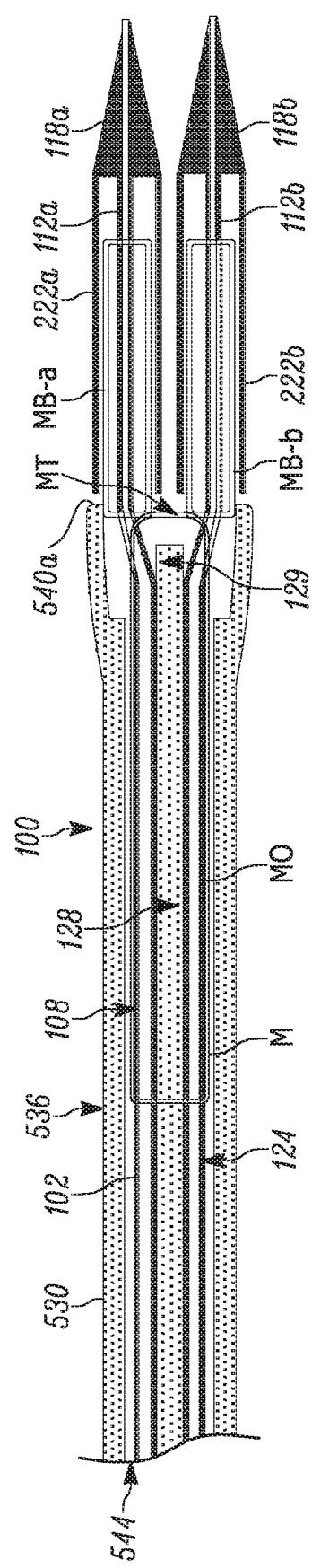
FIG. 19 is a schematic side view of an aspect of the bifurcated implant delivery system in a third example use configuration.
Figure 20:
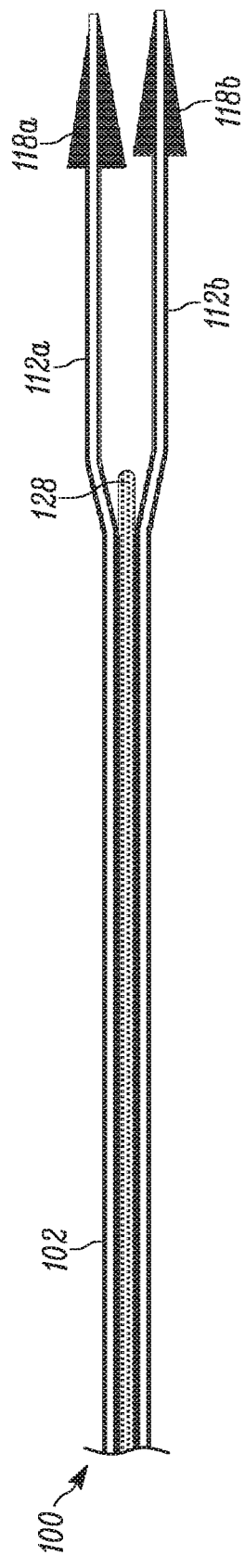

As shown in FIGS. 17-19, the implant delivery system 100 including any configuration of the outer sheath 530 may be operatively joined to any configuration of the shaft 102, and any configuration of the inner sheath 958, when provided. For the sake of brevity, not every possible combination of the alternate configurations of the outer sheath 530, the alternate configurations of the shaft 102, and the alternate configurations of the inner sheath 958, when provided, are specifically discussed and/or depicted herein, but one of ordinary skill in the art will be able to provide a suitable configuration for a particular use environment, whether or not specifically discussed and/or depicted herein, according to the teachings of the present invention.

FIG. 17 depicts the outer sheath 530 having the at least two outer sheath branches 546a, 546b operably joined both to the shaft 102 having the at least two shaft branches 112a, 112b with the nosecones 118a, 118b, and to the inner sheath 958 having a substantially level inner sheath distal end 962 and inner sheath body 964. When the bifurcated implant delivery system 100 is in the configuration shown in FIG. 17, at least a portion of the shaft 102 and at least a portion of the inner sheath 958 may be positioned within the outer sheath lumen 544. For example, at least a portion of the shaft body 108 and the inner sheath 958 may be positioned radially adjacent to at least a portion of the outer sheath body 536 within the outer sheath lumen 544, and at least a portion of each of the shaft branches 112a, 112b may be positioned radially adjacent to a respective outer sheath branch 546a, 546b within the outer sheath lumen 544. Each of the nosecones 118a, 118b may be longitudinally adjacent to a respective outer sheath open tip 540a, 540b.

The shaft outer surface 124 may have a bifurcated expandable implant M disposed, alternatively referred to as "mounted," thereon, wherein at least one of the outer sheath lumen 544 and the inner sheath lumen 972 at least partially restricts/inhibits/prevents the expandable implant M from moving from a collapsed condition toward an expanded condition. For example, at least a portion of a collapsed expandable implant body MO of a collapsed expandable implant M may be disposed on at least a portion of the shaft body 108 and restricted/inhibited/prevented from moving toward the expanded condition by a radially adjacent inner sheath lumen 972. At least a portion of each collapsed expandable implant branches MB-a, MB-b of the collapsed expandable implant M may be disposed on at least a portion of a respective shaft branch 112a, 112b and restricted/inhibited/prevented from moving toward the expanded condition by a radially adjacent outer sheath lumen 554 of a respective outer sheath branch 546a, 546b. In other words, a collapsed bifurcated expandable implant M placed within at least one of the outer sheath lumen 544 and the inner sheath lumen 972 may tend to want to move toward an expanded condition due to the natural properties of the expandable implant M. However, as shown in FIG. 17, at least one of the outer sheath lumen 544 and the inner sheath lumen 972 provides a radially inward force to at least partially restrict/inhibit/prevent the collapsed bifurcated expandable implant M from fully expanding, and/or moving toward an expanded condition. Additionally, when the shaft outer surface 124 has the bifurcated expandable implant M disposed thereon, at least a portion of the expandable implant transition portion MT may at least partially contact a reinforcing element distal end 129.

FIG. 18 depicts the outer sheath 530 having one outer sheath open tip 540 operably joined both to the shaft 102 having the at least two shaft branches 112a, 112b with the nosecones 118a, 118b and the elastic skirts 222a, 222b, and to the inner sheath 958 having a substantially level inner sheath distal end 962 and inner sheath body 964. When the bifurcated implant delivery system 100 is in the configuration shown in FIG. 18, at least a portion of the shaft 102 and at least a portion of the inner sheath 958 may be positioned within the outer sheath lumen 544. For example, at least a portion of the shaft body 108, at least a portion of each of the shaft branches 112a, 112b, and at least a portion of the inner sheath 958 may be positioned radially adjacent to at least a portion of the outer sheath body 536 within the outer sheath lumen 544, and at least a portion of each of the shaft branches 112a, 112b may extend, in the longitudinally distal direction, outward from the outer sheath open tip 540. At least one of the nosecones 118a, 118b and the elastic skirts 222a, 222b may be longitudinally adjacent to the outer sheath open tip 540.

The shaft outer surface 124 may have a bifurcated expandable implant M disposed, alternatively referred to mounted, thereon, wherein at least one of the outer sheath lumen 544, the elastic skirts 222a, 222b, and the inner sheath lumen 972 at least partially restricts/inhibits/prevents the expandable implant M from moving from a collapsed condition toward an expanded condition. For example, at least a portion of a collapsed expandable implant body MO of a collapsed expandable implant M may be disposed on at least a portion of the shaft body 108 and restricted/inhibited/prevented from moving toward the expanded condition by a radially adjacent inner sheath lumen 972. At least a portion of each collapsed expandable implant branches MB-a, MB-b of the collapsed expandable implant M may be disposed on at least a portion of a respective shaft branch 112a, 112b and restricted/inhibited/prevented from moving toward the expanded condition by at least a portion of a radially adjacent outer sheath lumen 554 and at least a portion of a respective radially adjacent elastic skirt 222a, 222b. In other words, a collapsed bifurcated expandable implant M placed within at least one of the outer sheath lumen 544, the inner sheath lumen 972, and the elastic skirts 222a, 222b may tend to want to move toward an expanded condition due to the natural properties of the expandable implant M. However, as shown in FIG. 18, at least one of the outer sheath lumen 544, the inner sheath lumen 972, and the elastic skirts 222a, 222b provides a radially inward force to at least partially restrict/inhibit/prevent the collapsed bifurcated expandable implant M from fully expanding, and/or moving toward an expanded condition. Additionally, when the shaft outer surface 124 has the bifurcated expandable implant M disposed thereon, at least a portion of a reinforcing element distal end 129 may be longitudinally spaced from the expandable implant transition portion MT, and may be configured to be at least partially brought into contact with at least a portion of the expandable implant transition portion MT, as will be described below.

FIG. 19 depicts the outer sheath 530 having one outer sheath open tip 540 operably joined to the shaft 102 having the at least two shaft branches 112a, 112b with the nosecones 118a, 118b and the elastic skirts 222a, 222b. When the bifurcated implant delivery system 100 is in the configuration shown in FIG. 19, at least a portion of the shaft 102 may be positioned within the outer sheath lumen 544. For example, at least a portion of the shaft body 108 and at least a portion of each of the shaft branches 112a, 112b may be positioned radially adjacent to at least a portion of the outer sheath body 536 within the outer sheath lumen 544, and at least a portion of each of the shaft branches 112a, 112b may extend, in the longitudinally distal direction, outward from the outer sheath open tip 540. At least one of the nosecones 118a, 118b and the elastic skirts 222a, 222b may be longitudinally adjacent to the outer sheath open tip 540.

The shaft outer surface 124 may have a bifurcated expandable implant M disposed, alternatively referred to mounted, thereon, wherein at least one of the outer sheath lumen 544 and the elastic skirts 222a, 222b at least partially restricts/inhibits/prevents the expandable implant M from moving from a collapsed condition toward an expanded condition. For example, at least a portion of a collapsed expandable implant body MO of a collapsed expandable implant M may be disposed on at least a portion of the shaft body 108 and restricted/inhibited/prevented from moving toward the expanded condition by a radially adjacent outer sheath lumen 544. At least a portion of each collapsed expandable implant branches MB-a, MB-b of the collapsed expandable implant M may be disposed on at least a portion of a respective shaft branch 112a, 112b and restricted/inhibited/prevented from moving toward the expanded condition by at least a portion of a radially adjacent outer sheath lumen 554 and at least a portion of a respective radially adjacent elastic skirt 222a, 222b. In other words, a collapsed bifurcated expandable implant M placed within at least one of the outer sheath lumen 544 and the elastic skirts 222a, 222b may tend to want to move toward an expanded condition due to the natural properties of the expandable implant M. However, as shown in FIG. 19, at least one of the outer sheath lumen 544 and the elastic skirts 222a, 222b provides a radially inward force to at least partially restrict/inhibit/prevent the collapsed bifurcated expandable implant M from fully expanding, and/or moving toward an expanded condition. Additionally, when the shaft outer surface 124 has the bifurcated expandable implant M disposed thereon, at least a portion of a reinforcing element distal end 129 may be longitudinally spaced from the expandable implant transition portion MT, and may be configured to be at least partially brought into contact with at least a portion of the expandable implant transition portion MT, as will be described below.

In use, the bifurcated implant delivery system 100, as described above, is provided to the user. The implant delivery system 100 may include any configuration of the outer sheath 530, any configuration of the shaft 102, and any configuration of the inner sheath 958 when provided, or a combination of individual features described above for the alternate configurations of the outer sheath 530, the shaft 102, and the inner sheath 958. For the sake of brevity, not every possible combination of the alternate configurations of the outer sheath 530, the alternate configurations of the shaft 102, and the alternate configurations of the inner sheath 958, when provided, are discussed and/or depicted. However, it is to be understood that the following description may be applicable to any combination of configurations of the outer sheath 530, the shaft 102, and the inner sheath 958, when provided, that one of ordinary skill in the art could devise, based upon the present teachings.

FIGS. 20-36 depict an example sequence of operation of the bifurcated implant delivery system 100, as depicted in FIG. 17. At least one bifurcated expandable implant M, which can be self-expandable and/or expand through external means (e.g., a balloon), is provided. The bifurcated expandable implant M may have an expandable implant body MO, at least two expandable implant branches MB-a, MB-b, and an expandable implant transition portion MT longitudinally between the expandable implant body MO and the at least two expandable implant branches MB-a, MB-b.

Figure 21:
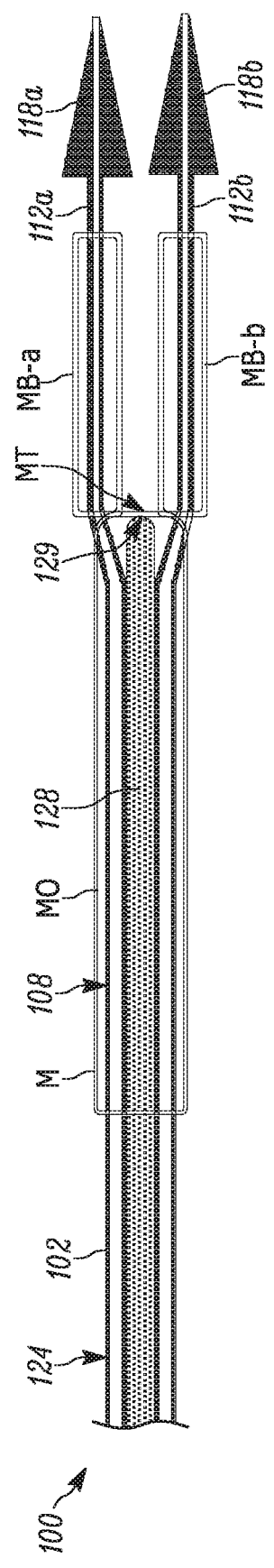

As shown in FIG. 21, a collapsed expandable implant M may be placed in operative engagement with the shaft outer surface 124. In particular, a collapsed bifurcated expandable implant M may be circumferentially mounted on the shaft outer surface 124 with the expandable implant body MO circumferentially mounted on at least a portion of the shaft body 108, each of the expandable implant branches MB-a, MB-b circumferentially mounted on a respective shaft branch 112a, 112b, and at least a portion of the expandable implant transition portion MT at least partially contacting a reinforcing element distal end 129.

Figure 22:
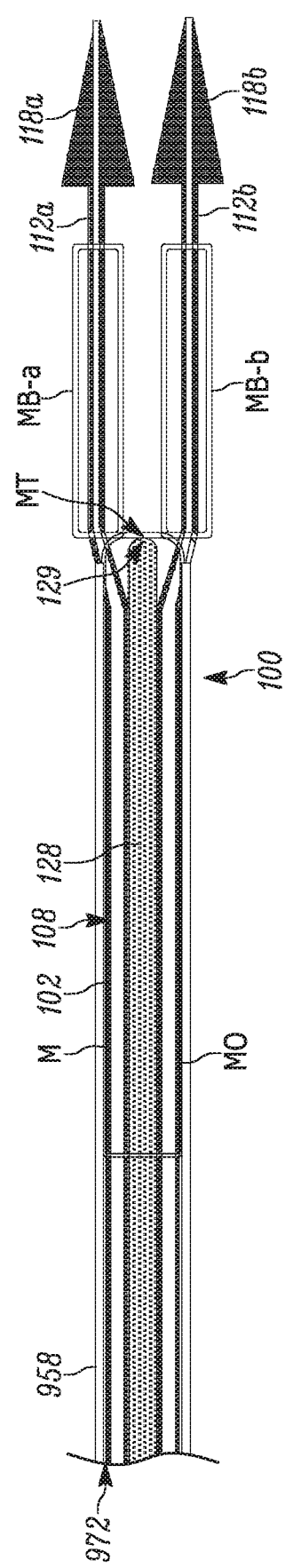

As shown in FIG. 22, with the collapsed bifurcated expandable implant mounted M on the shaft 102, at least a portion of the collapsed expandable implant body MO and at least a portion of the shaft body 108 may be operatively engaged to the inner sheath 958, such as by being collectively inserted into at least a portion of the inner sheath lumen 972. As shown in FIGS. 23-24, when the inner sheath 958 has at least one set of open slit cover members 1276, 1278, the open slit cover members 1274a, 1274b, 1274c, 1274d may at least partially surround and/or engage at least a portion of the collapsed expandable implant M when the shaft 102 and at least a portion of the collapsed expandable implant M is operatively engaged to the inner sheath 958.

Figure 25:
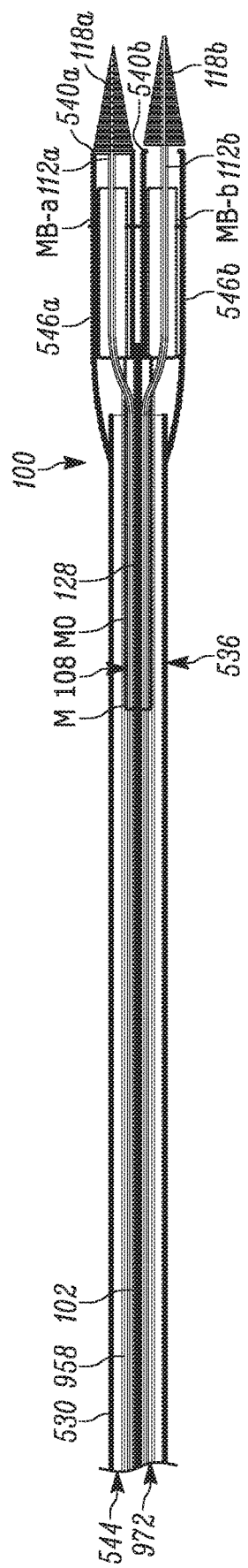

As shown in FIG. 25, at least a portion of the inner sheath 958, at least a portion of the collapsed bifurcated expandable implant M and at least a portion of the shaft 102 may be operatively joined to the outer sheath 530, such as by being collectively inserted into at least a portion of the outer sheath lumen 544. With at least a portion of the collapsed bifurcated expandable implant M, at least a portion of the shaft 102, and at least a portion of the inner sheath 958 inserted in the outer sheath lumen 544, the inner sheath 958, the shaft 102, and the collapsed bifurcated expandable implant M may be positioned in the outer sheath lumen 544. In particular, the inner sheath 958, the shaft 102, and the collapsed bifurcated expandable implant M may be positioned in the outer sheath lumen 544 with at least a portion of the inner sheath 958, at least a portion of the shaft body 108, and at least a portion of the expandable implant body MO being in, and/or radially adjacent to, the outer sheath body 536, with at least a portion of each shaft branch 112a, 112b and at least a portion of each collapsed expandable implant branch MB-a, MB-b being in, and/or radially adjacent to, a respective outer sheath branch 546a, 546b, and with each nosecone 118a, 118b being longitudinally adjacent to a respective outer sheath open tip 540a, 540b.

Figure 26:
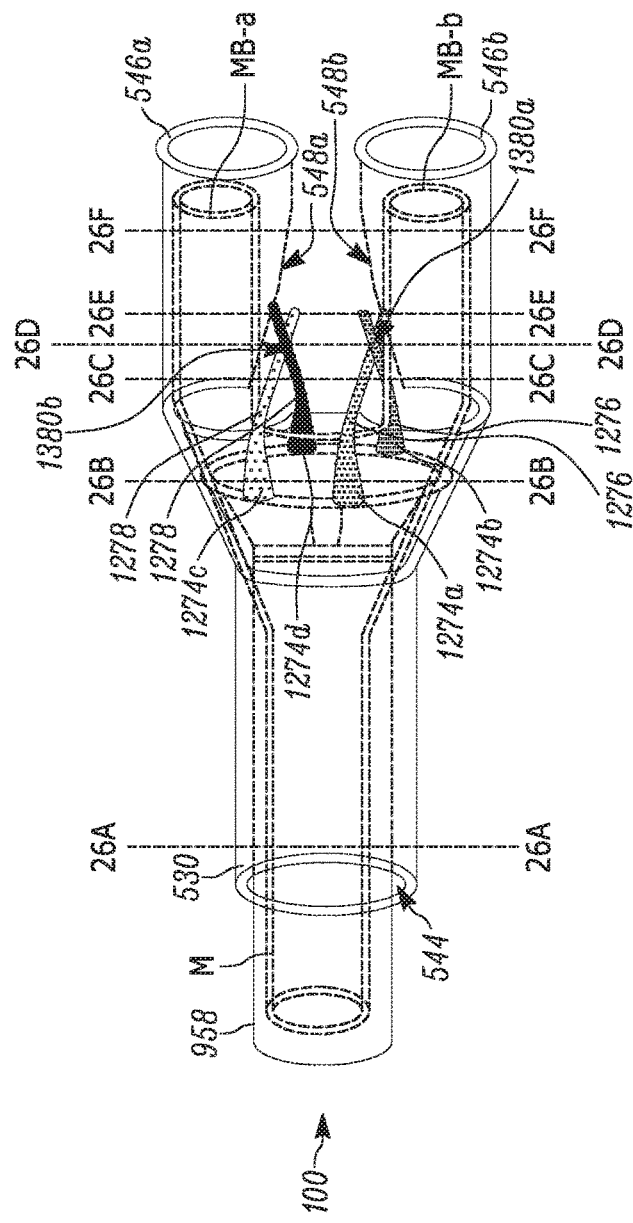
Figure 26A:
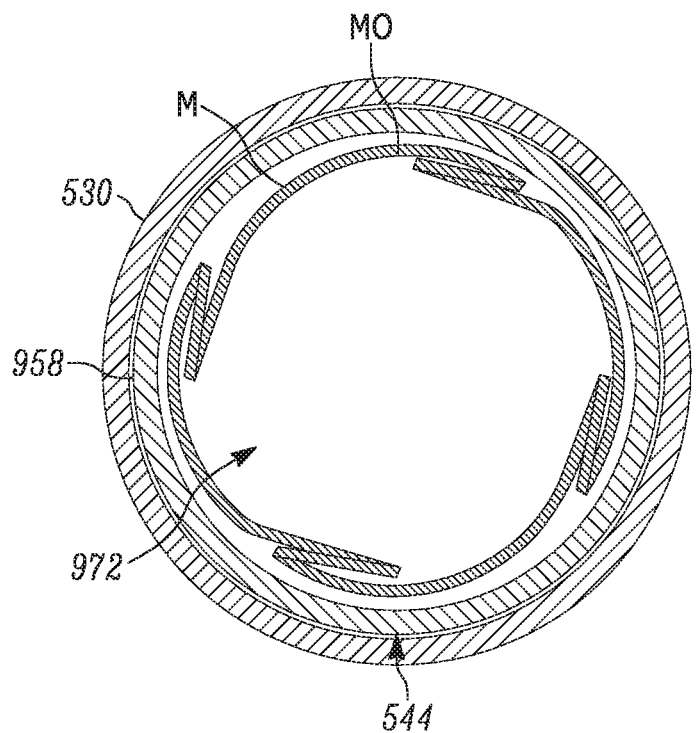
Figure 26B:
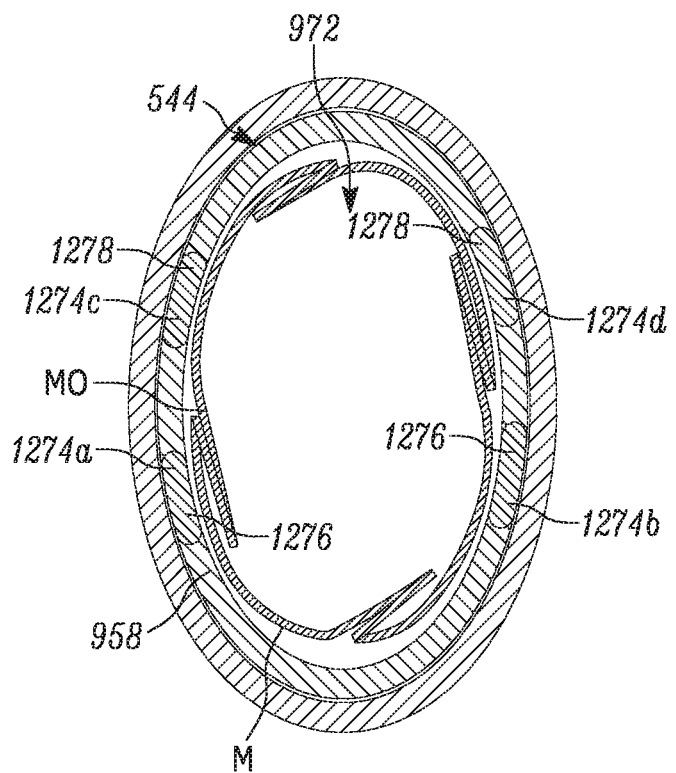
Figure 26C:
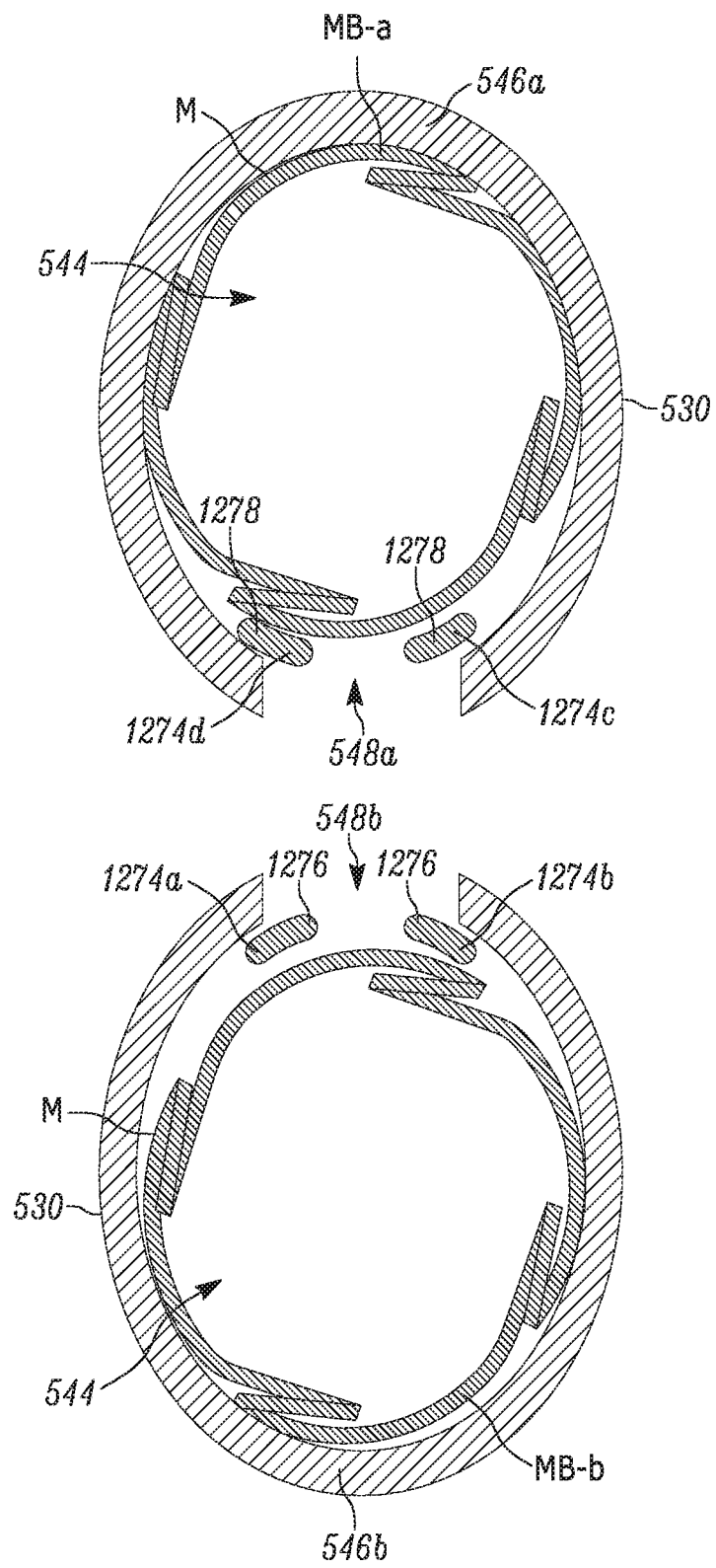
Figure 26D:
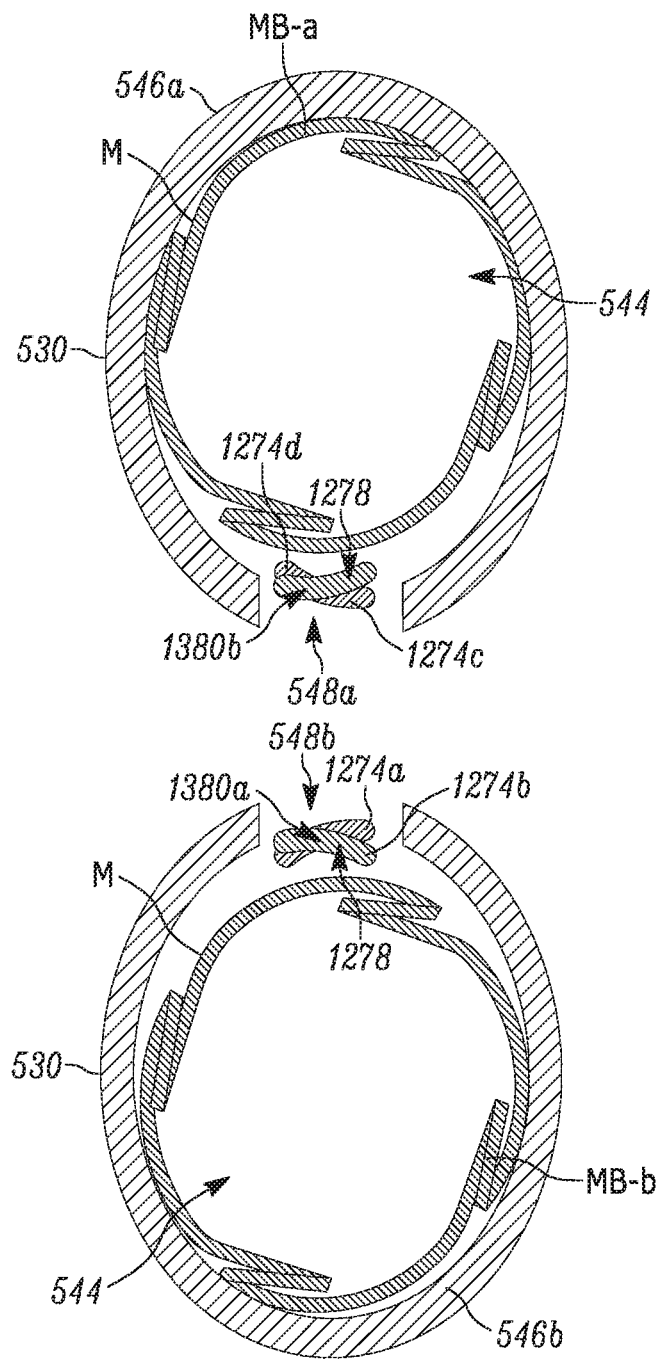
Figure 26E:
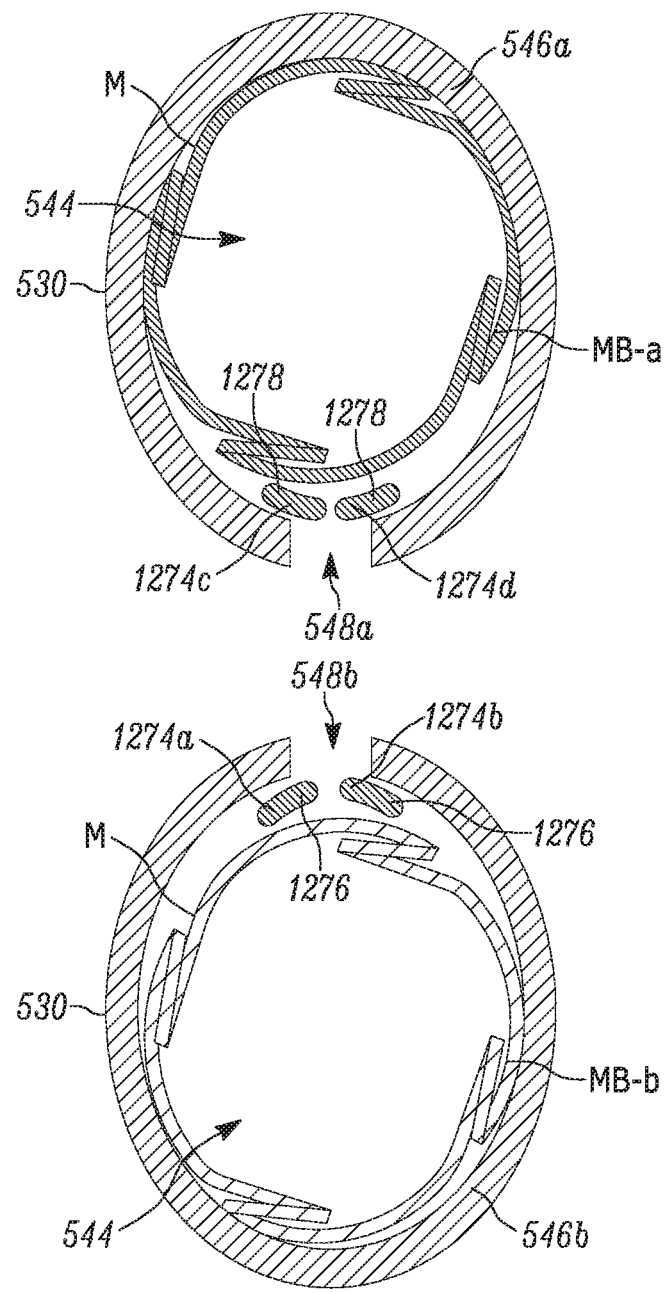
Figure 26F:
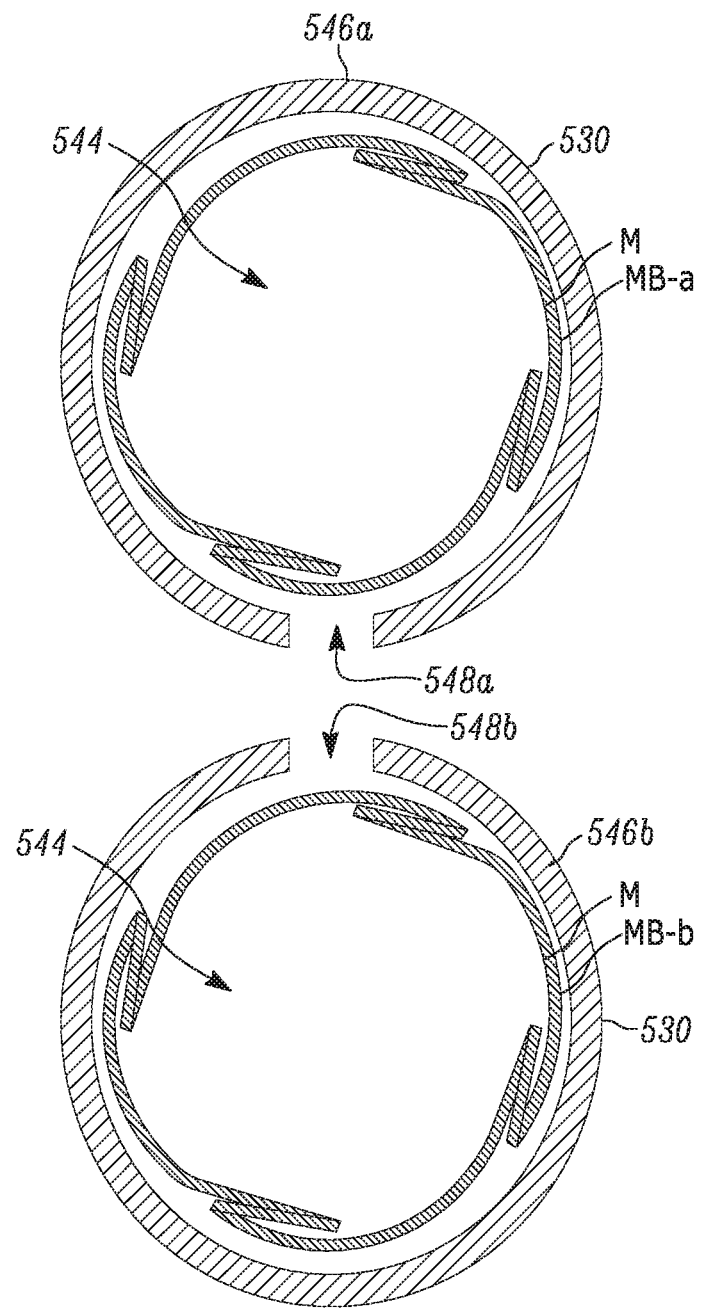
Figure 27:
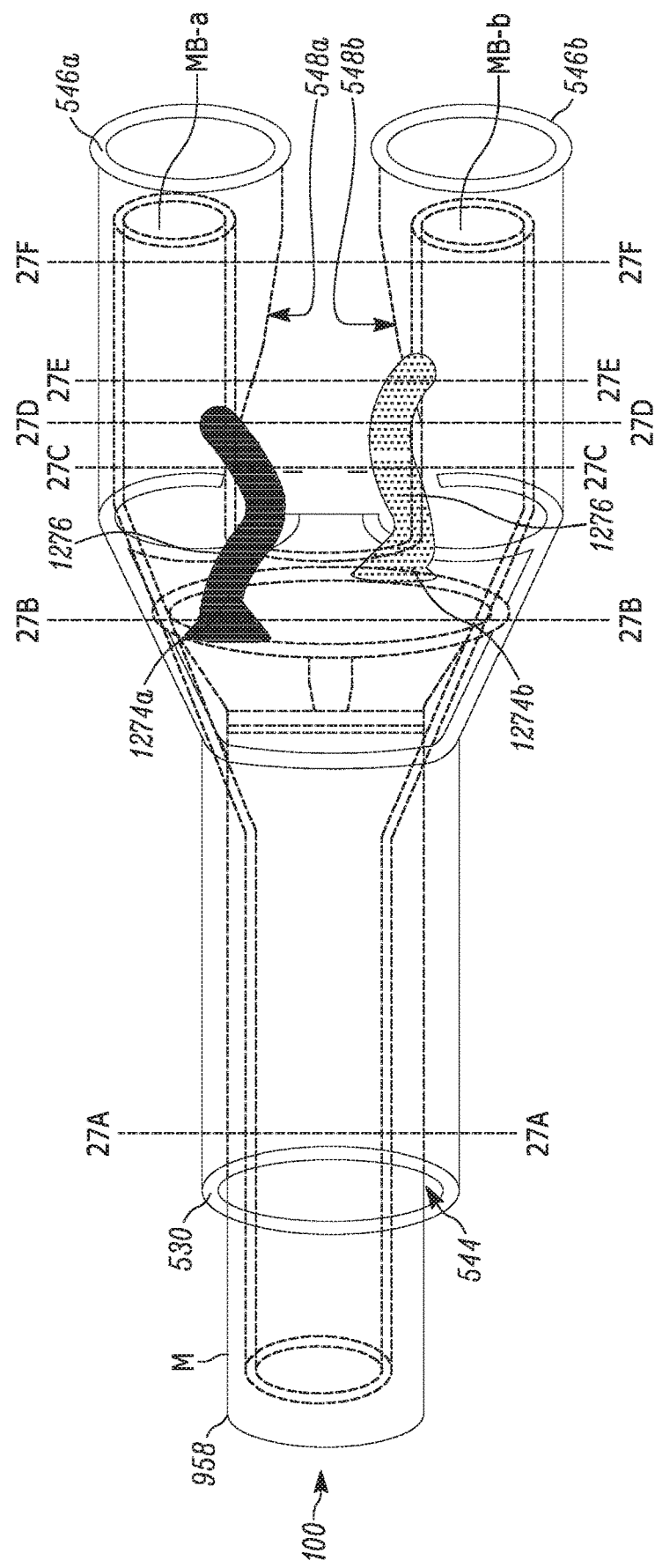
Figure 27A:
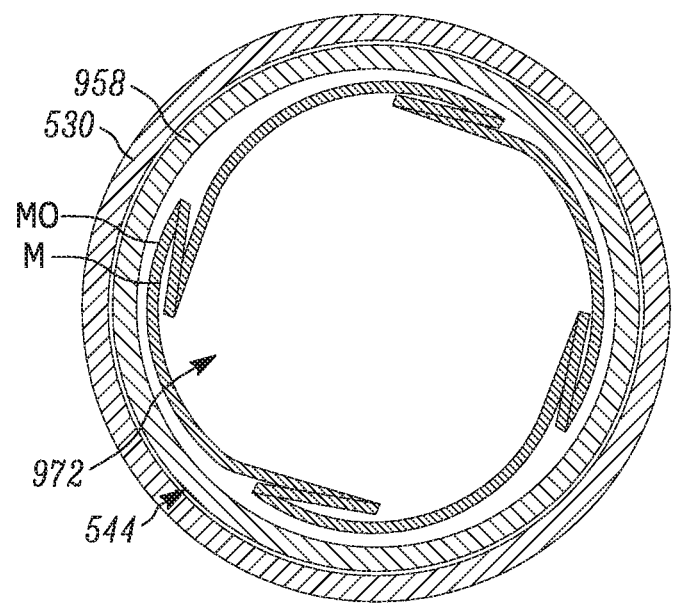
Figure 27B:
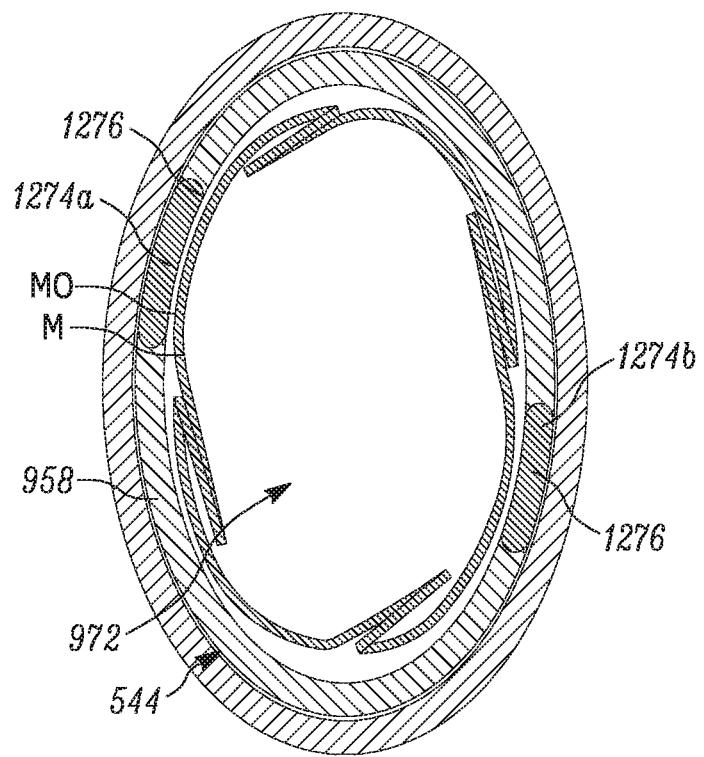
Figure 27C:
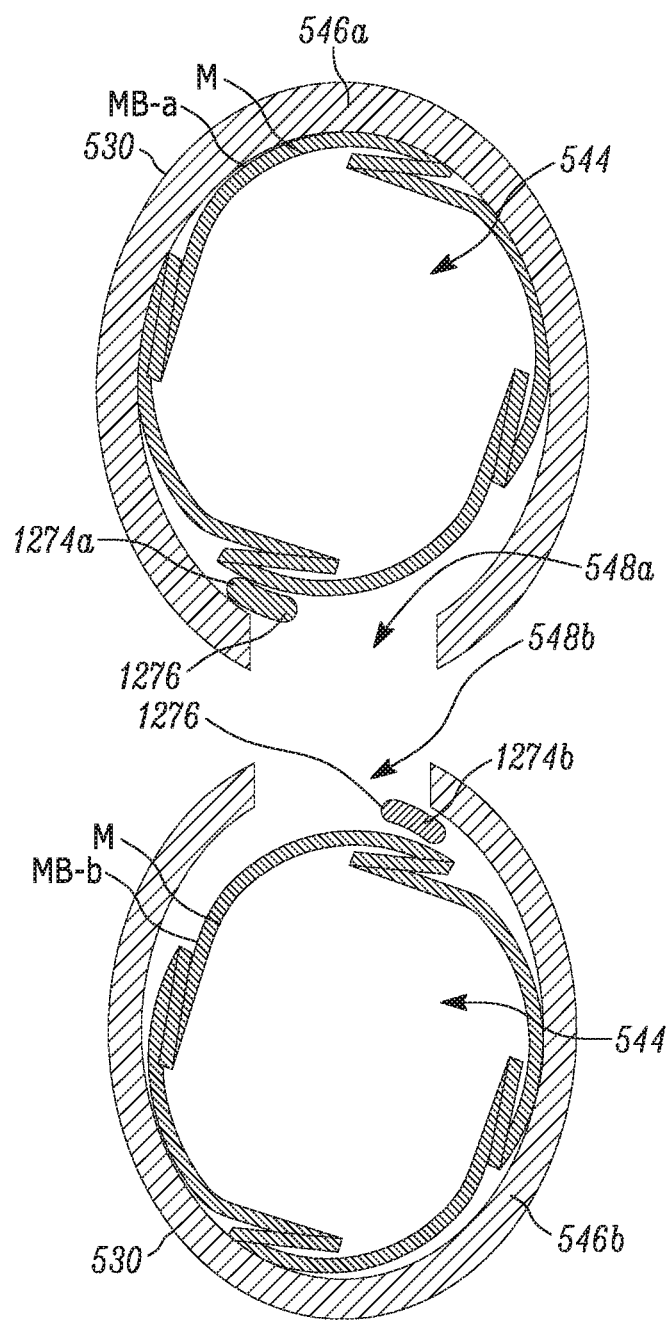
Figure 27D:
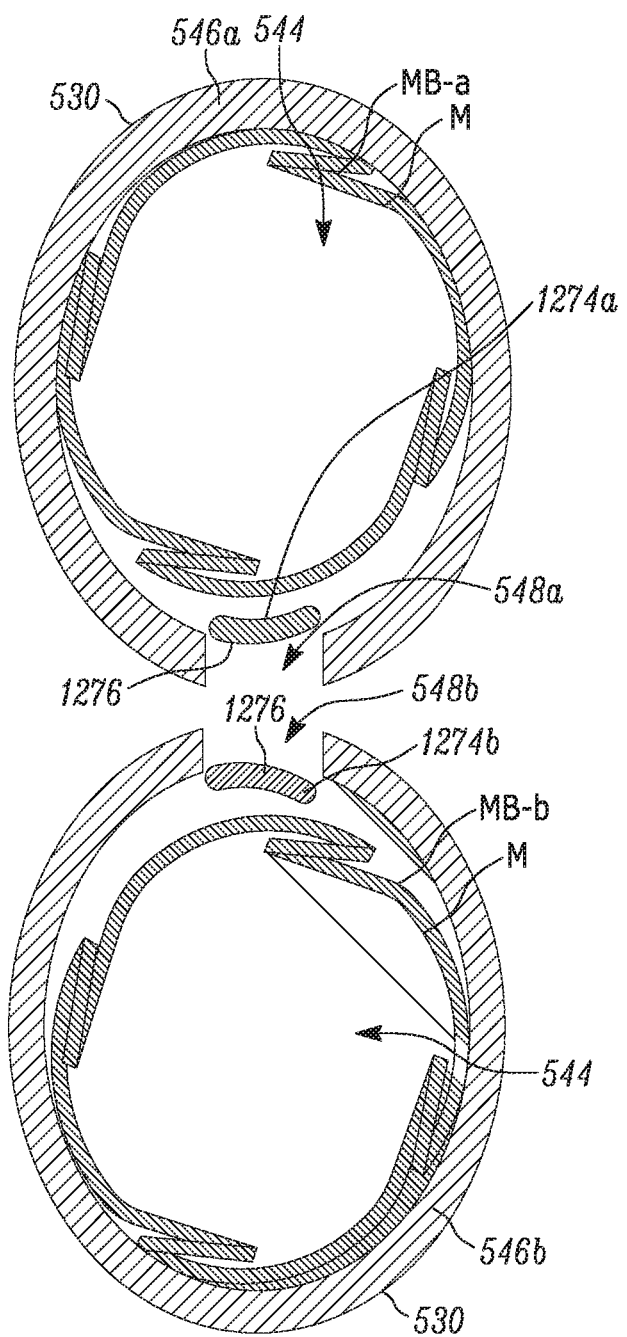
Figure 27E:
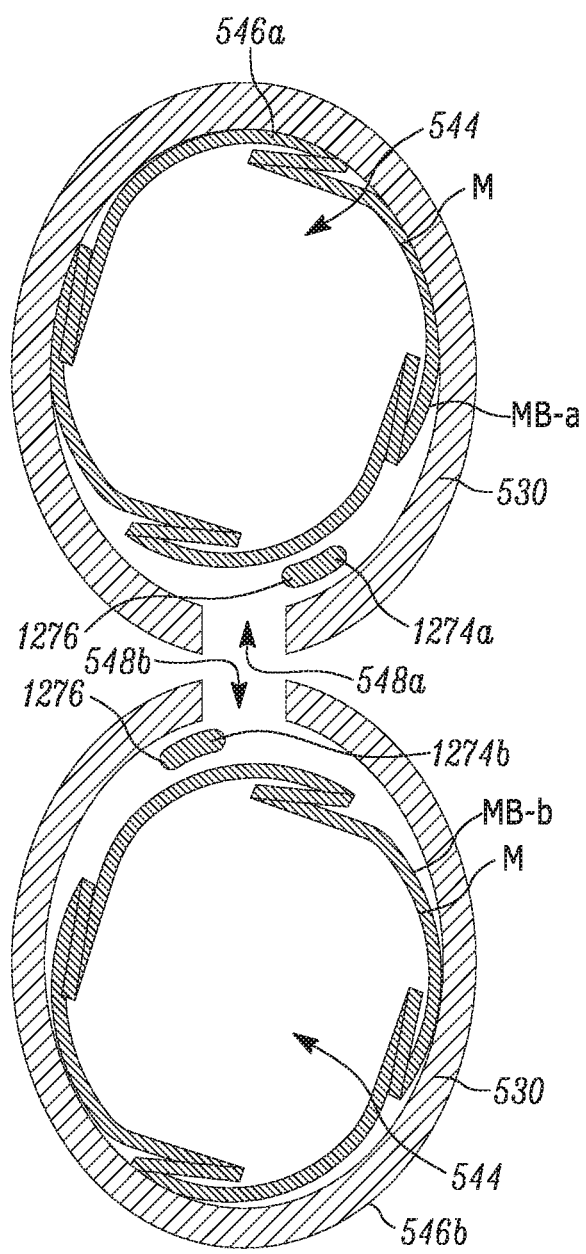
Figure 27F:
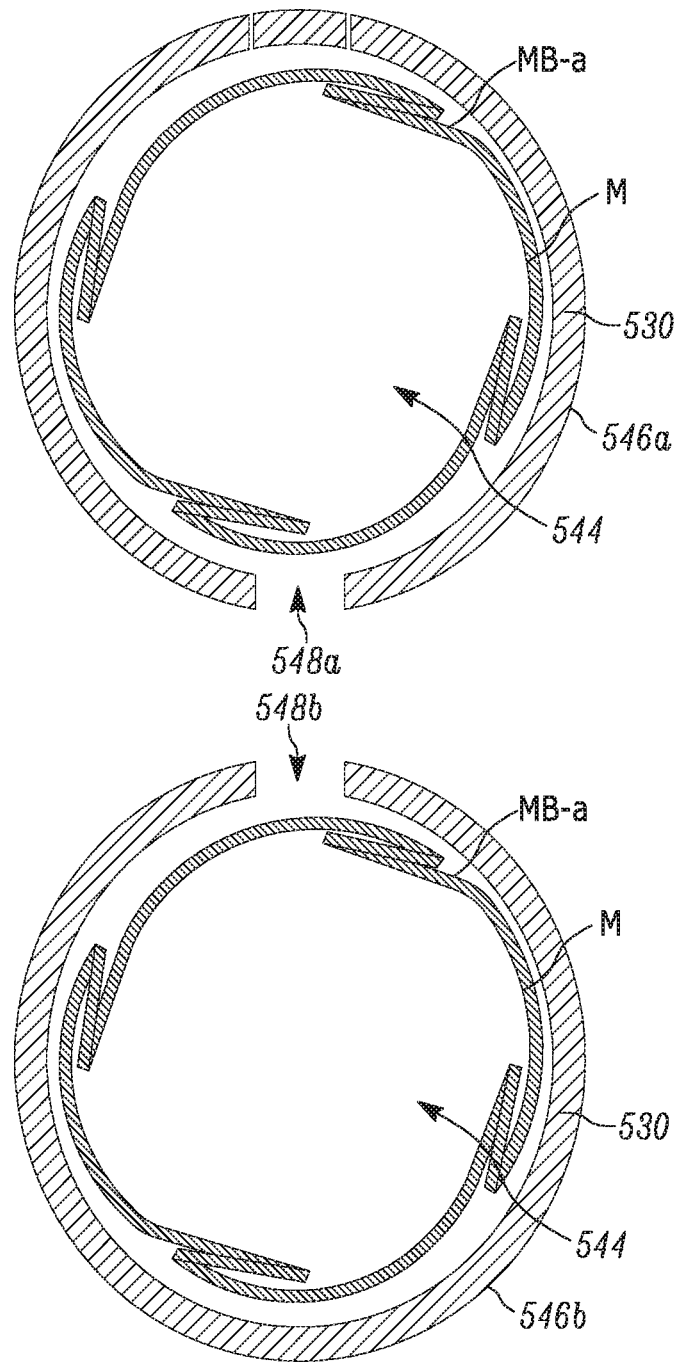

As shown in FIGS. 26-27, when the inner sheath 958 has at least one set of open slit cover members 1276, 1278, the inner sheath 958 may be aligned/positioned in the outer sheath lumen 544 with at least a portion of each open slit cover member 1274a, 1274b, 1274c, 1274d being positioned adjacent to a respective outer sheath branch open slit 548a, 548b, and at least partially covering the respective outer sheath branch open slit 548a, 548b. Each open slit cover member 1274a, 1274b, 1274c, 1274d may at least partially provide a barrier between a respective outer sheath branch open slit 548a, 548b and a respective expandable implant branch MB-a, MB-b. FIG. 26a-f depict cross-sectional views of various points along the implant delivery system 100, to show the arrangement of the outer sheath 530, the inner sheath 758 with the open slit cover members 1274a, 1274b, 1274c, 1274d, and the bifurcated expandable implant M in FIG. 26. FIG. 27a-f depict cross-sectional views of various points along the implant delivery system 100, to show the arrangement of the outer sheath 530, the inner sheath 758 with the open slit cover members 1274a, 1274b, 1274c, 1274d, and the bifurcated expandable implant M in FIG. 27.

Figure 28:
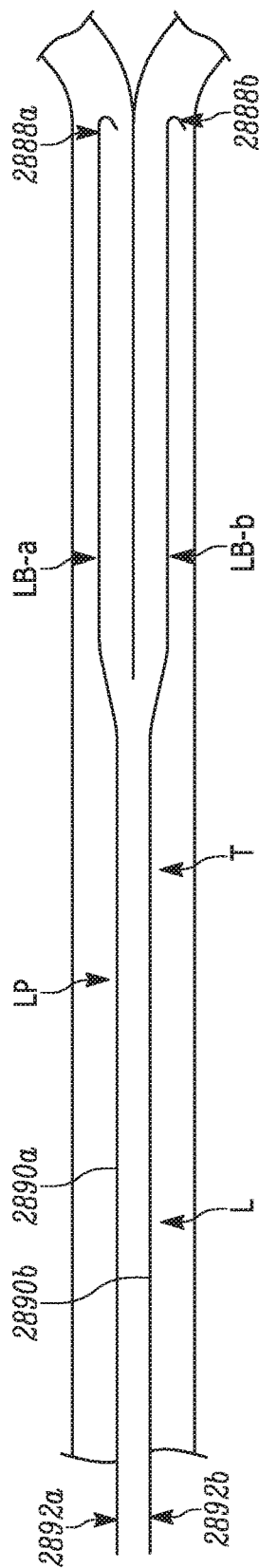
Figure 29:
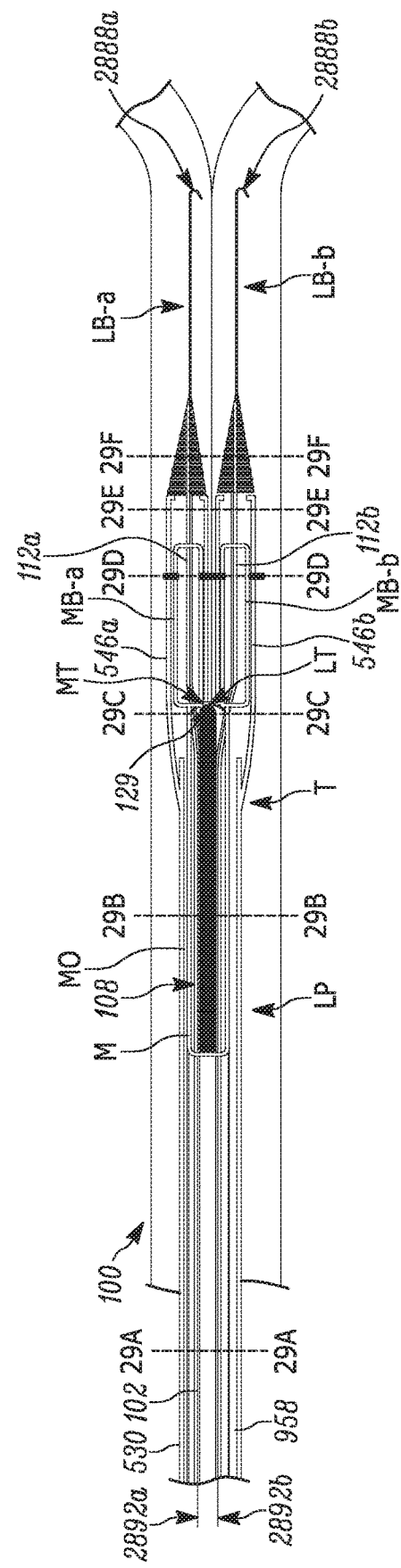
Figure 29A:
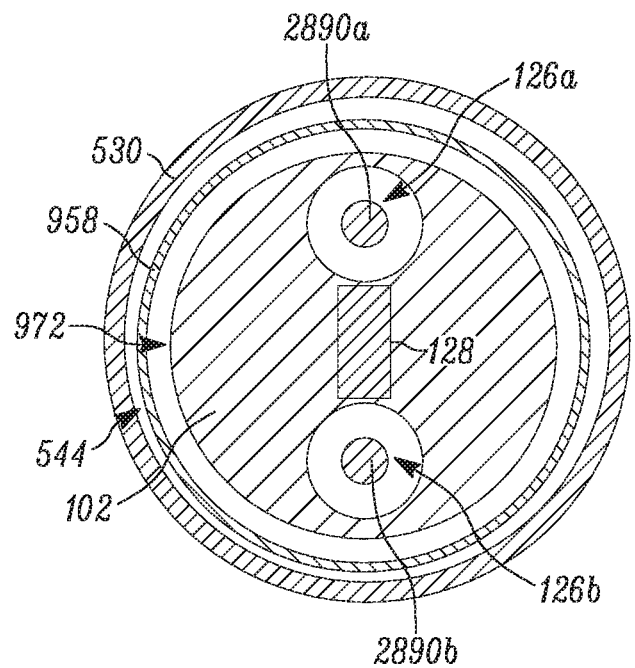
Figure 29B:
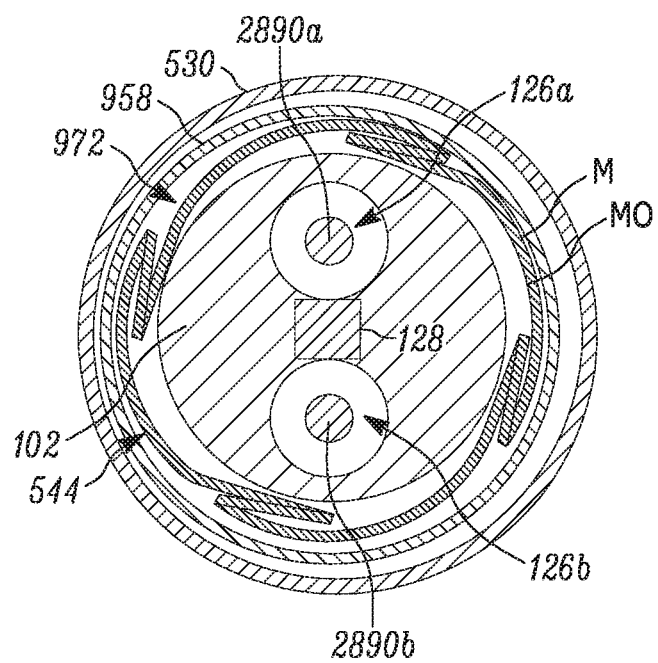
Figure 29C:
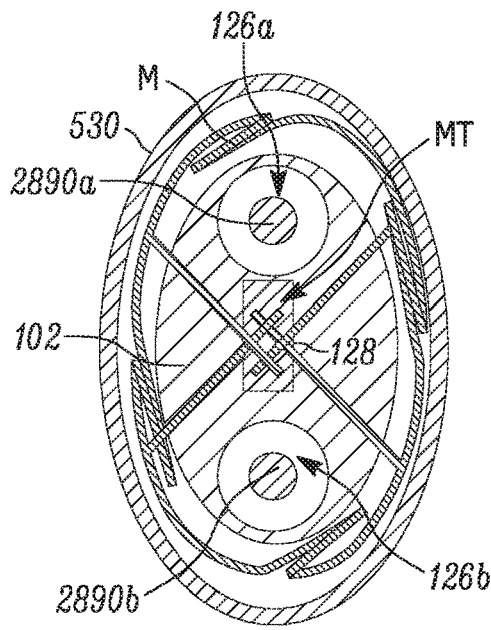
Figure 29D:
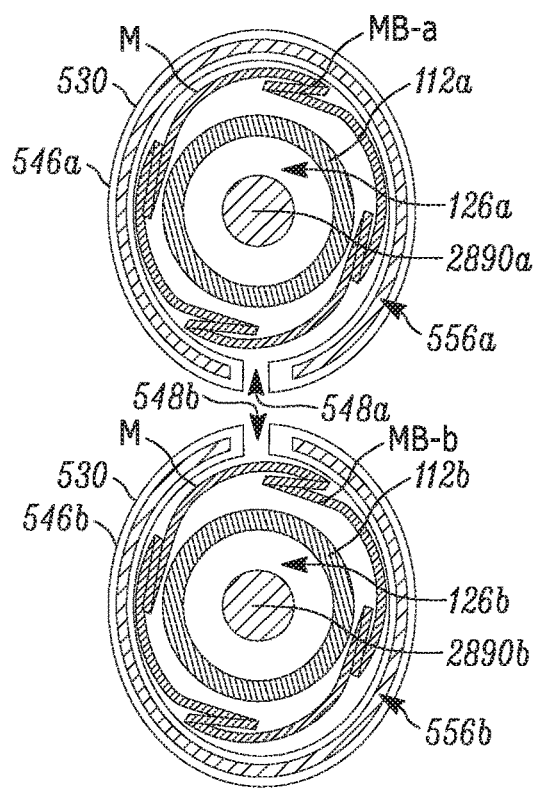
Figure 29E:
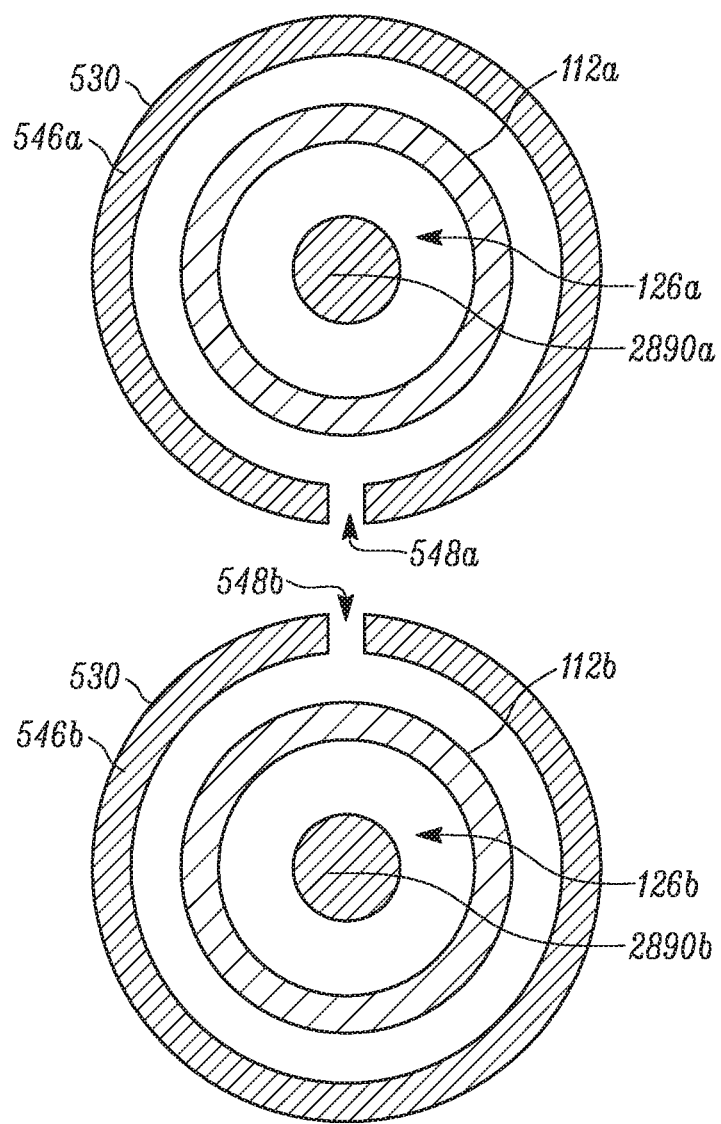
Figure 30B:
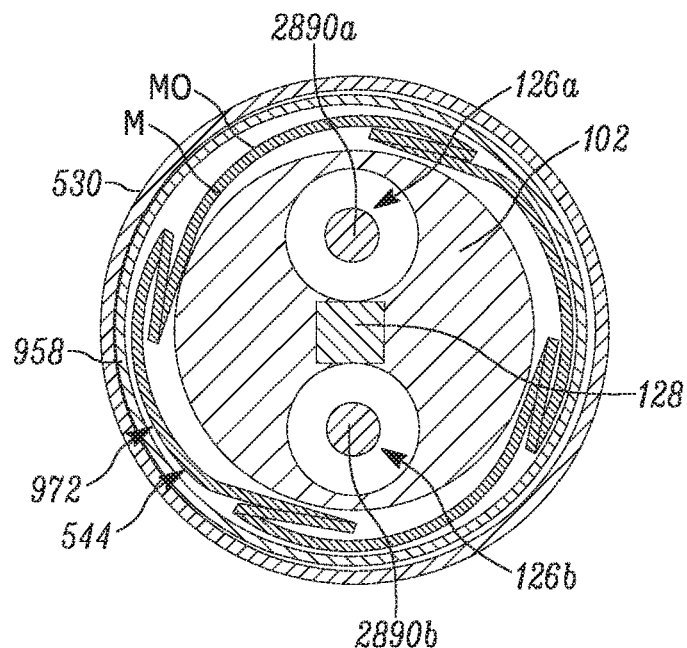
Figure 30C:
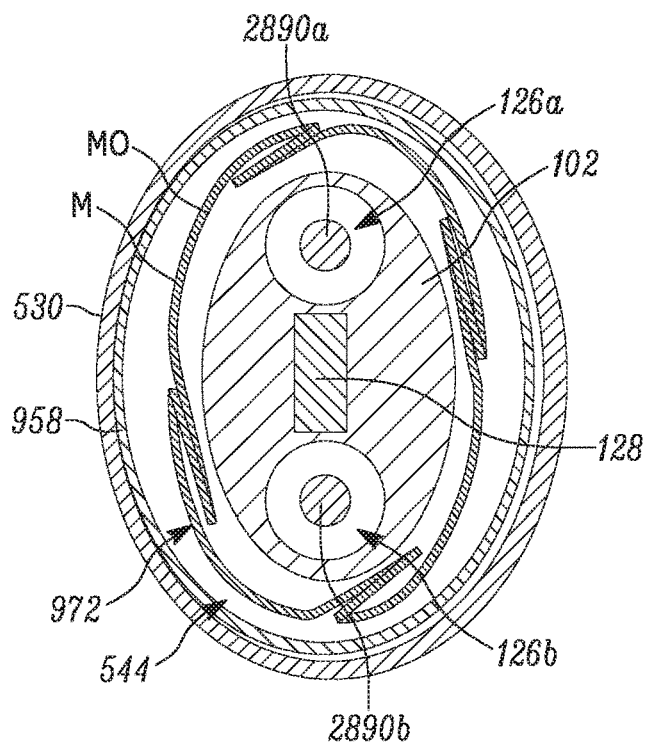
Figure 30D:
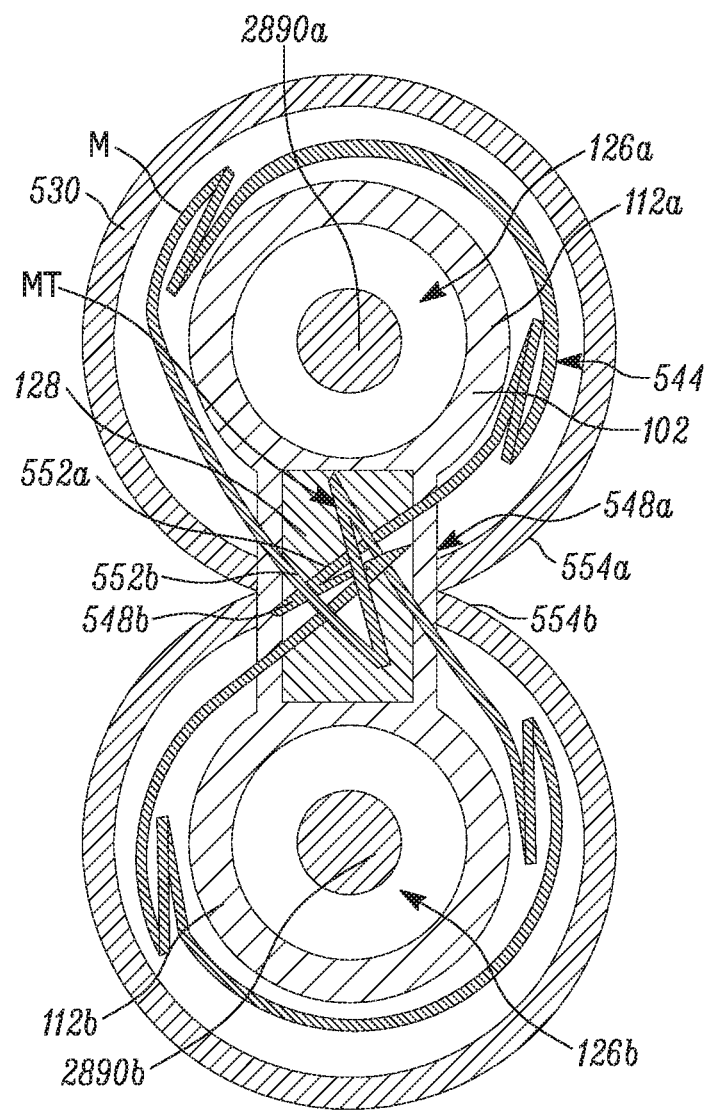
Figure 30E:
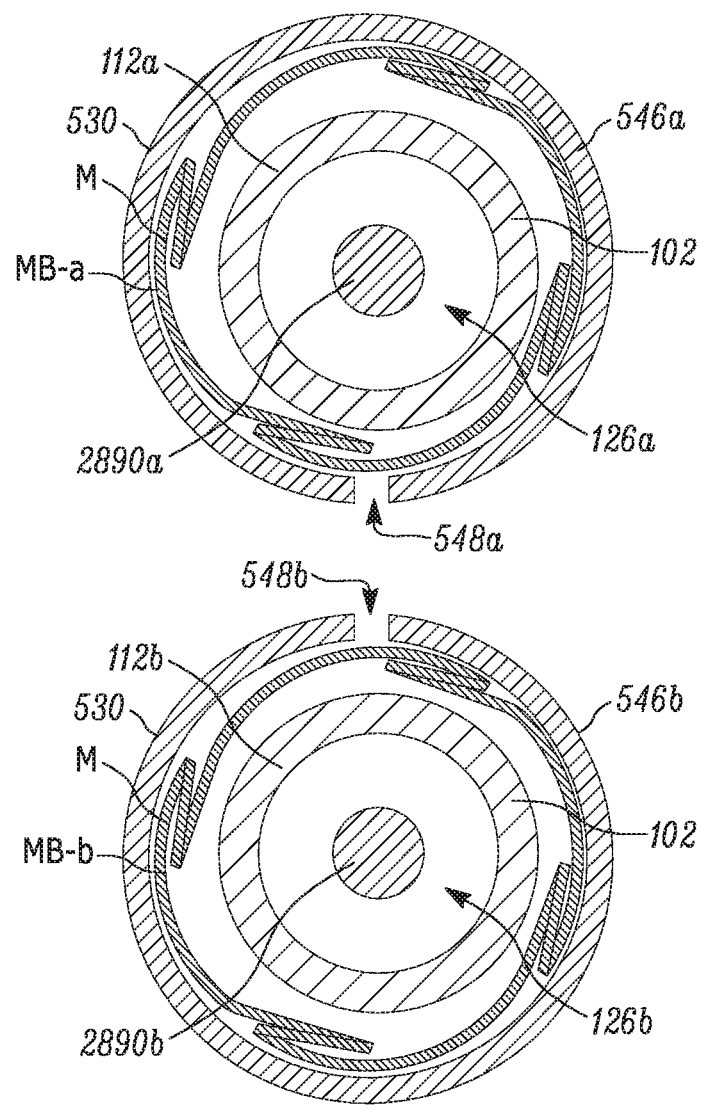
Figure 30F:
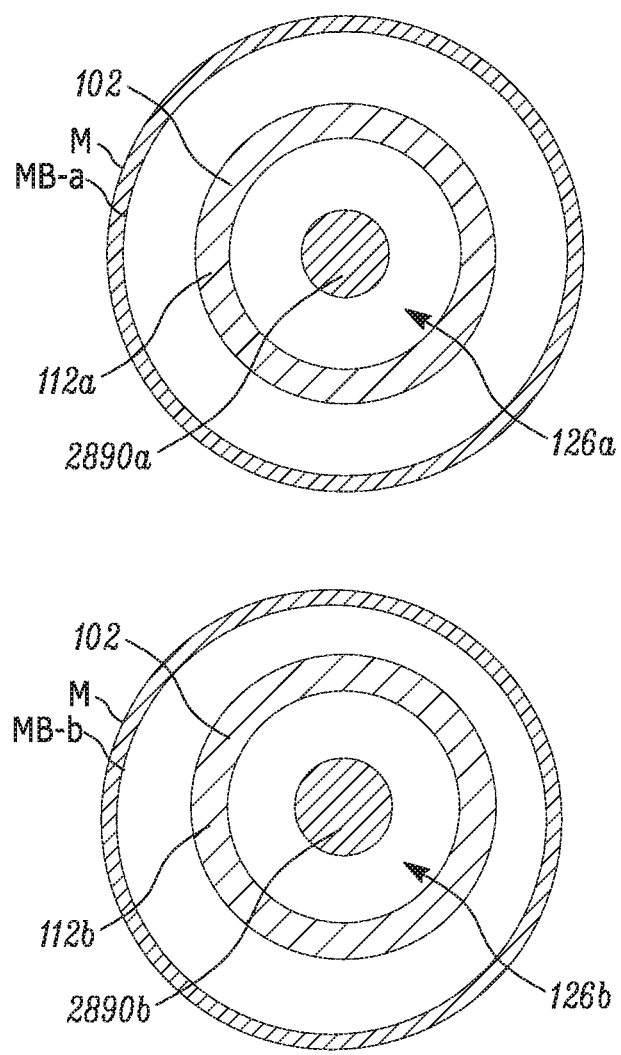

As shown in FIG. 28, at least two guidewire distal ends 2888 (shown here as guidewire distal ends 2888a and 2888b) are inserted into a target patient tissue site T in a patient lumen L with each guidewire distal end 2888a, 2888b of at least two guidewires 2890 (shown here as guidewires 2890a and 2890b) being positioned in a respective patient lumen branch LB-a, LB-b. Each patient lumen branch LB-a, LB-b bifurcates from a patient lumen main portion LP. Each guidewire proximal end 2892 (shown here as guidewire proximal ends 2892a and 2892b) of the at least two guidewires 2890a, 2890b are directed through the implant delivery system 100 by being directed through the at least one shaft lumen 126, such as through a respective shaft lumen 126a, 126b. As shown in FIG. 29, the implant delivery system 100 may be directed to the target patient tissue site T along the at least two guidewires 2890a, 2890b.

The implant delivery system 100 may be positioned at the target patient tissue site T. In particular, at least a portion of the outer sheath 530, at least a portion of the inner sheath 958, at least a portion of the shaft body 108, and at least a portion of the expandable implant body MO may be positioned in a patient lumen main portion LP. At least a portion of each outer sheath branch 546a, 546b, at least a portion of each shaft branch 112a, 112b, and at least a portion of each expandable implant branch MB-a, MB-b may be positioned in a respective patient lumen branch LB-a, LB-b. At least a portion of the reinforcing element distal end 129 and at least a portion of the expandable implant transition portion MT may be positioned at a patient lumen transition portion LT. FIG. 29a-f depict cross-sectional views of various points along the implant delivery system 100, to show the arrangement of the outer sheath 530, the inner sheath 758, the shaft 102, and the bifurcated expandable implant M in FIG. 29.

Figure 31:
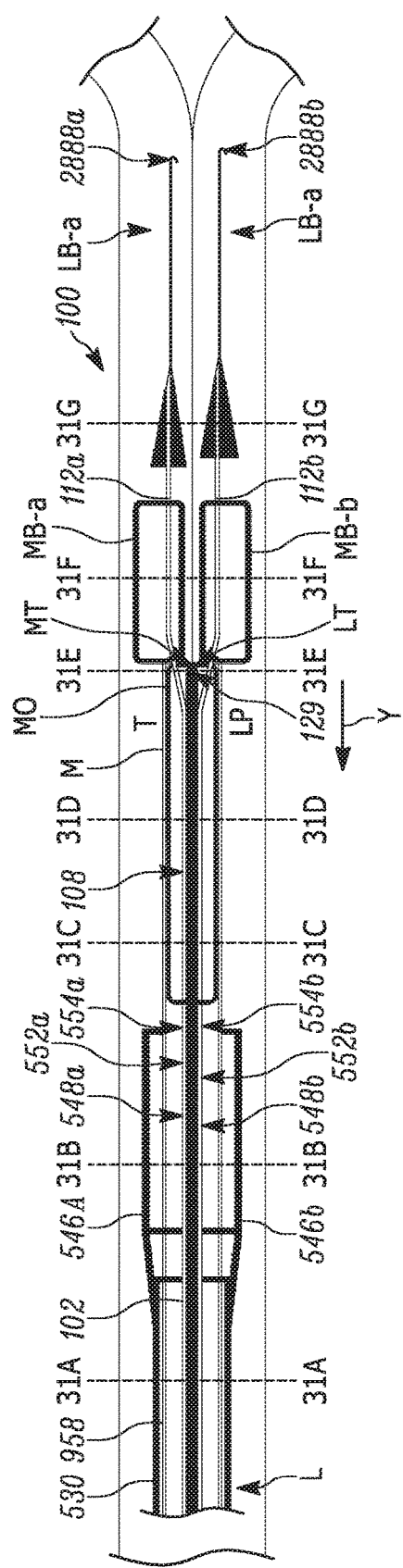
Figure 31A:
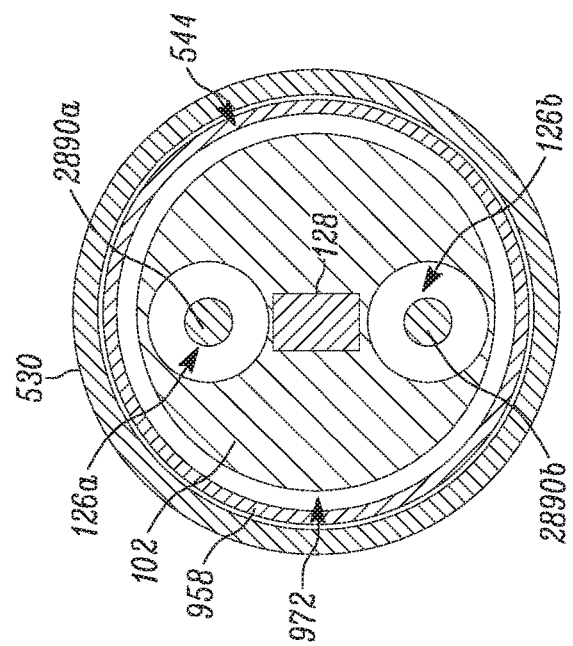
Figure 31B:
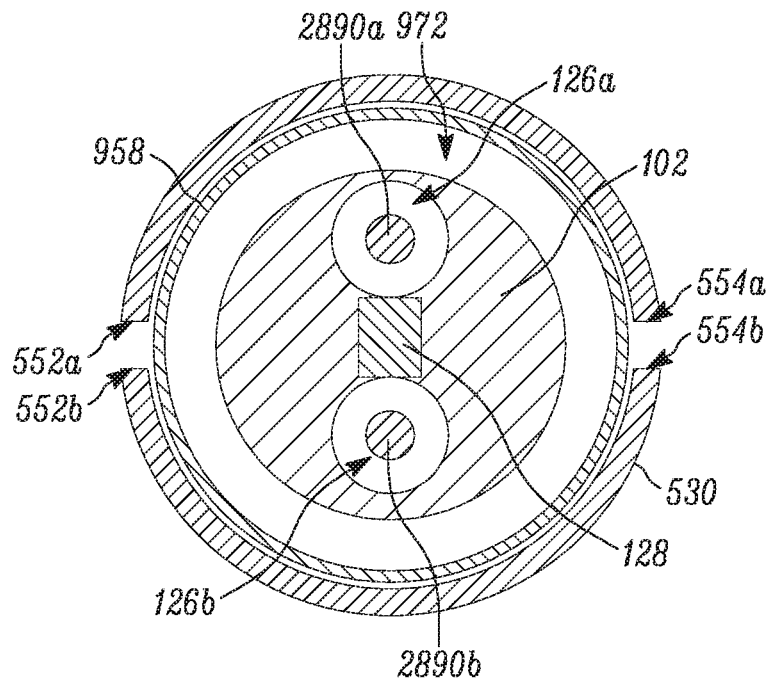
Figure 31C:
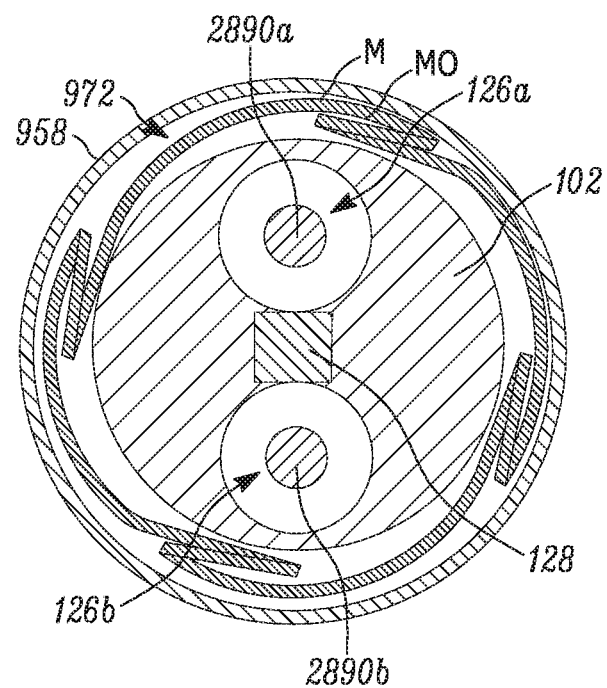
Figure 31D:
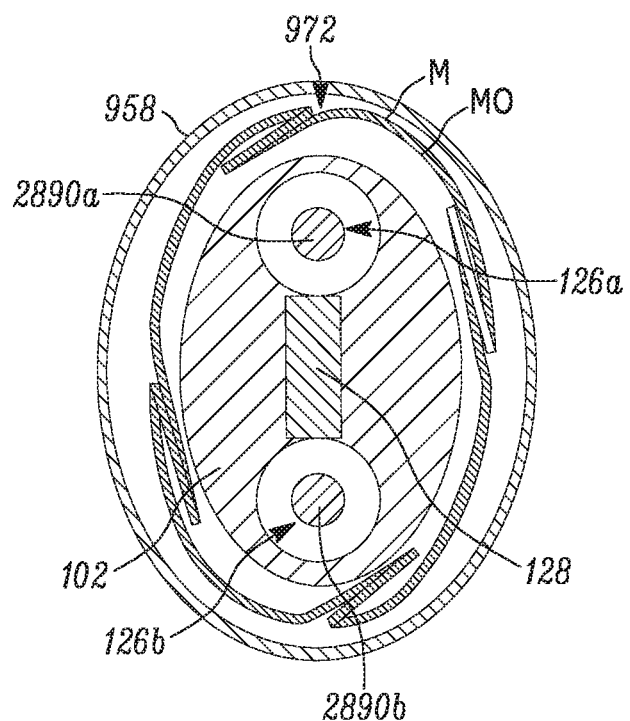
Figure 31E:
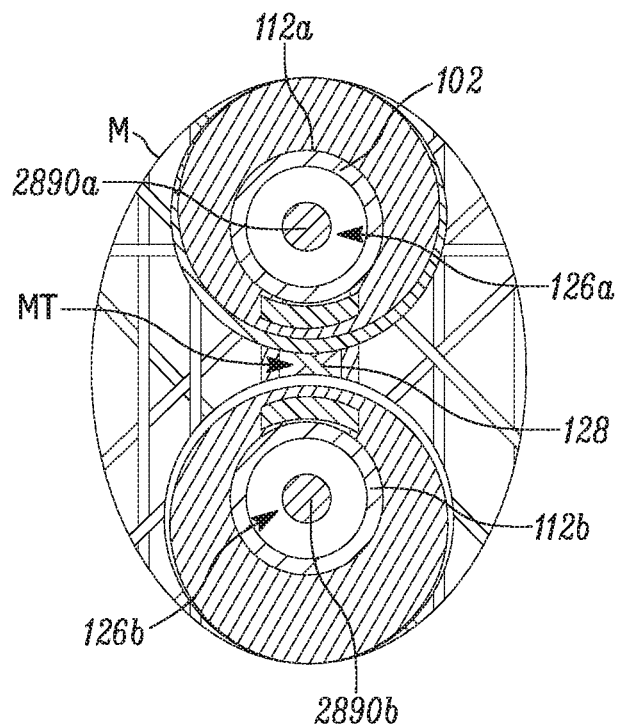
Figure 31G:
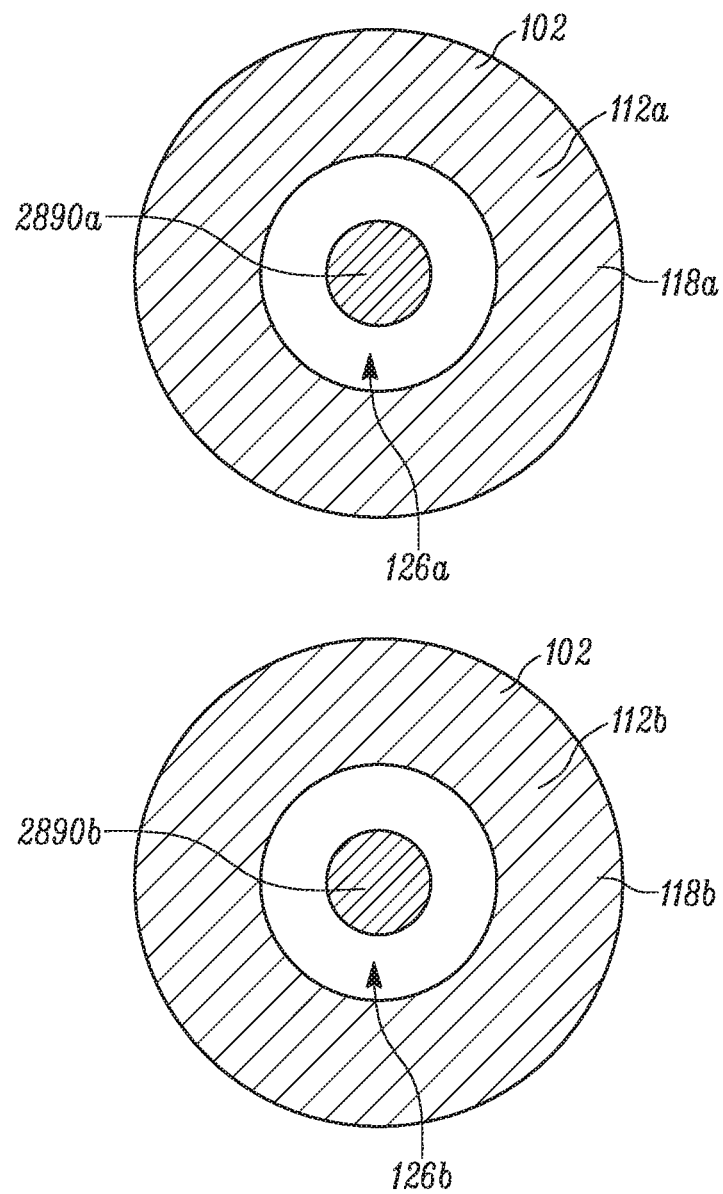

As shown in FIGS. 30-31, with the implant delivery system 100 positioned at the target patient tissue site T, at least a portion of the bifurcated expandable implant M may be exposed by urging the outer sheath 530 in the longitudinally proximal direction (shown as an arrow "Y" in FIG. 30-31). In particular, the expandable implant branches MB-a, MB-b may be exposed by urging the outer sheath 530 in the longitudinally proximal direction. Movement of the outer sheath 530 in the longitudinally proximal direction may cause at least one of the expandable implant branches MB-a, MB-b, the shaft branches 112a, 112b, and the open slit cover members 1274a, 1274b, 1274c, 1274d, when provided, to move along a respective outer sheath open slit 548a, 548b to selectively elastically separate a respective outer sheath open slit first surface 552a, 552b from a respective outer sheath open slit second surface 554a, 554b and accordingly permit the outer sheath 530 to be directed in the longitudinally proximal direction. The elastic separation caused by at least one of the expandable implant branches MB-a, MB-b, the shaft branches 112a, 112b, and the open slit cover members 1274a, 1274b, 1274c, 1274d, when provided, moving along a respective outer sheath open slit 548a, 548b can be thought of as an "unzipping"-type process.

While the outer sheath is urged in the longitudinally proximal direction, at least a portion of the implant delivery system 100 and the bifurcated expandable implant M may be maintained in position at the target patient tissue site T. In particular, the at least two guidewires 2890a, 2890b, the inner sheath 958, the expandable implant body MO, and the shaft body 108 may be maintained at the patient lumen main portion LP. Each of the guidewire distal ends 2888a, 2888b, the expandable implant branches MB-a, MB-b, and the shaft branches 112a, 112b may be maintained at the respective patient lumen branches LB-a, LB-b. The reinforcing element distal end 129 and the expandable implant transition portion MT may be maintained at the patient lumen transition portion LT. The contact between the expandable implant transition portion MT and the reinforcing element distal end 129 may at least partially maintain the expandable implant transition portion MT at the patient lumen transition portion LT while the outer sheath 530 is urged in the proximal direction by providing a force in the longitudinally distal direction (shown as an arrow "X" in FIGS. 30-31) against at least a portion of the expandable implant transition portion MT. FIG. 30a-g depict cross-sectional views of various points along the implant delivery system 100, to show the arrangement of the outer sheath 530, the inner sheath 758, the shaft 102, and the bifurcated expandable implant M in FIG. 30.

As shown in FIG. 31, with at least a portion of the bifurcated expandable implant M exposed (such as the expandable implant branches Mb-a, MB-b, as depicted in FIG. 31), the properties of the bifurcated expandable implant M may be utilized to move the exposed portion of the bifurcated expandable implant M toward the expanded condition. FIG. 31a-g depict cross-sectional views of various points along the implant delivery system 100, to show the arrangement of the outer sheath 530, the inner sheath 758, the shaft 102, and the bifurcated expandable implant M in FIG. 31.

As shown in FIG. 32, with the expandable implant branches MB-a, MB-b exposed, the bifurcated expandable implant body MO may be exposed by urging the inner sheath 958 in the longitudinally proximal direction. While the inner sheath 958 is urged in the longitudinally proximal direction, at least a portion of the implant delivery system 100 and the bifurcated expandable implant M may be maintained in position at the target patient tissue site T. In particular, the at least two guidewires 2890a, 2890b, the expandable implant body MO, and the shaft body 108 may be maintained at the patient lumen main portion LP. The guidewire distal ends 2888a, 2888b, the expandable implant branches MB-a, MB-b, and the shaft branches 112a, 112b may be maintained at the respective patient lumen branches LB-a, LB-b. The reinforcing element distal end 129 and the expandable implant transition portion MT may be maintained at the patient lumen transition portion LT. The contact between the expandable implant transition portion MT and the reinforcing element distal end 129 at least partially maintains the expandable implant transition portion MT at the patient lumen transition portion LT while the inner sheath 958 is urged in the proximal direction by providing a force in the longitudinally distal direction (shown as an arrow "X" in FIG. 32) against at least a portion of the expandable implant transition portion MT.

Figure 32B:
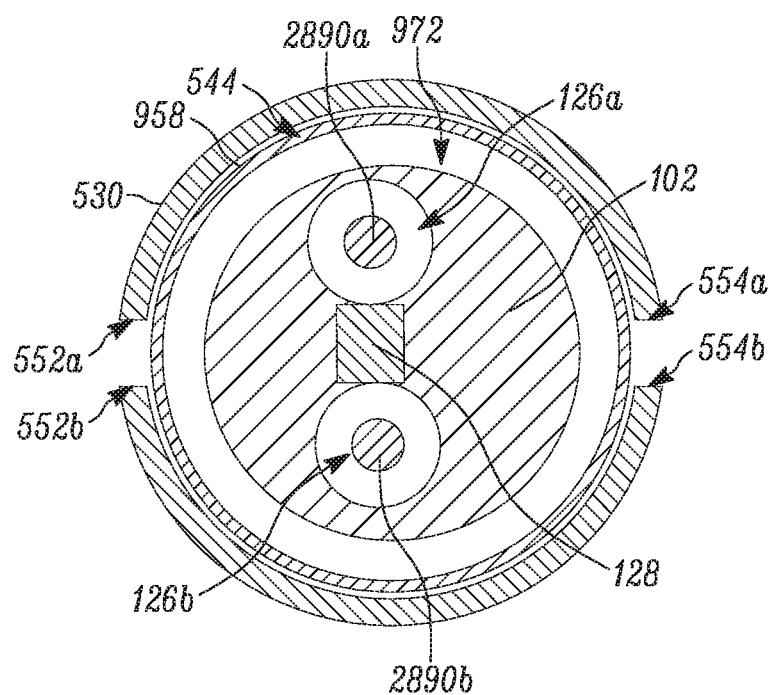
Figure 32C:
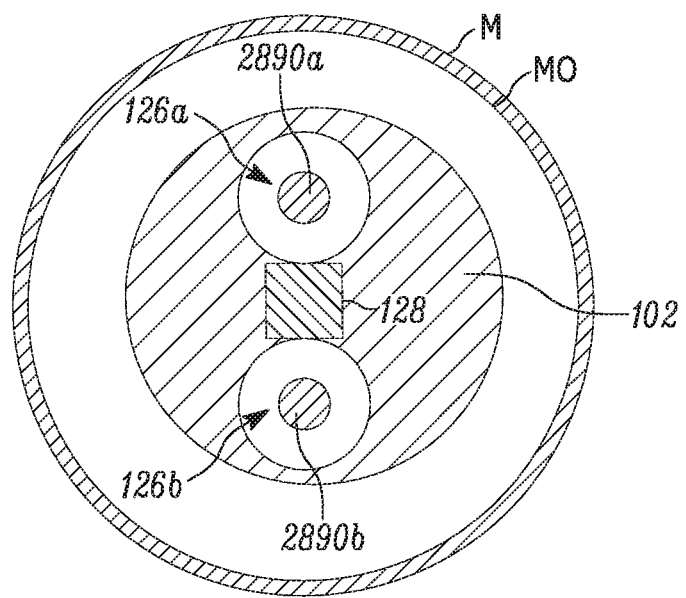
Figure 32F:
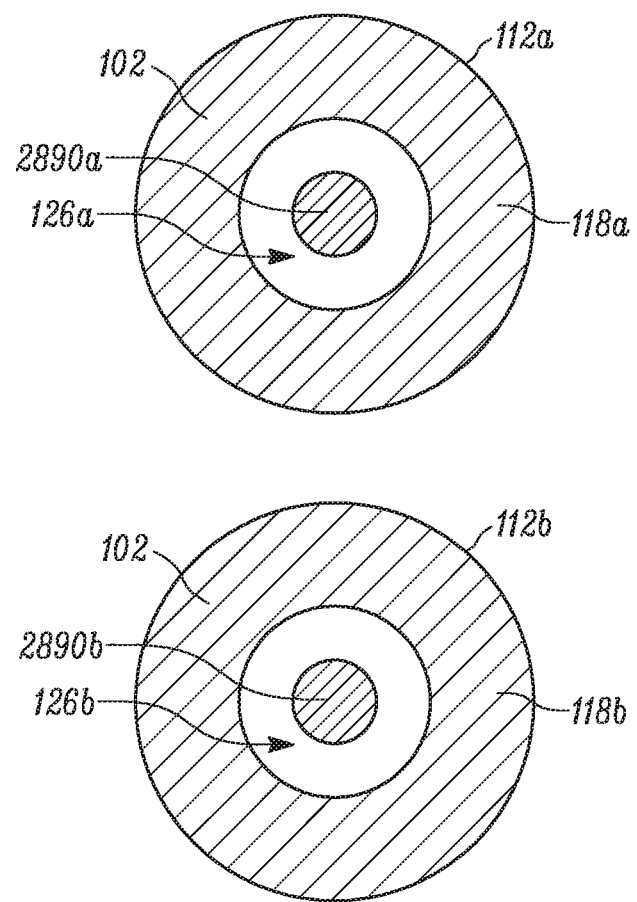
Figure 33:
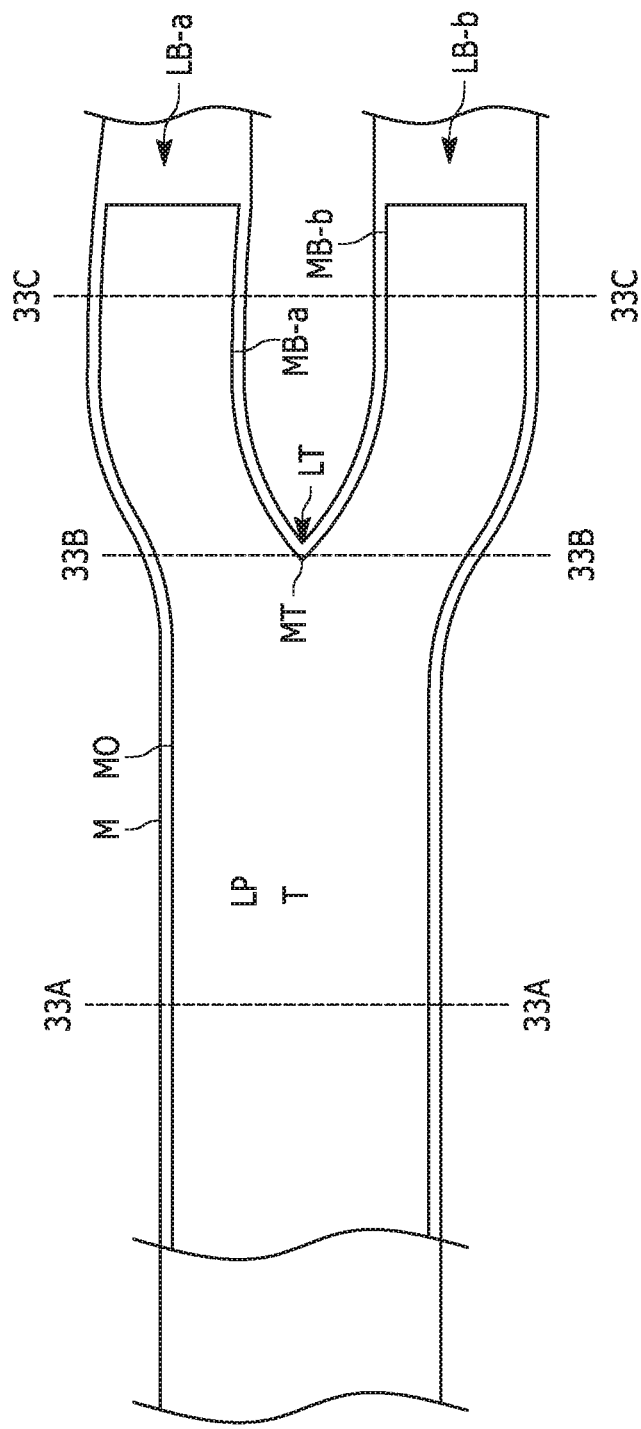
Figure 33A:
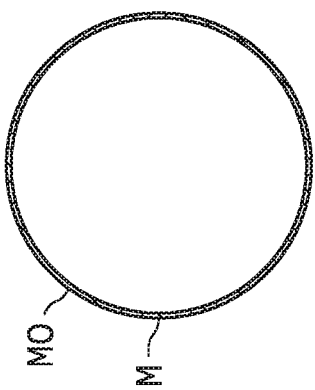

As shown in FIGS. 32-33, with at least a portion of the bifurcated expandable implant M exposed (such as the expandable implant branches Mb-a, MB-b and the expandable implant body MO), the properties of the bifurcated expandable implant M may be utilized to move the exposed portion of the bifurcated expandable implant M toward the expanded condition. FIG. 32a-f depict cross-sectional views of various points along the implant delivery system 100, to show the arrangement of the outer sheath 530, the inner sheath 758, the shaft 102, and the bifurcated expandable implant M in FIG. 32. As depicted in FIG. 33, with the bifurcated expandable implant M in the expanded condition, the outer sheath 530, the shaft 102, the inner sheath 958, and/or the at least one guidewire 2890a, 2890b, may be removed from at least one of the target patient tissue site T, the patient lumen main portion LP, and at least one of the patient lumen branches LB-a, LB-b. FIGS. 33a-c depict cross-sectional views of various points along the expanded bifurcated expandable implant M in FIG. 32.

Figure 35:
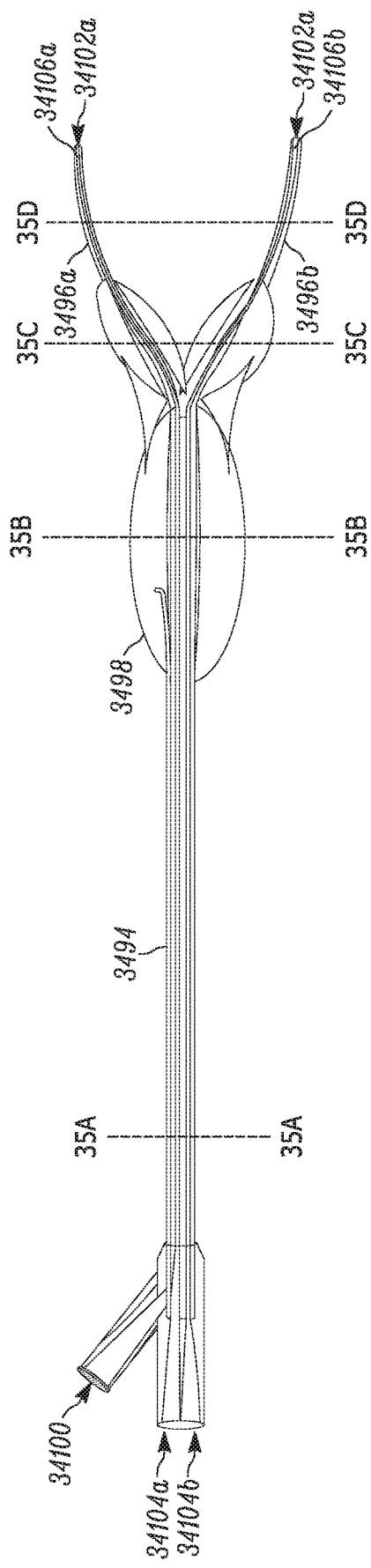
Figure 35A:
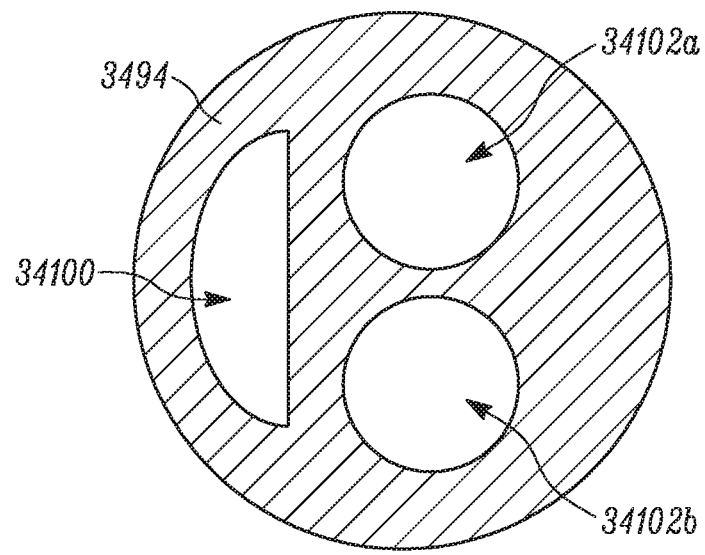
Figure 35B:
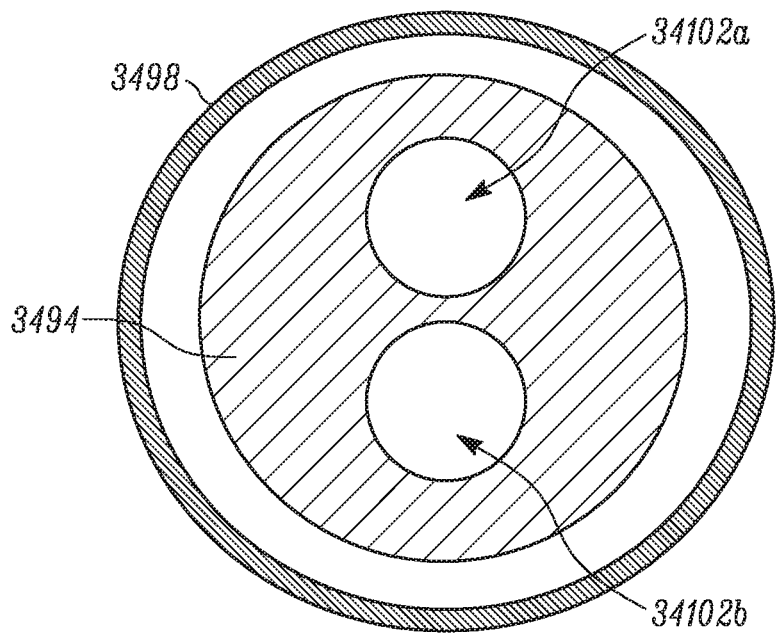

Alternatively, after the outer sheath 530, the shaft 102, and the inner sheath 958 have been removed, a secondary device may be directed over at least one of the guidewires 2890a, 2890b to perform a medical procedure with the secondary device at the target patient tissue site T, the patient lumen main portion LP, and/or at the one of the patient lumen branches LB-a, LB-b. As shown in FIGS. 34-35, the secondary device may be a balloon dilation device 3494 having at least two balloon dilation device branches 3496 (shown here as balloon dilation device branches 3496a and 3496b), a bifurcated expandable balloon 3498, and a balloon inflation channel 34100 for directing inflation fluid to the bifurcated expandable balloon 3498. As shown in FIG. 34, the balloon dilation device 3494 may have a single balloon dilation device lumen 34102 that longitudinally extends between a balloon dilation device proximal opening 34104 and each balloon dilation device open tip 34106 (shown here as balloon dilation device open tips 34106a and 34106b) of the balloon dilation device branches 3496a, 3496b. FIGS. 34a-d depict cross-sectional views of various points along the balloon dilation device 3494, to show the structural features of the balloon dilation device 3494, as depicted in FIG. 34. As shown in FIG. 35, the balloon dilation device 3494 may have at least two balloon dilation device lumens 34102 (shown here as balloon dilation device lumens 34102a and 34102b) that longitudinally extend between respective balloon dilation device proximal openings 34104 (shown here as balloon dilation device proximal openings 34104a and 34104b) and respective balloon dilation device open tips 34106a, 34106b. FIGS. 35a-d depict cross-sectional views of various points along the balloon dilation device 3494, to show the structural features of the balloon dilation device 3494, as depicted in FIG. 35.

Figure 36:
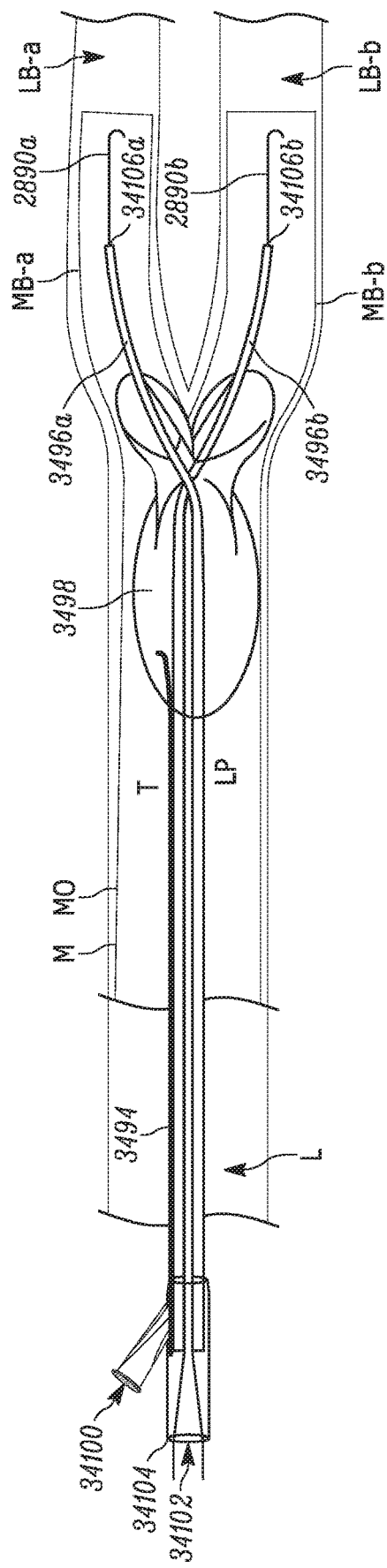
Figure 37:
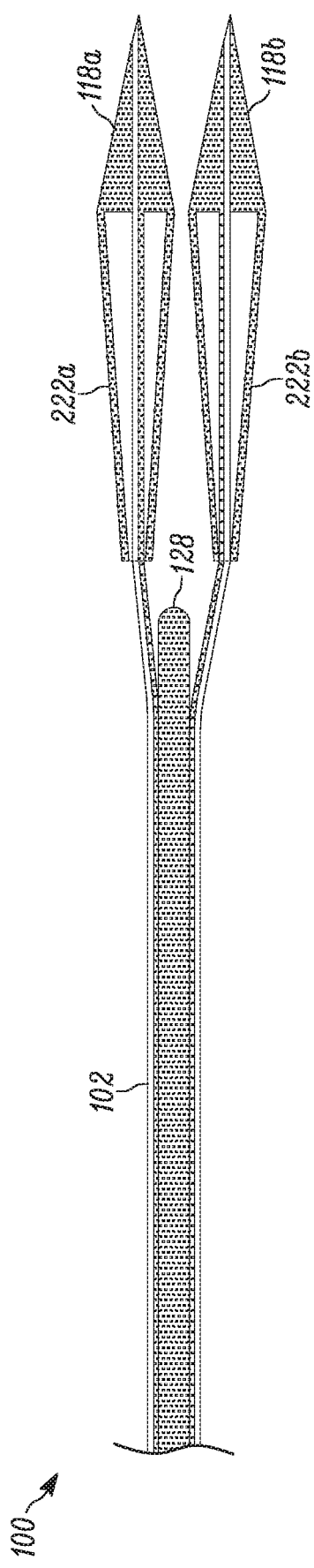

As shown in FIG. 36, the balloon dilation device 3494 may be directed along the at least two guidewires 2890a, 2890b and positioned with at least a portion of the bifurcated expandable balloon 3498 within a diseased segment of the patient lumen L and/or adjacent to an inner surface of the bifurcated expandable implant M. The bifurcated expandable balloon 3498 may be inflated to dilate the diseased segment of the patient lumen L and/or cause the expandable implant M to further expand. With the expandable implant M further expanded, the expandable balloon 3498 may be deflated. At least one of the balloon dilation device 3494 and the at least two guidewires 2890a, 2890b may then be removed from the target patient tissue site T, the patient lumen main portion LP, and/or at least one of the patient lumen branches LB-a, LB-b by moving at least one of the balloon dilation device 3494 and at least one of the guidewires 2890a, 2890b in the longitudinally proximal direction.

Although the above description of the example sequence of operation for the implant delivery system 100 of FIG. 17, one of ordinary skill in the art will understand, given the teachings of the present application, how to operate any configuration for the shaft 1030, the inner sheath 958, when provided, and the outer sheath 102 similarly. For example, FIGS. 37-48 depict an example sequence of operation of the bifurcated implant delivery system 100, as depicted in FIG. 18. The at least one bifurcated expandable implant M, which can be self-expandable and/or expand through external means (e.g., a balloon), is provided.

Figure 38:
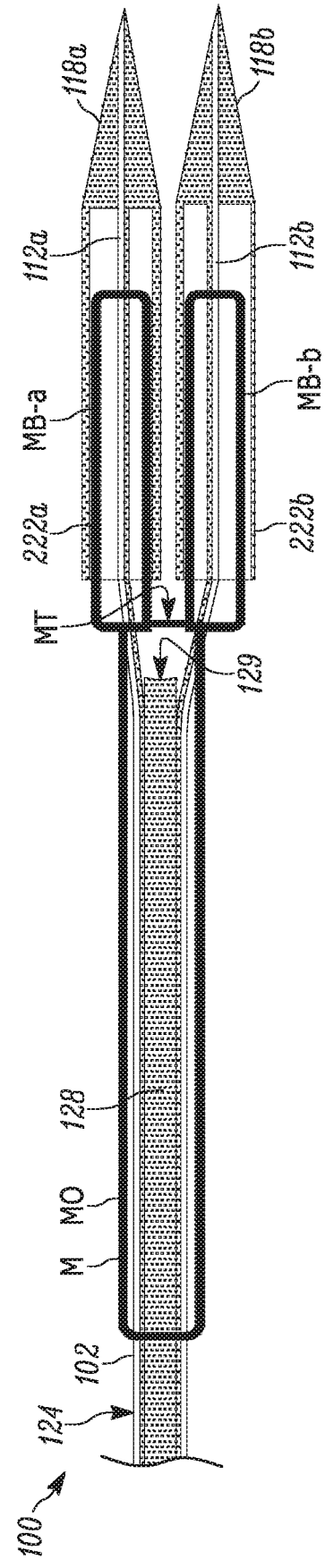

As shown in FIG. 38, a collapsed expandable implant M may be placed in operative engagement with the shaft outer surface 124. In particular, a collapsed bifurcated expandable implant M may be circumferentially mounted on the shaft outer surface 124 with the expandable implant body MO circumferentially mounted on at least a portion of the shaft body 108, each of the expandable implant branches MB-a, MB-b circumferentially mounted on a respective shaft branch 112*a*, 112*b*, and at least a portion of the expandable implant transition portion MT being longitudinally spaced from a reinforcing element distal end 129. Each elastic skirt 222*a*, 222*b* may be operatively engaged to a respective collapsed expandable implant branch MB-a, MB-b by placing each elastic skirt 222*a*, 222*b* on at least a portion of the collapsed respective expandable implant branch MB-a, MB-b.

As shown in FIG. 39, with the collapsed bifurcated expandable implant mounted M on the shaft 102, at least a portion of the collapsed expandable implant body MO and at least a portion of the shaft body 108 may be operatively engaged to the inner sheath 958, such as by being collectively inserted into at least a portion of the inner sheath lumen 972. As shown in FIG. 40, at least a portion of the inner sheath 958, at least a portion of the collapsed bifurcated expandable implant M, and at least a portion of the shaft 102 may be operatively joined to the outer sheath 530, such as by being collectively inserted into at least a portion of the outer sheath lumen 544.

Figure 41:
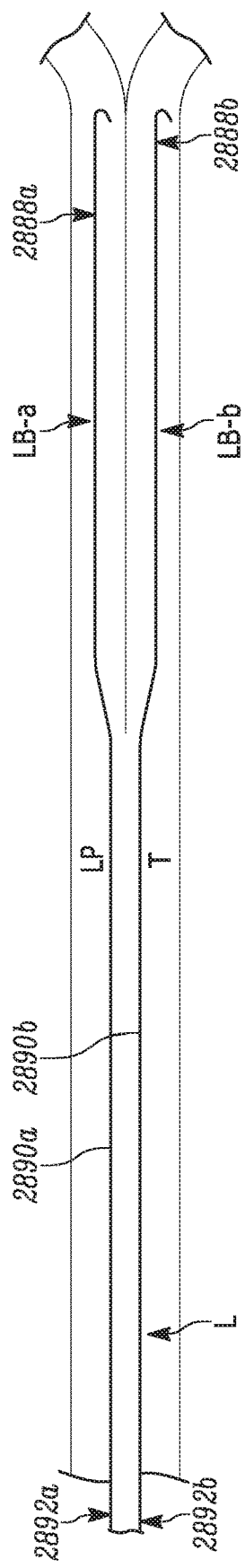
Figure 42:
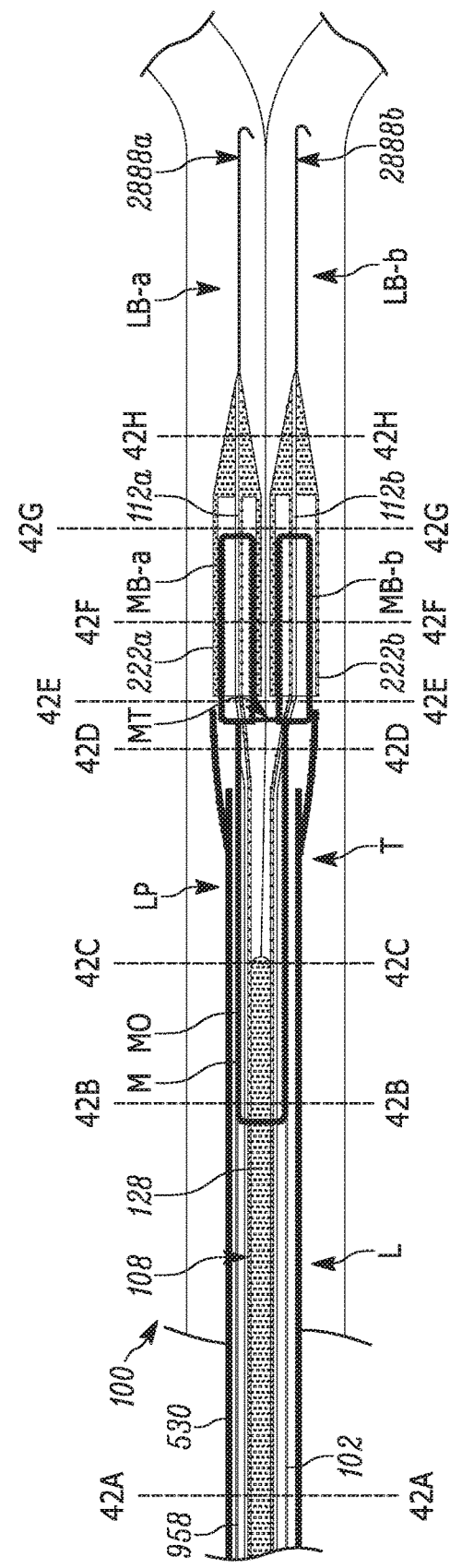
Figure 42A:
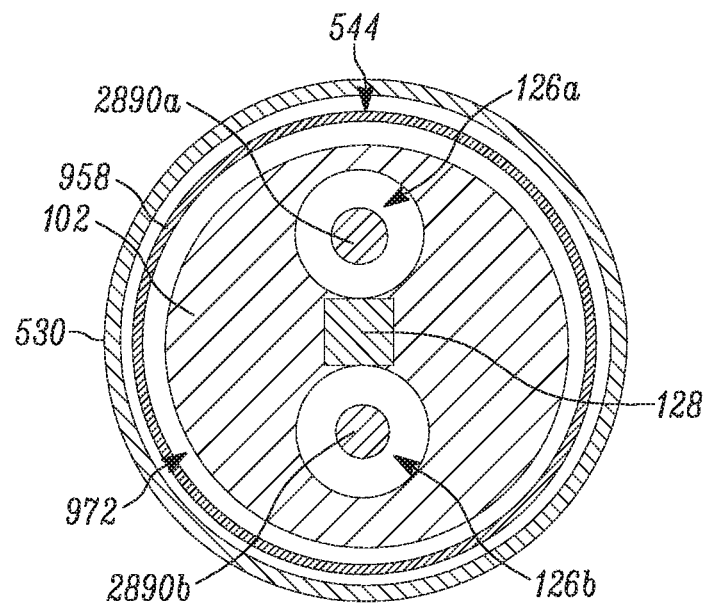
Figure 42B:
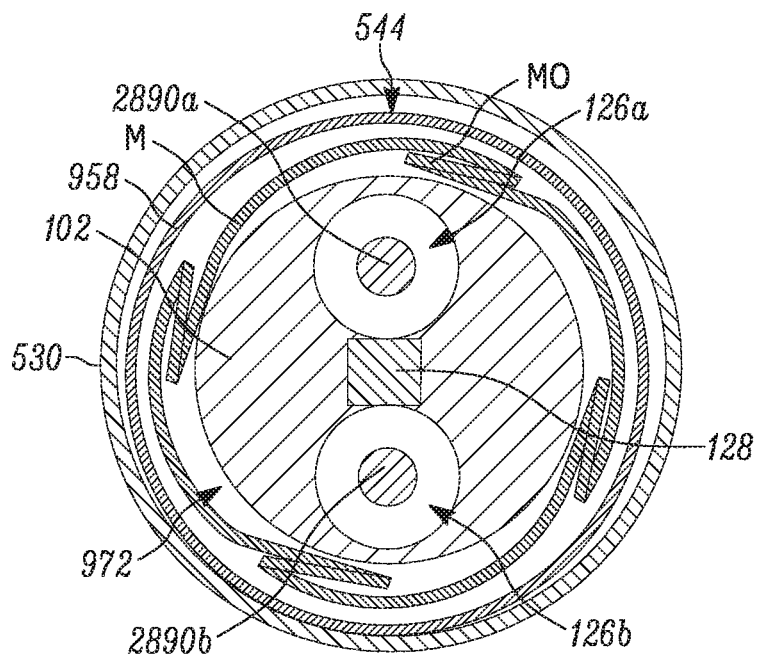
Figure 42C:
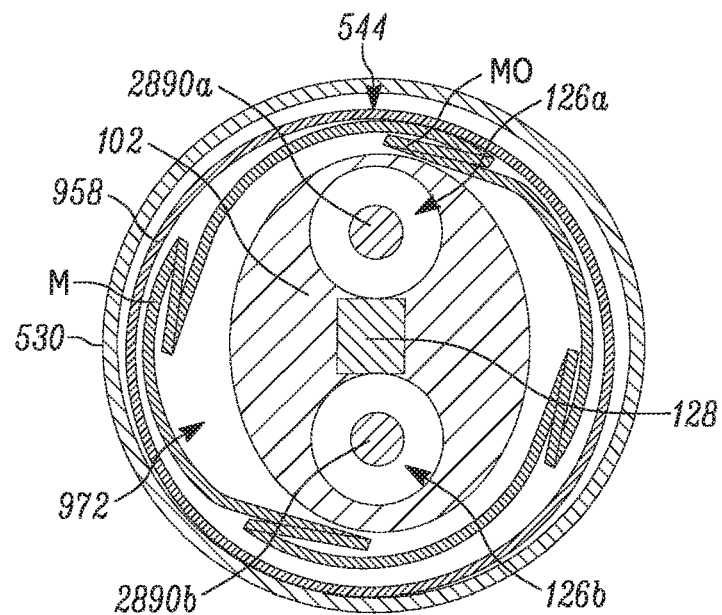
Figure 42D:
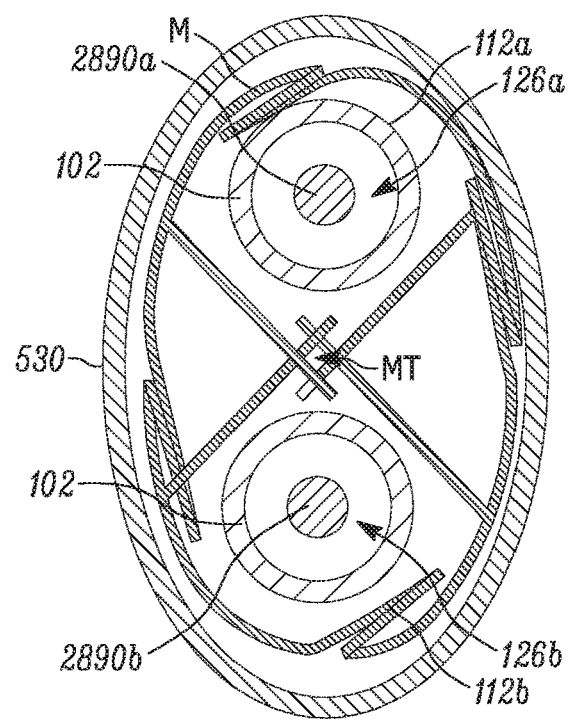
Figure 42F:
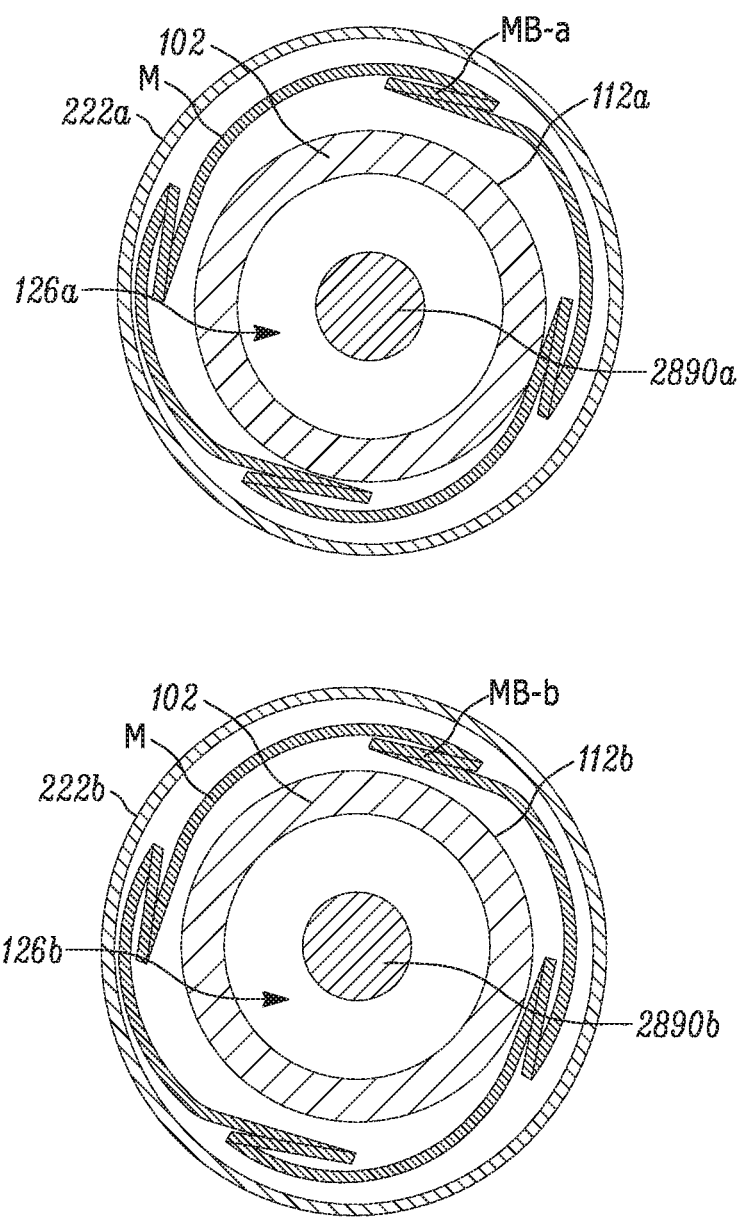
Figure 42G:
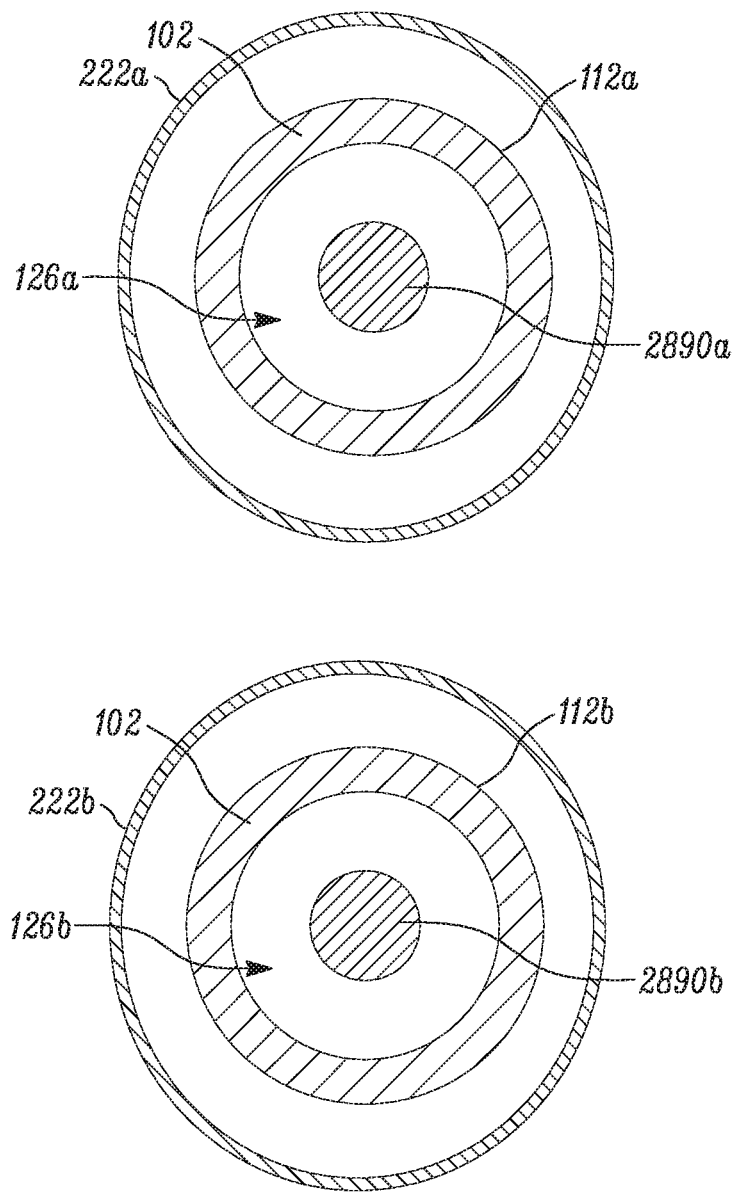

As depicted in FIG. 41, at least two guidewire distal ends 2888*a*, 2888*b* may be inserted into a target patient tissue site T in a patient lumen L with each guidewire distal end 2888*a*, 2888*b* of at least two guidewires 2890*a*, 2890*b* being positioned in a respective patient lumen branch LB-a, LB-b. Each guidewire proximal end 2892*a*, 2892*b* of the at least two guidewires 2890*a*, 2890*b* are directed through the implant delivery system 100 by being directed through the at least one shaft lumen 126, such as through a respective shaft lumen 126*a*, 126*b*. As shown in FIG. 42, the implant delivery system 100 may be directed to the target patient tissue site T along the at least two guidewires 2890*a*, 2890*b*.

As shown in FIG. 42, the implant delivery system 100 may be positioned at the target patient tissue site T. In particular, at least a portion of the outer sheath 530, at least a portion of the inner sheath 958, at least a portion of the shaft body 108, and at least a portion of the expandable implant body MO may be positioned in a patient lumen main portion LP. At least a portion of each shaft branch 112*a*, 112*b* and at least a portion of each expandable implant branch MB-a, MB-b may be positioned in a respective patient lumen branch LB-a, LB-b. At least a portion of the expandable implant transition portion MT may be positioned at a patient lumen transition portion LT. FIG. 42*a-h* depict cross-sectional views of various points along the implant delivery system 100, to show the arrangement of the outer sheath 530, the inner sheath 758, the shaft 102, and the bifurcated expandable implant M in FIG. 42.

Figure 43:
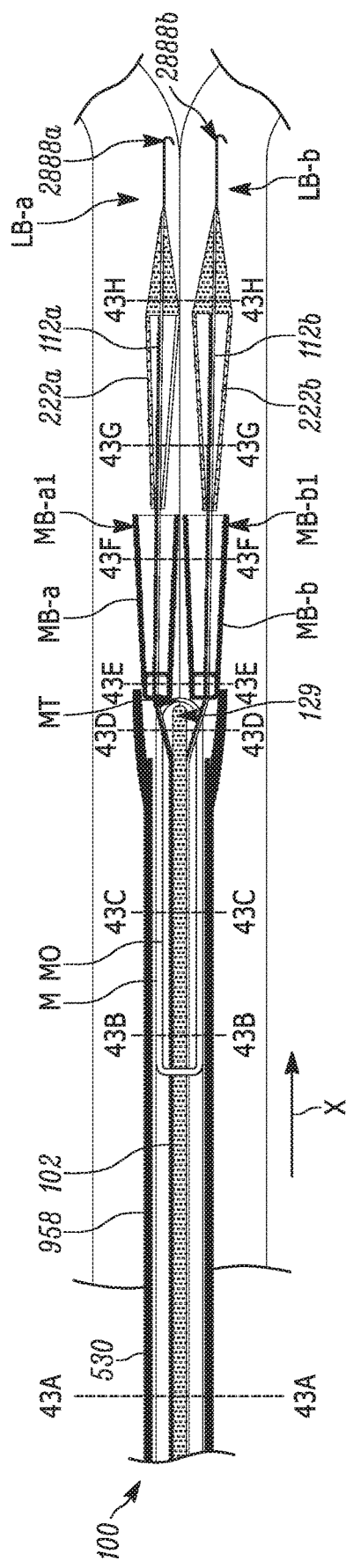
Figure 43A:
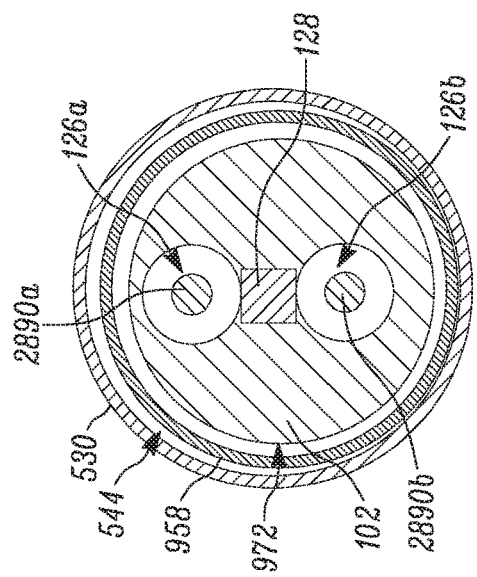
Figure 43B:
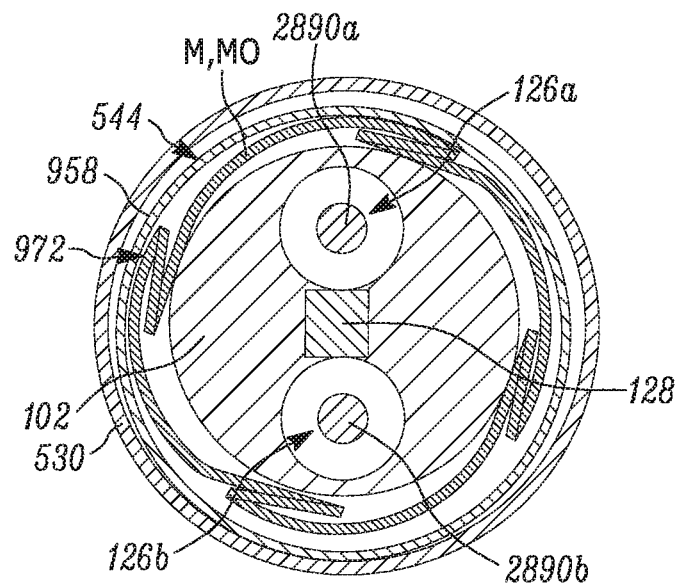
Figure 43C:
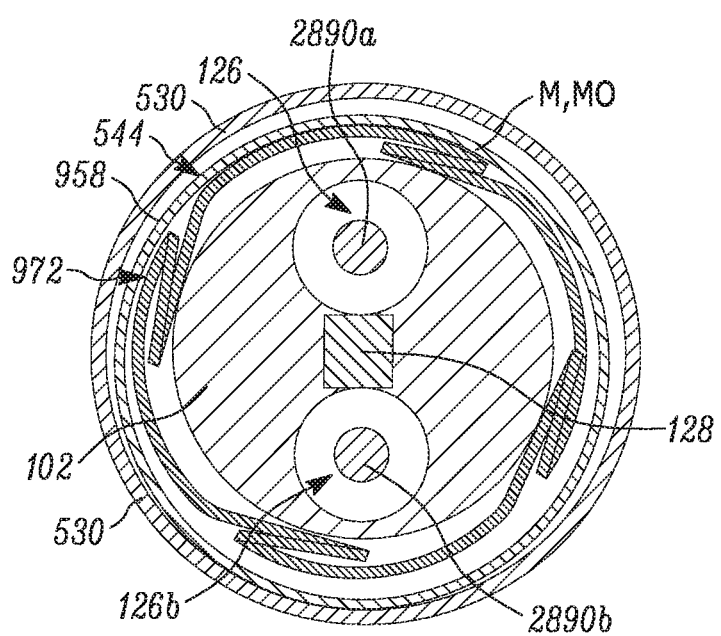
Figure 43F:
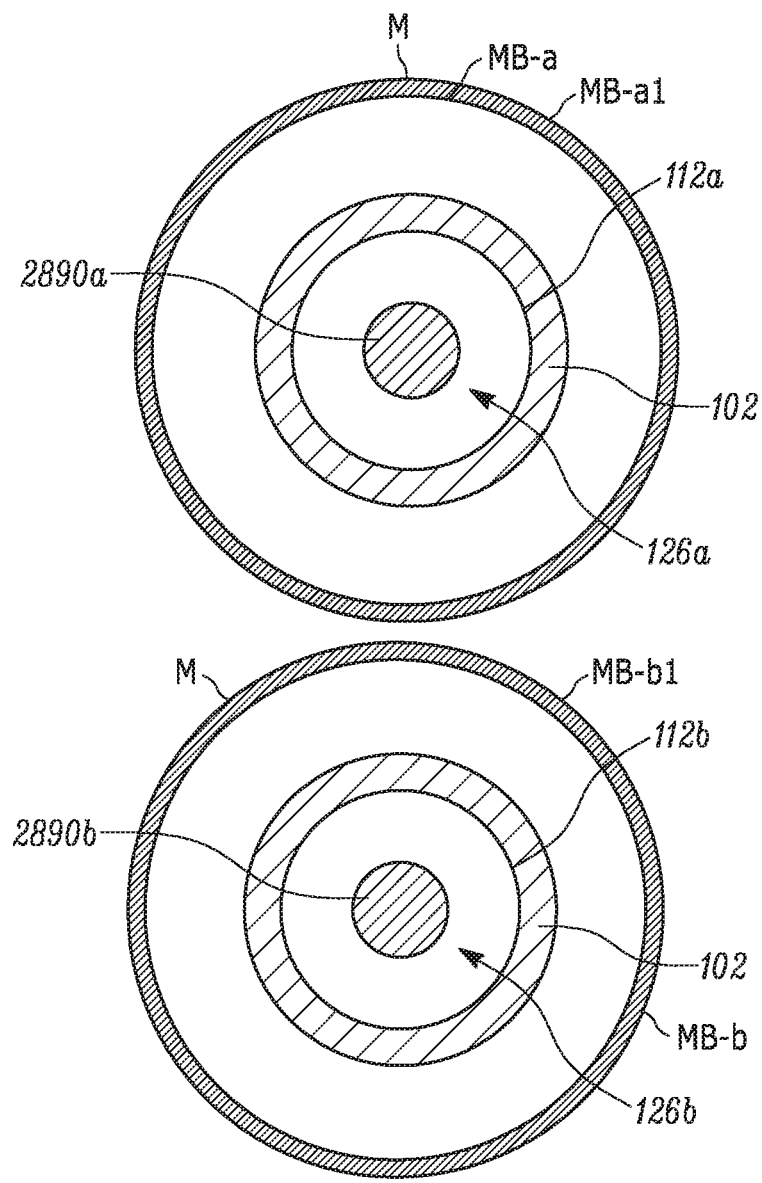
Figure 43H:
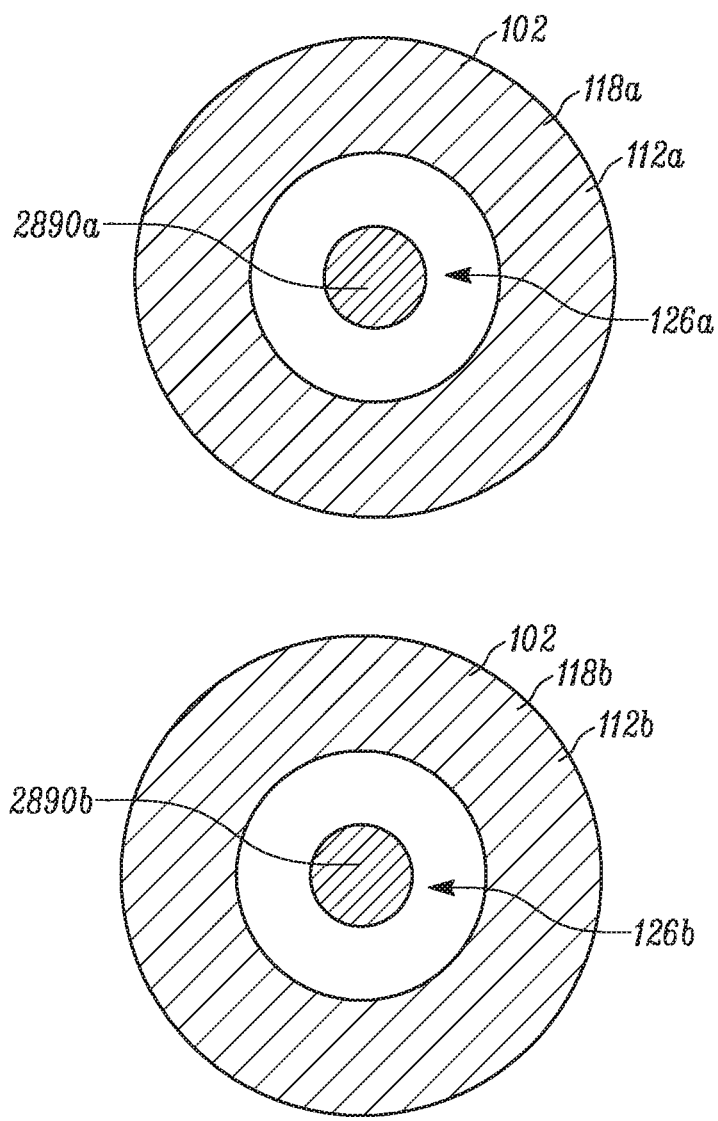

As shown in FIG. 43, with the implant delivery system 100 positioned at the target patient tissue site T, at least a portion of the bifurcated expandable implant M may be exposed by urging the shaft 102 in the longitudinally distal direction (shown as an arrow "X" in FIG. 43). In particular, a first portion of the expandable implant branches MB-a1, MB-b1 may be exposed by urging the shaft 102 in the longitudinally distal direction. Movement of the shaft 102 in the longitudinally distal direction may cause each of the elastic skirts 222*a*, 222*b* to operatively disengage the respective expandable implant branch MB-a, MB-b. With at least a portion of the bifurcated expandable implant M exposed (such as the first portion of the expandable implant branches Mb-a1, MB-b1, as depicted in FIG. 43), the properties of the bifurcated expandable implant M may be utilized to move the exposed portion of the bifurcated expandable implant M toward the expanded condition. Further, movement of the shaft 102 in the longitudinally distal direction may cause at least a portion of the reinforcing element distal end 129 to at least partially contact the expandable implant transition portion MT. FIGS. 43*a-h* depict cross-sectional views of various points along the implant delivery system 100, to show the arrangement of the outer sheath 530, the inner sheath 758, the shaft 102, and the bifurcated expandable implant M in FIG. 43.

Figure 44:
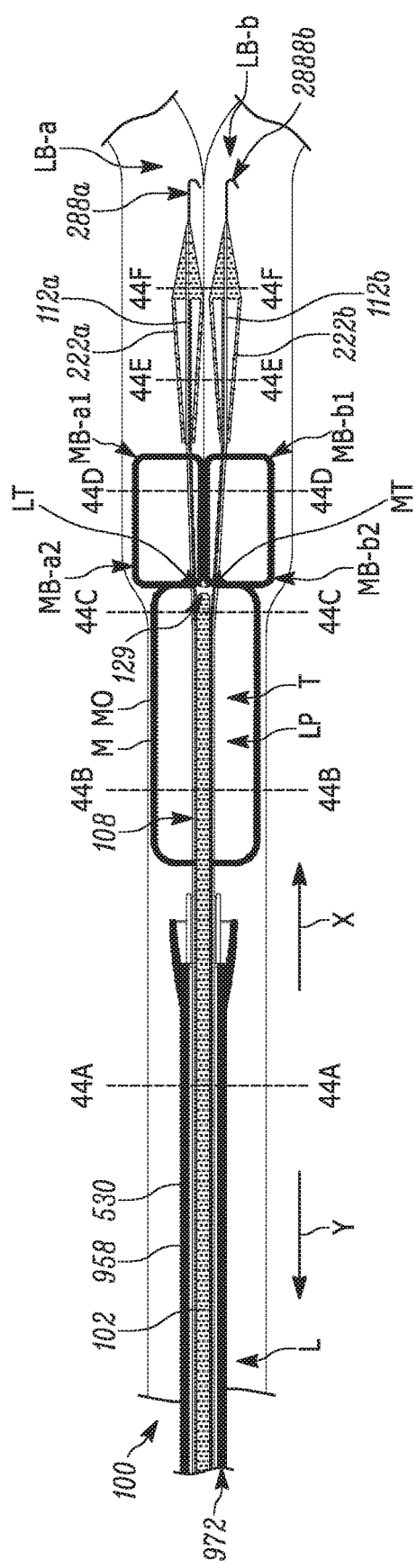
Figure 44A:
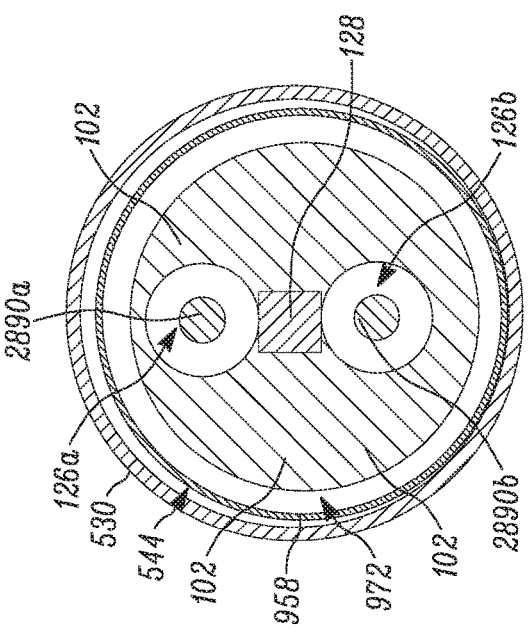
Figure 44B:
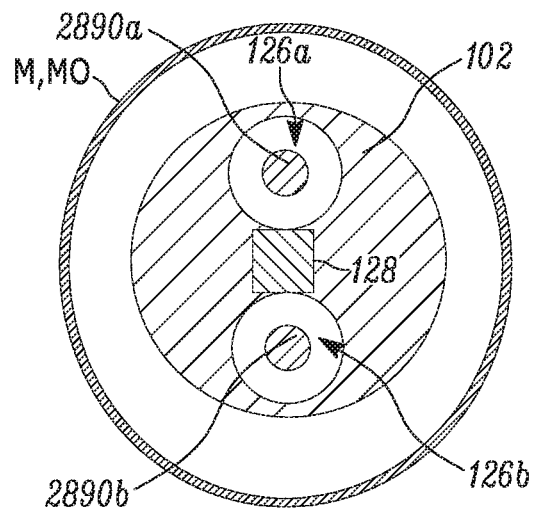
Figure 44C:
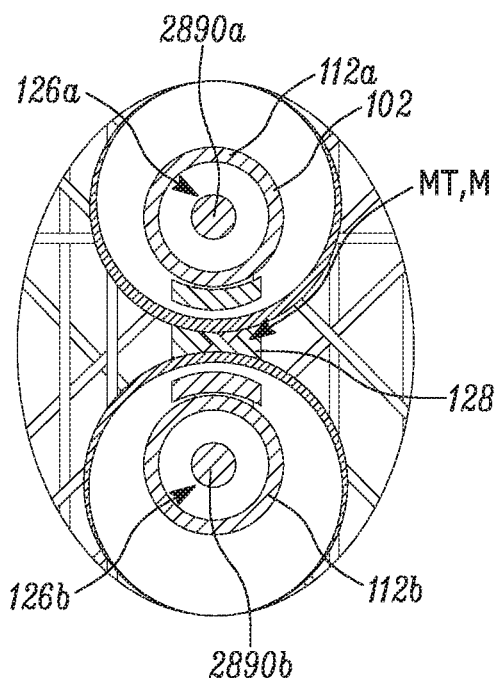
Figure 44D:
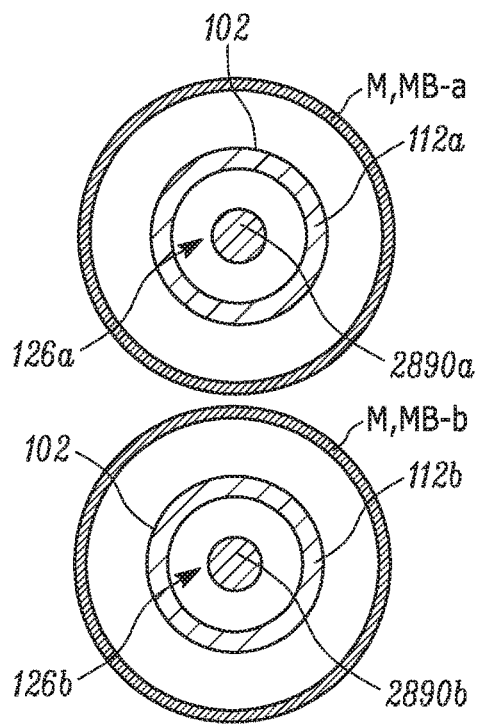
Figure 44E:
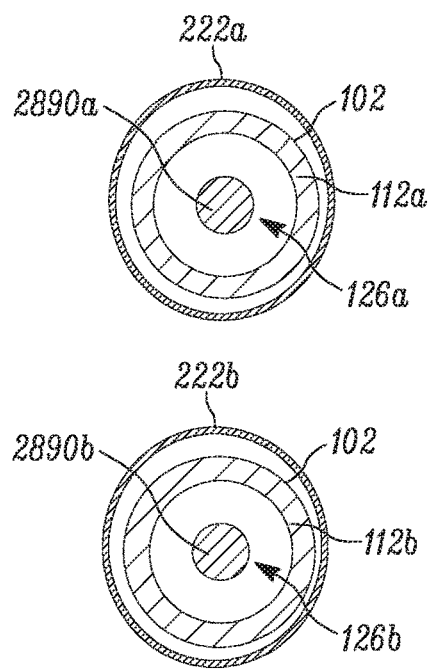

As shown in FIG. 44, with the first portion of the expandable implant branches exposed MB-a1, MB-b1, at least one of a second portion of the expandable implant branches MB-a2, MB-b2 and the expandable implant body MO may be exposed by urging the outer sheath in the longitudinally proximal direction (shown as an arrow "Y" in FIG. 44. While the outer sheath 102 is urged in the longitudinally proximal direction, at least a portion of the implant delivery system 100 and the bifurcated expandable implant M may be maintained in position at the target patient tissue site T. In particular, the at least two guidewires 2890*a*, 2890*b*, the inner sheath 958, the expandable implant body MO, and the shaft body 108 may be maintained at the patient lumen main portion LP. Each of the guidewire distal ends 2888*a*, 2888*b*, the expandable implant branches MB-a, MB-b, and the shaft branches 112*a*, 112*b* may be maintained at the respective patient lumen branches LB-a, LB-b. The reinforcing element distal end 129 and the expandable implant transition portion MT may be maintained at the patient lumen transition portion LT. The contact between the expandable implant transition portion MT and the reinforcing element distal end 129 may at least partially maintain the expandable implant transition portion MT at the patient lumen transition portion LT while the outer sheath 530 is urged in the proximal direction by providing a force in the longitudinally distal direction (shown as an arrow "X" in FIG. 44) against at least a portion of the expandable implant transition portion MT.

If the inner sheath 958 is provided in the implant delivery system 100, the inner sheath 958 may cause at least a portion of the expandable implant body MO disposed within the inner sheath lumen 972 to be restricted/inhibited/prevented from moving toward the expanded condition when the outer sheath 530 is urged the longitudinally proximal direction. In such case, as shown in FIG. 44, with the outer sheath 530 urged in the longitudinally proximal direction, at least a portion of the expandable implant body MO may be exposed by urging the inner sheath 958 in the longitudinally proximal direction.

While the inner sheath 958 is urged in the longitudinally proximal direction, at least a portion of the implant delivery system 100 and the bifurcated expandable implant M may be maintained in position at the target patient tissue site T. In particular, the at least two guidewires 2890*a*, 2890*b*, the expandable implant body MO, and the shaft body 108 may be maintained at the patient lumen main portion LP. The guidewire distal ends 2888*a*, 2888*b*, the expandable implant branches MB-a, MB-b, and the shaft branches 112*a*, 112*b* may be maintained at the respective patient lumen branches LB-a, LB-b. The reinforcing element distal end 129 and the expandable implant transition portion MT may be maintained at the patient lumen transition portion LT. The contact between the expandable implant transition portion MT and the reinforcing element distal end 129 at least partially maintains the expandable implant transition portion MT at the patient lumen transition portion LT while the inner sheath 958 is urged in the proximal direction by providing a force in the longitudinally distal direction against at least a portion of the expandable implant transition portion MT.

As shown in FIG. 44, with at least a portion of the bifurcated expandable implant M exposed (such as the expandable implant branches Mb-a, MB-b and the expandable implant body MO), the properties of the bifurcated expandable implant M may be utilized to move the exposed portion of the bifurcated expandable implant M toward the expanded condition. FIG. 44a-f depict cross-sectional views of various points along the implant delivery system 100, to show the arrangement of the outer sheath 530, the inner sheath 758, the shaft 102, and the bifurcated expandable implant M in FIG. 44.

Figure 45:
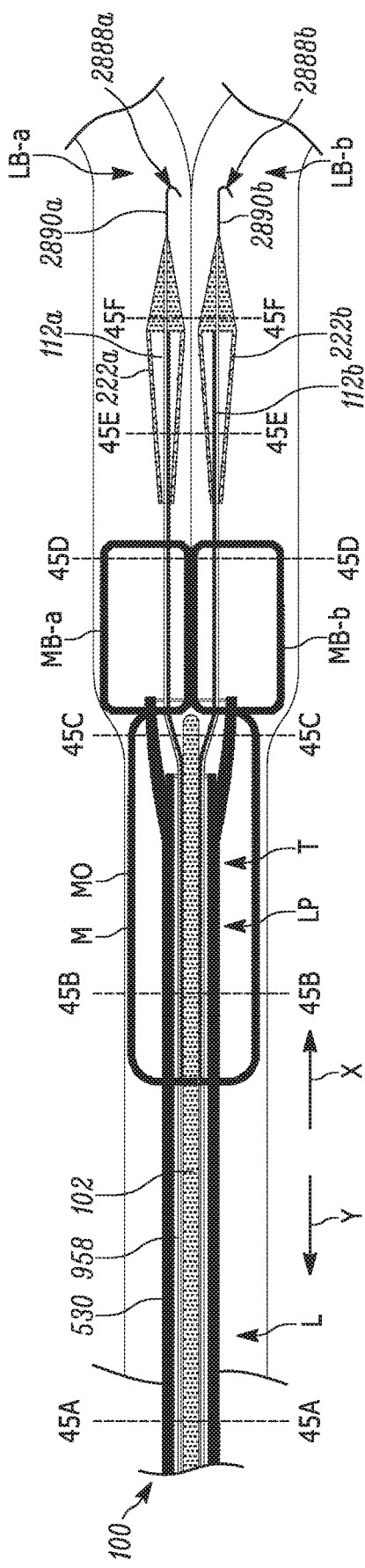
Figure 45A:
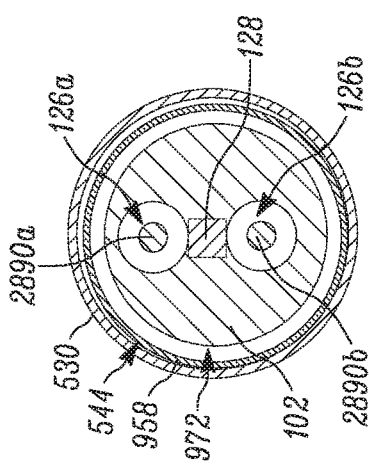
Figure 45B:
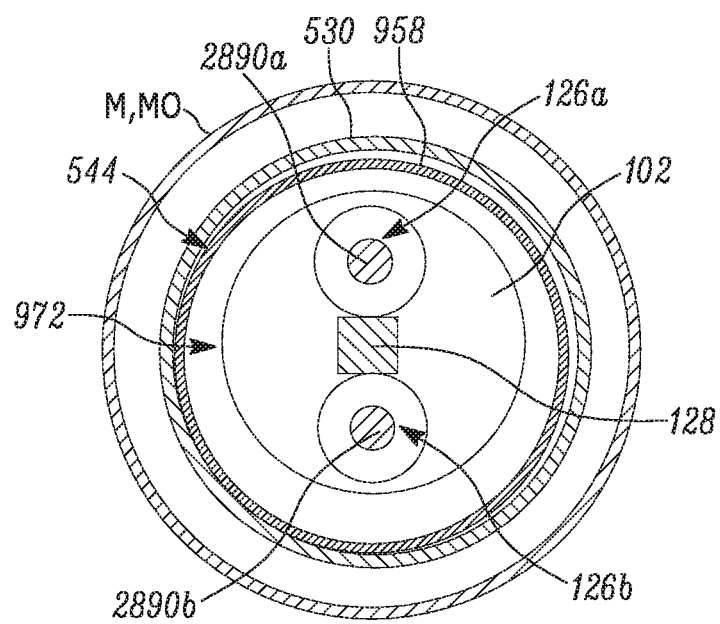
Figure 45C:
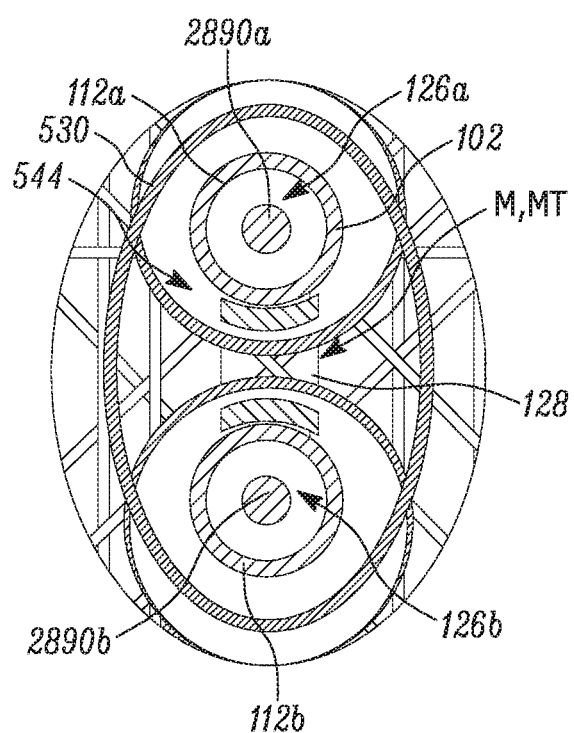
Figure 45D:
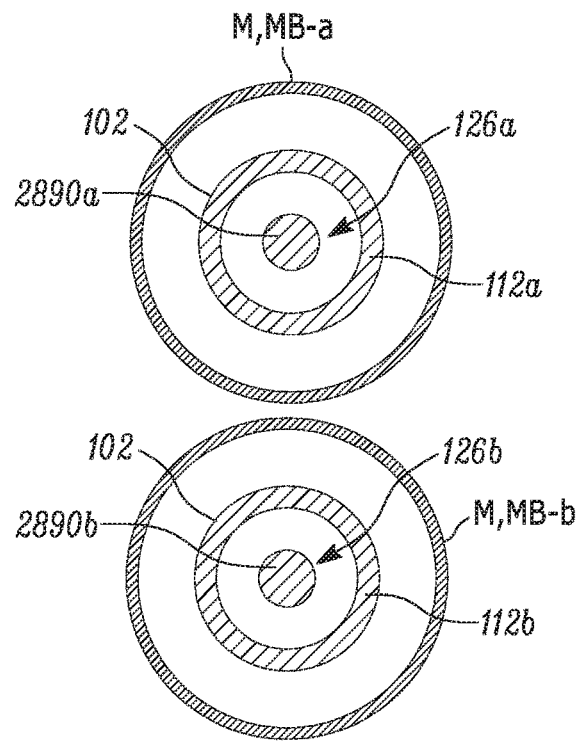
Figure 45E:
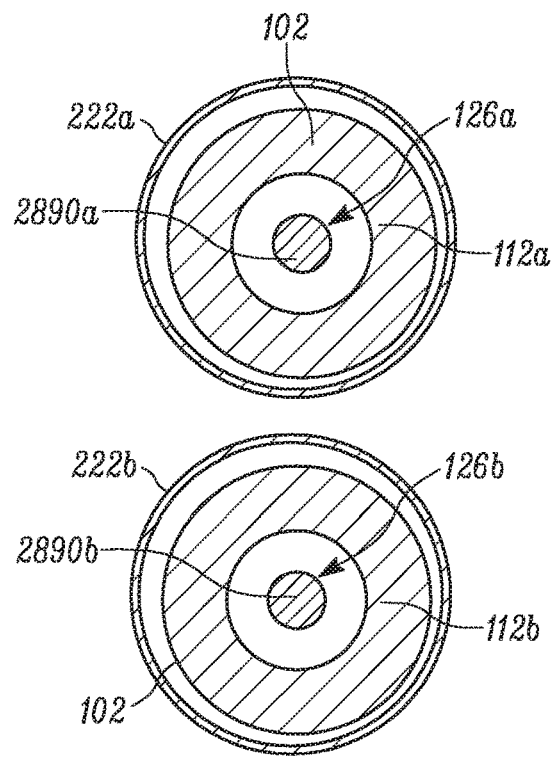
Figure 46B:
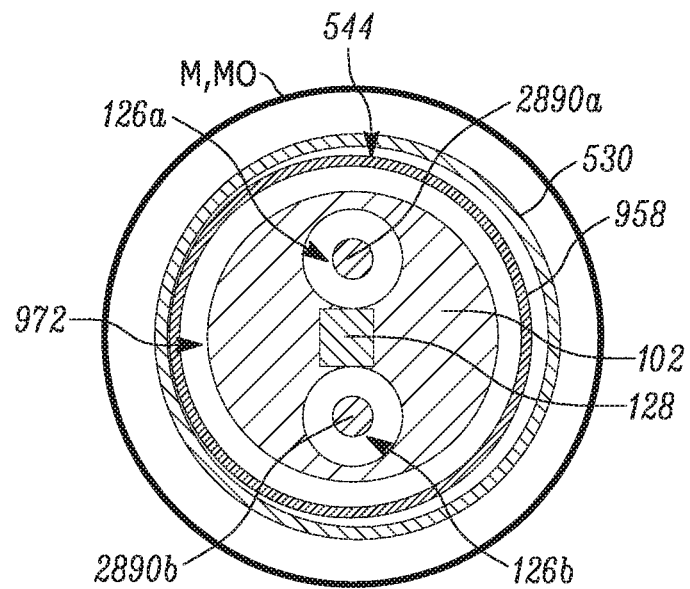
Figure 46C:
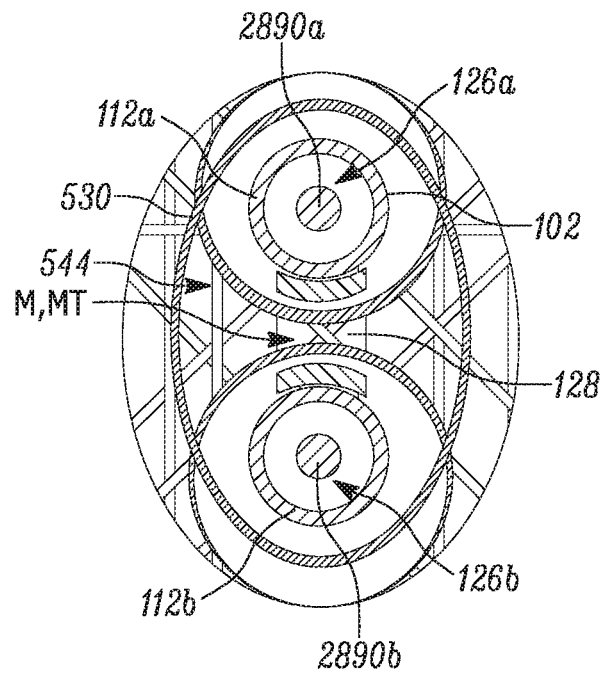
Figure 46D:
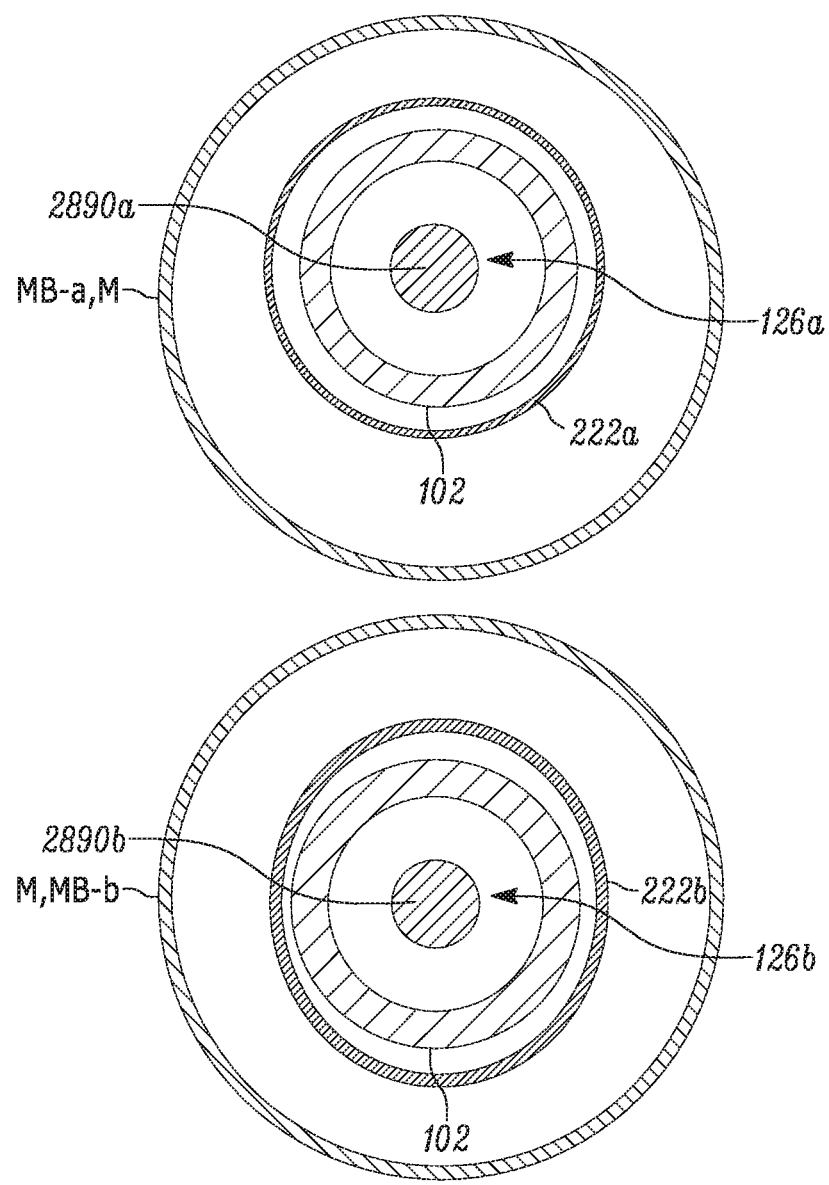
Figure 46E:
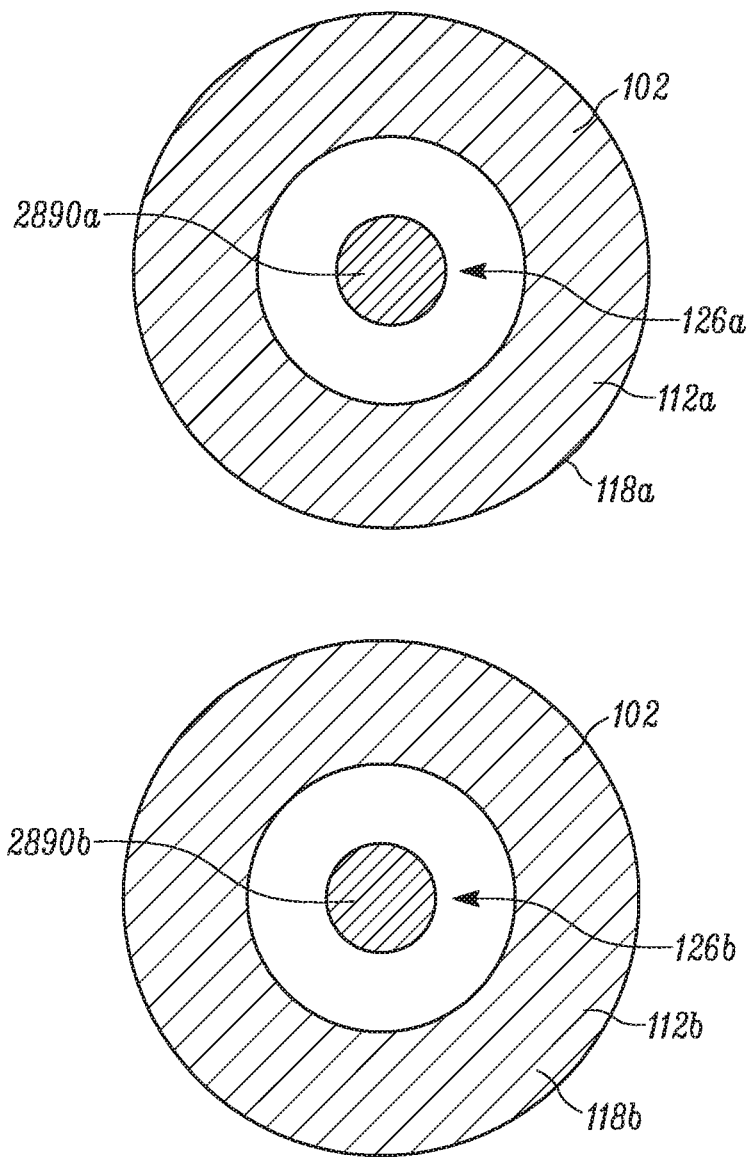
Figure 47:
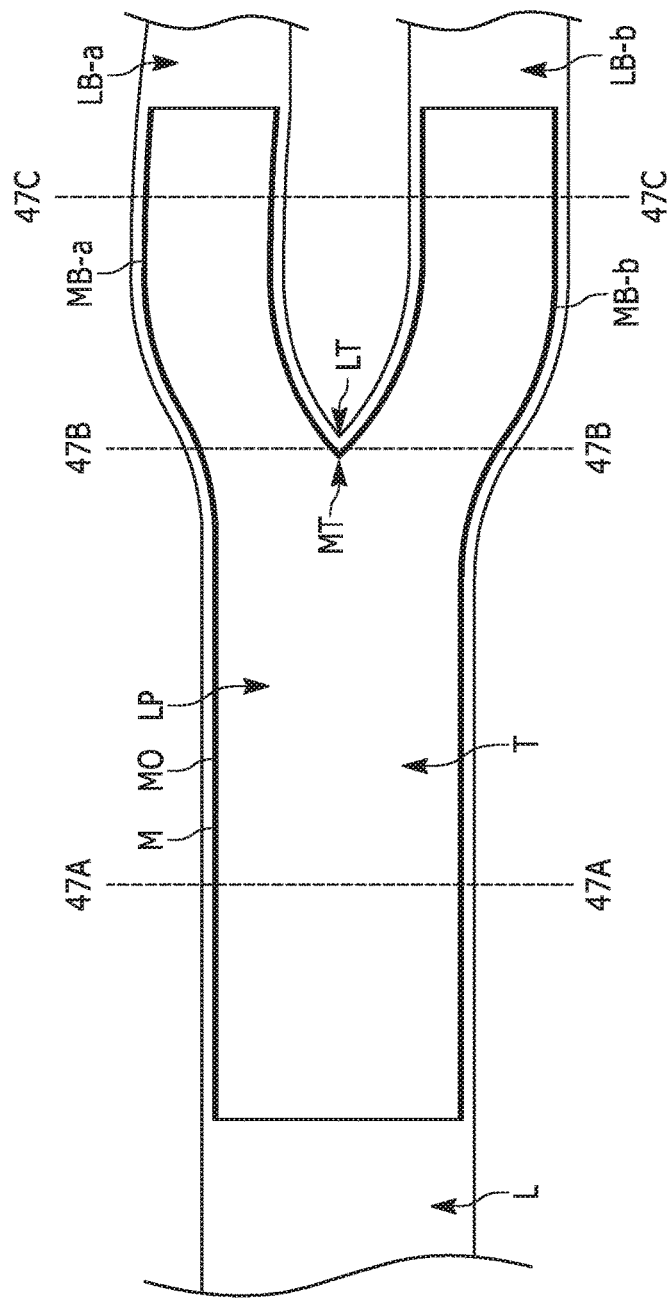
Figure 47A:
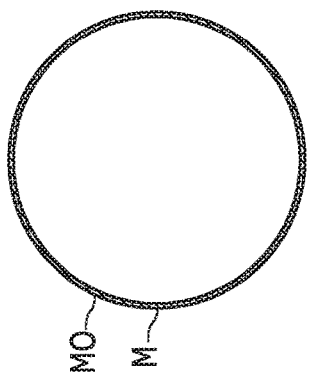

As depicted in FIGS. 45-47, with the bifurcated expandable implant M in the expanded condition, the outer sheath 530, the shaft 102, the inner sheath 958, and/or the at least one guidewire 2890a, 2890b, may be removed from at least one of the target patient tissue site T, the patient lumen main portion LP, and at least one of the patient lumen branches LB-a, LB-b. For example, as shown in FIGS. 45-46, at least one of the outer sheath 530 and the inner sheath 958 may be moved in the longitudinally distal direction, and/or the shaft 102 may be moved in the longitudinally proximal direction. As shown in FIGS. 46-47, once at least a portion of the elastic skirts 222a, 222b of the shaft 102 are adjacent to, in contact with, or disposed within the outer sheath open tip 540, the implant delivery system 100 may be moved in the longitudinally proximal direction to remove the implant delivery system 100 from the target patient tissue site T, while maintaining the expanded bifurcated expandable implant M at the target patient tissue site T.

Figure 48:
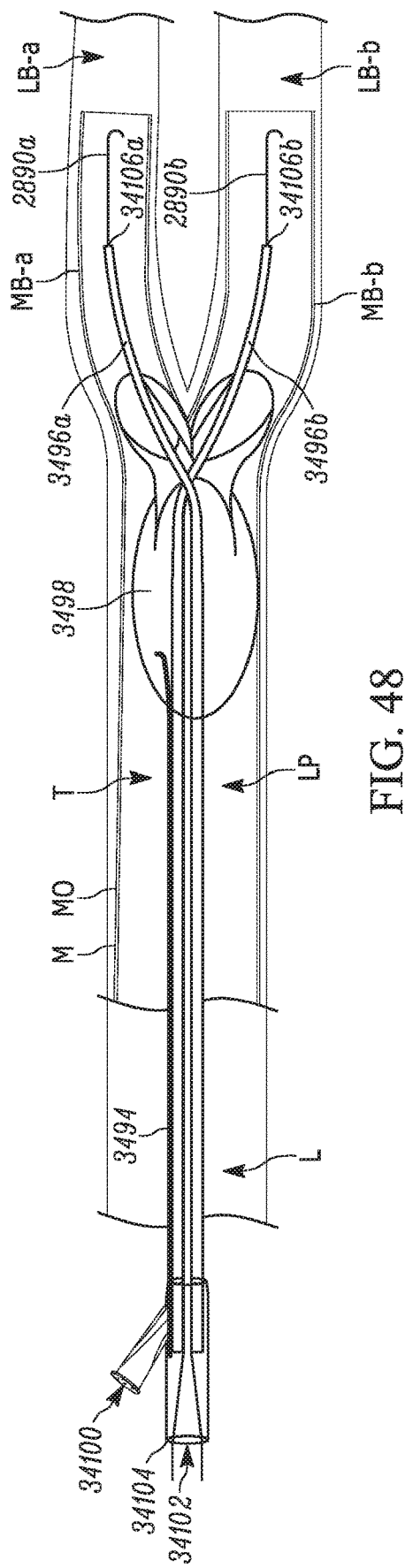

As shown in FIG. 48, after the implant delivery system 100 has been removed, a secondary device (such as the balloon dilation device 3494) may be directed over at least one of the guidewires 2890a, 2890b to perform a medical procedure with the secondary device at the target patient tissue site T, the patient lumen main portion LP, and/or at the one of the patient lumen branches LB-a, LB-b, in a similar sequence to that described above.

Although the above descriptions of the example sequence of operation for the implant delivery system 100 reference the implant delivery systems 100 depicted in FIGS. 17-18, one of ordinary skill in the art will understand, given the teachings of the present application, how to similarly operate any configuration for the shaft 102, the outer sheath 530, and the inner sheath, when provided.

Any of the alternate outer sheath 102 configurations, the alternate shaft 1030 configurations, the alternate inner sheath configurations 958, when provided, the at least one c-clip 556, when provided, the reinforcing element 128, when provided, the nosecones 118a, 118b, when provided, the elastic skirts 222a, 222b, when provided, the open slit cover members 1274a, 1274b, 1274c, 1274d, and the balloon dilation device 3494, when provided, of the implant delivery system 100 may be at least partially formed from silicone, polyethylene, polypropylene, stainless steel, titanium, rubber, latex, polychloroprene, nylon, any other biocompatible material, or any combination thereof.

The bifurcated expandable implant M may be at least partially formed from materials having self-expanding properties, such as, but not limited to, stainless steel and shape memory materials. An example of a shape memory material is, for example, Nitinol. In such case, the bifurcated expandable implant M at least partially formed from materials having self-expanding properties may be moved to the collapsed condition through a direct and/or indirect user interaction, and mounted on the shaft outer surface 124. For example, a bifurcated expandable implant M at least partially formed from a shape memory material may be cooled to a temperature below the transition temperature range, moved to the collapsed condition, and mounted on the shaft outer surface 124. When the bifurcated expandable implant M at least partially formed from a shape memory material is exposed at the target patient tissue site T, the self-expanding properties of the bifurcated expandable implant M may at least partially cause the bifurcated expandable implant M to move from the collapsed condition toward the expanded condition. Further, the temperature of the environment at the target patient tissue site T at least partially causes the bifurcated expandable implant M at least partially formed from a shape memory material to move from the collapsed condition toward the expanded condition.

It is contemplated that a bifurcated expandable implant M at least partially formed from a shape memory material may be more easily conformable to the shape of the target patient tissue site T than what a bifurcated expandable implant M not made at least partially from a shape memory material would be. However, a bifurcated expandable implant M that has self-expanding properties, but is not at least partially made from a shape memory material, may not have to be cooled in order to be moved toward the collapsed condition, and/or may not require the temperature of the of the environment at the target patient tissue site T in order to move from the collapsed condition toward the expanded condition.

It is contemplated that at least one of the alternate outer sheath 530 configurations, the alternate shaft 102 configurations, the alternate inner sheath 958 configurations, when provided, and the balloon dilation device 3494, when provided of the implant delivery system 100 may be disposed within one or more conventional sheaths (not shown) to deliver at least a portion of the implant delivery system 100 to the target patient tissue site T through a patient tissue access point.

Further, the implant delivery system 100 provides the user with the ability to deploy at least one bifurcated expandable implant M with at least two expandable implant branches MB-a, MB-b in a patient lumen L having at least two patient lumen branches LB-a, LB-b over at least two guidewires 2890a, 2890b, while maintaining and protecting wire access across all respective patient lumen branches LB-a, LB-b. For example, at least one of the second guidewire distal ends 2888a, 2888b, the at least one outer sheath open tip 540a, 540b, the at least two outer sheath open slits 548a, 584b, when provided, the at least two shaft branches 112a, 112b, the at least two expandable implant branches MB-a, MB-b, and the inner sheath 958, when provided, allows the user to deploy a bifurcated expandable implant M while maintaining and protecting guidewire 2890a, 2890b access across all respective patient lumen branches LB-a, LB-b because portions of the implant delivery system 100 may be inserted and removed from the target patient tissue site T without the substantial loss of access to all respective patient lumen side branches B.

It is contemplated that the shaft 102 having at least two shaft lumens 126a, 126b may at least partially assist the user with preventing the corresponding guidewires 2890a, 2890b from becoming entangled with one another when each guidewire proximal end 2892a, 2892b is inserted through a respective shaft lumen 126a, 126b.

It is contemplated that at least one of the alternate outer sheath 530 configurations, the alternate shaft 102 configurations, the alternate inner sheath 958 configurations, when provided, and the bifurcated expandable implant M, when provided, of the implant delivery system 100 may be pre-arranged, and/or pre-packaged, prior to use. For example, a shaft 102 may be prearranged with an outer sheath 530 such that the shaft 102 is positioned within the outer sheath lumen 544 with at least a portion of the shaft body 108 and the inner sheath 958 being radially adjacent to at least a portion of the outer sheath body 536, at least a portion of each of the shaft branches 112a, 112b being positioned radially adjacent to a respective outer sheath branch 546a, 546b, when provided, and each of the nosecones 118a, 118b, when provided, being longitudinally adjacent to a respective outer sheath open tip 540a, 540b.

Although the expandable implant M has been described as being a bifurcated expandable implant M having at least two expandable implant branches MB-a, MB-b, it is contemplated that the expandable implant M may have one or no expandable implant branches. In such case, one of ordinary skill in the art will understand, given the teachings of the present application, how to deploy any such differently configured expandable implant.

While aspects of this disclosure have been particularly shown and described with reference to the example aspects above, it will be understood by those of ordinary skill in the art that various additional aspects may be contemplated. For example, the specific methods described above for using the apparatus are merely illustrative; one of ordinary skill in the art could readily determine any number of tools, sequences of steps, or other means/options for placing the above-described apparatus, or components thereof, into positions substantively similar to those shown and described herein. In an effort to maintain clarity in the Figures, certain ones of duplicative components shown have not been specifically numbered, but one of ordinary skill in the art will realize, based upon the components that were numbered, the element numbers which should be associated with the unnumbered components; no differentiation between similar components is intended or implied solely by the presence or absence of an element number in the Figures. Any of the described structures and components could be integrally formed as a single unitary or monolithic piece or made up of separate sub-components, with either of these formations involving any suitable stock or bespoke components and/or any suitable material or combinations of materials; however, the chosen material(s) should be biocompatible for many applications. Any of the described structures and components could be disposable or reusable as desired for a particular use environment. Any component could be provided with a user-perceptible marking to indicate a material, configuration, at least one dimension, or the like pertaining to that component, the user-perceptible marking potentially aiding a user in selecting one component from an array of similar components for a particular use environment. A "predetermined" status may be determined at any time before the structures being manipulated actually reach that status, the "predetermination" being made as late as immediately before the structure achieves the predetermined status. The term "substantially" is used herein to indicate a quality that is largely, but not necessarily wholly, that which is specified—a "substantial" quality admits of the potential for some relatively minor inclusion of a non-quality item. Though certain components described herein are shown as having specific geometric shapes, all structures of this disclosure may have any suitable shapes, sizes, configurations, relative relationships, cross-sectional areas, or any other physical characteristics as desirable for a particular application. Any structures or features described with reference to one aspect or configuration could be provided, singly or in combination with other structures or features, to any other aspect or configuration, as it would be impractical to describe each of the aspects and configurations discussed herein as having all of the options discussed with respect to all of the other aspects and configurations. A device or method incorporating any of these features should be understood to fall under the scope of this disclosure as determined based upon the claims below and any equivalents thereof.

Other aspects, objects, and advantages may be obtained from a study of the drawings, the disclosure, and the appended claims.

I claim:

1. A bifurcated implant delivery system, comprising:
   a shaft having
      a shaft proximal end having at least two shaft proximal openings,
      a shaft distal end having at least two shaft branches engaging and longitudinally extending distally from a shaft body distal end, each of the shaft branches having a shaft open tip,
      a shaft body longitudinally extending between the shaft proximal end and the shaft distal end,
      at least one shaft lumen, the at least one shaft lumen longitudinally extending between a respective one of the at least two shaft proximal openings and at least one of the respective shaft open tips, and
      a reinforcing element engaging and longitudinally extending distally from the shaft body distal end, the reinforcing element being configured to directly contact a bifurcated expandable implant to maintain the bifurcated expandable implant in a predetermined position; and
   an outer sheath having
      an outer sheath proximal end having an outer sheath proximal opening,
      an outer sheath distal end having at least one outer sheath open tip, and
      an outer sheath lumen longitudinally extending between the outer sheath proximal opening and the at least one outer sheath open tip, the outer sheath lumen for selectively holding at least a portion of the shaft and the bifurcated expandable implant therein.

2. The implant delivery system of claim 1, wherein each of the shaft branches has a radially extending nosecone at a respective shaft branch distal end, each of the nosecones pointing in a longitudinally distal direction.

3. The implant delivery system of claim 2, wherein each of the nosecones has at least one elastic skirt longitudinally extending in the proximal direction, each of the elastic skirts for selectively restricting at least a portion of a respective expandable implant branch from expanding from a collapsed condition when the expandable implant is operatively joined to the shaft.

4. The implant delivery system of claim 3, including an inner sheath having an inner sheath proximal end and an inner sheath distal end, the inner sheath proximal end having an inner sheath proximal opening, the inner sheath distal end having an inner sheath open tip, the inner sheath having an inner sheath lumen extending between the inner sheath proximal opening and the inner sheath open tip, the inner sheath lumen for selectively preventing at least a portion of the expandable implant from expanding from a collapsed condition when at least a portion of the expandable implant is disposed within the inner sheath lumen.

5. The implant delivery system of claim 1, wherein the outer sheath distal end has at least two outer sheath branches, each of the outer sheath branches having an outer sheath branch open slit and an outer sheath open tip, each of the outer sheath branch open slits longitudinally extending between a respective outer sheath branch proximal opening and a respective outer sheath open tip, each of the outer sheath branch open slits radially facing an outer sheath longitudinal axis, the outer sheath lumen longitudinally extending between the outer sheath proximal opening and each of the outer sheath open tips, the outer sheath lumen for at least partially selectively preventing at least one of an expandable implant body and expandable implant branches from expanding from a collapsed condition when the expandable implant is disposed within the outer sheath lumen.

6. The implant delivery system of claim 5, wherein each of the outer sheath branch open slits inwardly tapers between the respective outer sheath branch proximal end and the respective outer sheath open tip of a respective outer sheath branch.

7. The implant delivery system of claim 5, wherein each of the shaft branches has a radially extending nosecone at a respective shaft branch distal end, each of the nosecones pointing in a longitudinally distal direction.

8. The implant delivery system of claim 5, including an inner sheath having an inner sheath proximal end and an inner sheath distal end, the inner sheath proximal end having an inner sheath proximal opening, the inner sheath distal end having an inner sheath open tip, the inner sheath having an inner sheath lumen extending between the inner sheath proximal opening and the inner sheath open tip, the inner sheath lumen for selectively preventing at least a portion of the expandable implant body from expanding from a collapsed condition when at least a portion of the expandable implant is disposed within the inner sheath lumen.

9. The implant delivery system of claim 8, wherein the inner sheath has at least one set of open slit cover members, the open slit cover members longitudinally extending from the inner sheath distal end, each open slit cover member of a respective set of open slit cover members being oppositely positioned on the inner sheath distal end from another open slit cover member of the respective set of open slit cover members, and wherein when the inner sheath is operatively joined to the outer sheath, at least a portion of each open slit cover member is positioned within the outer sheath lumen adjacent to a respective outer sheath branch open slit and at least partially selectively covers the respective outer sheath branch open slit.

10. The implant delivery system of claim 9, wherein the inner sheath has a first set of open slit cover members and a second set of open slit cover members, the first set of open slit cover members being oppositely positioned on the inner sheath distal end from the second set of open slit cover members, wherein when the inner sheath is operatively joined to the outer sheath, at least a portion of the open slit cover members of the first set of open slit cover members is positioned within the outer sheath lumen adjacent to a first of the outer sheath branch open slits and at least partially covers the first of the outer sheath branch open slits, and at least a portion of the open slit cover members of the second set of open slit cover members is positioned within the outer sheath lumen adjacent to a second of the outer sheath branch open slits and at least partially covers the second of the outer sheath branch open slits.

11. The implant delivery system of claim 5, wherein each outer sheath branch open slit has an outer sheath branch open slit first surface and an outer sheath branch open slit second surface, the outer sheath branch open slit first surface being oppositely facing the outer sheath branch open slit second surface, the outer sheath branch open slit first surface and the outer sheath branch open slit second surface being selectively elastically separable, and wherein at least one c-clip is embedded in the outer sheath radially between the outer sheath outer surface and the outer sheath lumen and radially adjacent to a respective outer sheath branch open slit, the c-clip at least partially selectively preventing the outer sheath branch open slit first surface from elastically separating from the outer sheath branch open slit second surface.

12. The implant delivery system of claim 1, including an inner sheath having an inner sheath proximal end and an inner sheath distal end, the inner sheath proximal end having an inner sheath proximal opening, the inner sheath distal end having an inner sheath open tip, the inner sheath having an inner sheath lumen extending between the inner sheath proximal opening and the inner sheath open tip, the inner sheath lumen for selectively preventing at least a portion of the expandable implant from expanding from a collapsed condition when at least a portion of the expandable implant is disposed within the inner sheath lumen.

13. A bifurcated implant delivery system, comprising:
a shaft having
   a shaft proximal end having at least two shaft proximal openings,
   a shaft distal end having at least two shaft branches longitudinally extending from a shaft body distal end, each of the shaft branches having a shaft open tip,
   a shaft body longitudinally extending between the shaft proximal end and the shaft distal end, and
   at least one shaft lumen, the at least one shaft lumen longitudinally extending between a respective one of the at least two shaft proximal openings and at least one of the respective shaft open tips;
an inner sheath having
   an inner sheath proximal end having an inner sheath proximal opening,
   an inner sheath distal end having an inner sheath open tip, and
   an inner sheath lumen longitudinally extending between the inner sheath proximal opening and the inner sheath open tip, the inner sheath lumen for selectively preventing at least a portion of an expandable implant body of a bifurcated expandable implant from expanding from a collapsed condition when at least a portion of the bifurcated expandable implant is disposed within the inner sheath lumen; and
an outer sheath having
   an outer sheath proximal end having an outer sheath proximal opening,
   an outer sheath distal end having at least two outer sheath branches, each of the outer sheath branches having an outer sheath branch open slit and an outer sheath open tip, each of the outer sheath branch open slits longitudinally extending between a respective outer sheath branch proximal opening and a respective outer sheath open tip, each of the outer sheath branch open slits radially facing an outer sheath longitudinal axis, and an outer sheath lumen longitudinally extending between the outer sheath proximal opening and each of the outer sheath open tips, the outer sheath lumen for selectively holding at least a portion of the shaft, at least a portion of the inner sheath and the bifurcated expandable implant therein, the outer sheath lumen for at least partially selectively preventing at least one of the expandable implant body and expandable implant branches from expanding from the collapsed condition when the bifurcated expandable implant is disposed within the outer sheath lumen.

14. The implant delivery system of claim 13, wherein each outer sheath branch open slit has an outer sheath branch open slit first surface and an outer sheath branch open slit second surface, the outer sheath branch open slit first surface being oppositely facing the outer sheath branch open slit second surface, the outer sheath branch open slit first surface and the outer sheath branch open slit second surface being selectively elastically separable, and wherein at least one c-clip is embedded in the outer sheath radially between the outer sheath outer surface and the outer sheath lumen and radially adjacent to a respective outer sheath branch open slit, the c-clip at least partially selectively preventing the outer sheath branch open slit first surface from elastically separating from the outer sheath branch open slit second surface.

15. The implant delivery system of claim 13, further comprising:

the bifurcated expandable implant, the bifurcated expandable implant being a single implant having an expandable implant body, at least two expandable implant branches, and an expandable implant transition portion longitudinally between the expandable implant body and the at least two expandable implant branches.

16. A method for deploying a bifurcated expandable implant in a bifurcated patient lumen, the method comprising:

providing the bifurcated implant delivery system of claim 1;

providing at least one bifurcated expandable implant having an expandable implant body, at least two expandable implant branches, and an expandable implant transition portion longitudinally between the expandable implant body and the at least two expandable implant branches;

mounting the at least one bifurcated expandable implant circumferentially on the shaft outer surface with the expandable implant body circumferentially mounted on at least a portion of the shaft body, and each of the expandable implant branches circumferentially mounted on a respective shaft branch;

collectively inserting at least a portion of the at least one bifurcated expandable implant and at least a portion of the shaft into at least a portion of the outer sheath lumen;

inserting at least two guidewires into a target patient tissue site in a patient lumen with each guidewire distal end of the at least two guidewires being positioned in a respective patient lumen branch;

directing each guidewire proximal end of the at least two guidewires through the at least one shaft lumen;

directing the implant delivery system to the target patient tissue site along the at least two guidewires;

positioning the implant delivery system at the target patient tissue site with at least a portion of the outer sheath, at least a portion of the shaft body, and at least a portion of the expandable implant body being positioned in a patient lumen main portion, at least a portion of each shaft branch and at least a portion of each expandable implant branch being positioned in a respective patient lumen branch, and at least a portion of the expandable implant transition portion being positioned at a patient lumen transition portion;

positioning the shaft with a reinforcing element distal end at least partially contacting at least a portion of the expandable implant transition portion, and with at least a portion of the reinforcing element distal end being at the patient lumen transition portion;

with the implant delivery system positioned at the target patient tissue site, exposing at least a portion of the at least one bifurcated expandable implant by urging the outer sheath in the longitudinally proximal direction, while maintaining each of the at least two guidewires, the expandable implant body, and the shaft body at the patient lumen main portion, the guidewire distal ends, the expandable implant branches, and the shaft branches at the respective patient lumen branches, and the reinforcing element distal end and the expandable implant transition portion at the patient lumen transition portion, the contact between the expandable implant transition portion and the reinforcing element distal end at least partially maintaining the expandable implant transition portion at the patient lumen transition portion while the outer sheath is urged in the proximal direction; and with the at least a portion of the at least one bifurcated expandable implant exposed, utilizing properties of the at least one bifurcated expandable implant to move the exposed portion of the at least one bifurcated expandable implant toward an expanded condition.

17. A method for deploying a bifurcated expandable implant in a bifurcated patient lumen, the method comprising:

providing the bifurcated implant delivery system of claim 13;

providing at least one bifurcated expandable implant having an expandable implant body, at least two expandable implant branches, and an expandable implant transition portion longitudinally between the expandable implant body and the at least two expandable implant branches;

mounting the at least one bifurcated expandable implant circumferentially on the shaft outer surface with the expandable implant body circumferentially mounted on at least a portion of the shaft body, and each of the expandable implant branches circumferentially mounted on a respective shaft branch;

with the at least one bifurcated expandable implant mounted on the shaft, collectively inserting at least a portion of the collapsed expandable implant body and at least a portion of the shaft body into at least a portion of the inner sheath lumen;

collectively inserting at least a portion of the inner sheath, at least a portion of the at least one bifurcated expandable implant and at least a portion of the shaft into at least a portion of the outer sheath lumen;

with at least a portion of the inner sheath, at least a portion of the collapsed bifurcated expandable implant, and at least a portion of the shaft inserted in the outer sheath lumen, positioning the inner sheath, the shaft, and the at least one bifurcated expandable implant in the outer sheath lumen with at least a portion of the inner sheath, at least a portion of the shaft body, and at least a portion of the expandable implant body being in an outer sheath body, and with at least a portion of each shaft branch and at least a portion of each expandable implant branch being in a respective outer sheath branch;

inserting at least two guidewires into a target patient tissue site in a patient lumen with each guidewire distal end of the at least two guidewires being positioned in a respective patient lumen branch;

directing each guidewire proximal end of the at least two guidewires through the at least one shaft lumen;

directing the implant delivery system to the target patient tissue site along the at least two guidewires;

positioning the implant delivery system at the target patient tissue site with
- at least a portion of the outer sheath, at least a portion of the inner sheath, at least a portion of the shaft body, and at least a portion of the expandable implant body being positioned in a patient lumen main portion,
- at least a portion of each outer sheath branch, at least a portion of each shaft branch, and at least a portion of each expandable implant branch being positioned in a respective patient lumen branch, and
- at least a portion of the expandable implant transition portion being positioned at a patient lumen transition portion;

with the implant delivery system positioned at the target patient tissue site, exposing expandable implant branches of the at least one bifurcated expandable implant by urging the outer sheath in the longitudinally proximal direction, movement of the outer sheath in the longitudinally proximal direction causing at least one of the expandable implant branches and the shaft branches to move along a respective outer sheath open slit to selectively elastically separate a respective outer sheath open slit first surface from a respective outer sheath open slit second surface and accordingly permit the outer sheath to be directed in the longitudinally proximal direction, while maintaining each of
- the at least two guidewires, the inner sheath, the expandable implant body, and the shaft body at the patient lumen main portion,
- the guidewire distal ends, the expandable implant branches, and the shaft branches at the respective patient lumen branches, and
- the expandable implant transition portion at the patient lumen transition portion;

with the expandable implant branches exposed, exposing the expandable implant body by urging the inner sheath in the longitudinally proximal direction, while maintaining each of
- the at least two guidewires, the expandable implant body, and the shaft body at the patient lumen main portion,
- the guidewire distal ends, the expandable implant branches, and the shaft branches at the respective patient lumen branches, and
- the expandable implant transition portion at the patient lumen transition portion; and with both the expandable implant branches and the expandable implant body exposed, utilizing properties of the at least one bifurcated expandable implant to move the exposed portion of the at least one bifurcated expandable implant toward an expanded condition.

* * * * *